(12) United States Patent
Wang et al.

(10) Patent No.: US 11,850,247 B2
(45) Date of Patent: Dec. 26, 2023

(54) ANTIVIRAL COMPOUNDS

(71) Applicants: REGENTS OF THE UNIVERSITY OF MINNESOTA, Minneapolis, MN (US); Emory University, Atlanta, GA (US)

(72) Inventors: Zhengqiang Wang, Minneapolis, MN (US); Stefanos G. Sarafianos, Atlanta, GA (US)

(73) Assignees: REGENTS OF THE UNIVERSITY OF MINNESOTA, Minneapolis, MN (US); EMORY UNIVERSITY, Atlanta, GA (US)

( * ) Notice: Subject to any disclaimer, the term of this patent is extended or adjusted under 35 U.S.C. 154(b) by 135 days.

(21) Appl. No.: 17/222,433

(22) Filed: Apr. 5, 2021

(65) Prior Publication Data
US 2021/0322416 A1  Oct. 21, 2021

Related U.S. Application Data

(60) Provisional application No. 63/008,320, filed on Apr. 10, 2020.

(51) Int. Cl.
| | | |
|---|---|---|
| *C07D 403/12* | (2006.01) | |
| *C07D 401/12* | (2006.01) | |
| *C07D 239/96* | (2006.01) | |
| *C07D 239/54* | (2006.01) | |
| *A61K 31/513* | (2006.01) | |
| *A61K 31/495* | (2006.01) | |
| *A61K 31/4439* | (2006.01) | |
| *A61K 31/4184* | (2006.01) | |
| *A61K 31/4178* | (2006.01) | |
| *A61K 31/51* | (2006.01) | |
| *C07D 209/34* | (2006.01) | |
| *C07D 235/02* | (2006.01) | |
| *C07D 241/08* | (2006.01) | |
| *A61P 31/18* | (2006.01) | |
| *A61K 31/517* | (2006.01) | |
| *A61K 31/405* | (2006.01) | |
| *C07C 233/88* | (2006.01) | |
| *A61K 31/167* | (2006.01) | |
| *A61K 45/06* | (2006.01) | |

(52) U.S. Cl.
CPC .......... *A61K 31/517* (2013.01); *A61K 31/167* (2013.01); *A61K 31/405* (2013.01); *A61K 31/4178* (2013.01); *A61K 31/4184* (2013.01); *A61K 31/4439* (2013.01); *A61K 31/495* (2013.01); *A61K 31/513* (2013.01); *A61K 45/06* (2013.01); *A61P 31/18* (2018.01); *C07C 233/88* (2013.01); *C07D 209/34* (2013.01); *C07D 235/02* (2013.01); *C07D 239/54* (2013.01); *C07D 239/96* (2013.01); *C07D 241/08* (2013.01); *C07D 401/12* (2013.01); *C07D 403/12* (2013.01)

(58) Field of Classification Search
CPC .. C07C 233/88; C07D 209/34; C07D 235/02; C07D 239/54; C07D 239/96; C07D 241/08; C07D 403/12; C07D 401/12; A61K 31/512; A61K 31/495; A61K 31/4439; A61K 31/4184; A61K 31/4178; A61K 31/51; A61P 31/18
See application file for complete search history.

(56) References Cited

U.S. PATENT DOCUMENTS 6,426,331 B1 *  7/2002  McKinney ......... C07K 5/06034
                                                    435/7.1

OTHER PUBLICATIONS

Bhattacharya, A., et al., "Structural basis of HIV-1 capsid recognition by PF74 and CPSF6", Proc Natl Acad Sci 111 (52), 18625-18630 (2014).

(Continued)

*Primary Examiner* — Jeffrey S Lundgren
*Assistant Examiner* — Chris E Simmons
(74) *Attorney, Agent, or Firm* — Viksnins Harris Padys Malen LLP

(57) ABSTRACT

The invention provides a compound of formula I, formula II, or formula III:

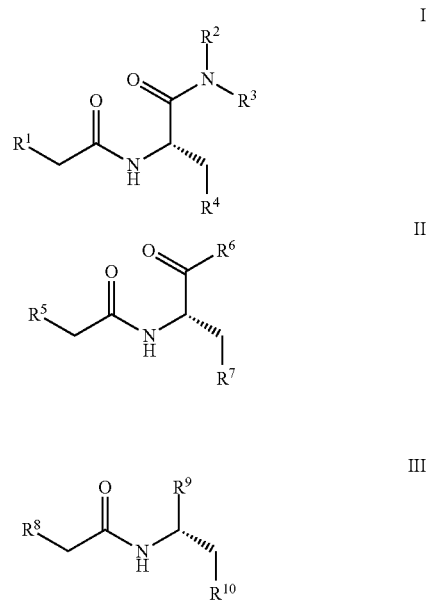

or a salt thereof, wherein $R^1$-$R^{10}$ have any of the values described in the specification, as well as compositions comprising a compound of formula I. The compounds are useful as HIV-1 CA-targeting molecules and as antiviral agents.

20 Claims, No Drawings

(56) References Cited

OTHER PUBLICATIONS

Gres, T, et al., "Structural Virology. X-ray crystal structures of native HIV-1 capsid protein reveal conformational variability", Science 349 (6243), 99-103 (2015).
Price, A, et al., "Host Cofactors and Pharmacologic Ligands Share an Essential Interface in HIV-1 Capsid That Is Lost upon Disassembly", PLOS Pathog 10, e1004459, 1-17 (2014).
Shi, J, et al., "Small-molecule inhibition of human immunodeficiency virus type 1 infection by virus capsid destabilization", J Virol 85, 542-549 (2011).
Vernekar, S, et al., "Toward Structurally Novel and Metabolically Stable HIV-1 Capsid-Targeting Small Molecules", Viruses 12 (4), 452, 1-16 (2020).
Wang, L, et al., "Chemical profiling of HIV-1 capsid-targeting antiviral PF74", Eur J Med Chemical 200, (112427), 56 pages (2020).
Wang, L, et al., "Novel HIV-1 capsid-targeting small molecules of the PF74 binding site", European Journal of Medicinal Chemistry 204, 112626, 20 pages (2020).
Wang, L, et al., "Novel PF74-like small molecules targeting the HIV-1 capsid protein: balance of potency and metabolic stability", Acta Pharmaceutica Sinica B, https://doi.org/10.1016/j.apsb.2020.07.016, 27 pages (2020).
Wang, Z, et al., "Toward HIV-1 CA-targeting antivirals: an emerging paradigm", ICAR 2020 Virtual Meeting.

\* cited by examiner

ANTIVIRAL COMPOUNDS

PRIORITY

This application claims priority to U.S. Provisional Patent Application No. 63/008,320, filed Apr. 10, 2020. The entire content of this United States Provisional Patent Application is incorporated herein by reference.

GOVERNMENT FUNDING

This invention was made with government support under AI120860 awarded by the National Institutes of Health. The government has certain rights in this invention.

BACKGROUND

The capsid protein (CA) of HIV-1 plays critical roles in both early and late steps of viral replication. CA is a key component of the Gag polyprotein, and CA-CA interactions drive the assembly of Gag into the mature viral particle. In addition, CA interacts with various host factors to enable multiple post-entry events, such as uncoating, reverse transcription, nuclear entry and site of integration. CA-targeting small molecules could provide a novel class of HIV-1 drugs with unique antiviral and resistance profiles. Of reported CA inhibitor types, the peptidomimetic PF-74 is particularly interesting due to its potent antiviral activity, well-characterized binding mode, and unique mechanism of action. (Gres, A. T., et al., *Science* 2015, 349, 99; Price, A. J., et al., *PLOS Pathog.* 2014, 10, e1004459; Bhattacharya, A., et al., *Proc. Natl. Acad. Sci. USA* 2014, 111, 18625; and Shi, J., et al., *J. Virol.* 2011, 85, 542-549). PF-74 binds to a well-defined pocket at the CA-CA interface between the CANm and the CAcm of an adjacent monomer. This same pocket is used by a few important host factors, such as Nup153 and CPSF6, to facilitate viral infection. Therefore, compounds targeting this pocket are particularly valuable in developing novel antivirals and probing the molecular basis of CA-host factor interactions. Unfortunately, PF-74 is not a viable drug candidate due primarily to its prohibitively poor metabolic stability.

Currently there is a need for CA-targeting and metabolically stable agents that are useful as mechanistically distinct antivirals.

SUMMARY

The invention provides potent HIV-1 CA-targeting molecules that are useful as antivirals.

In one aspect the present invention provides a compound of formula I, formula II, or formula III:

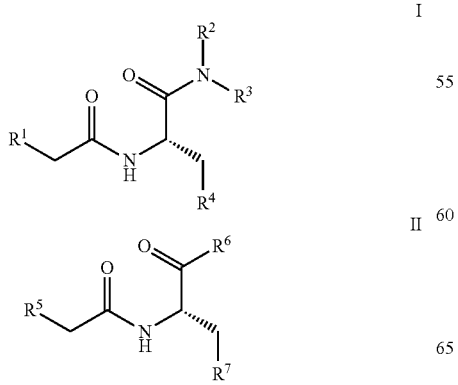

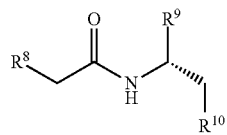

or a salt thereof, wherein:

$R^1$ is selected from the group consisting of:

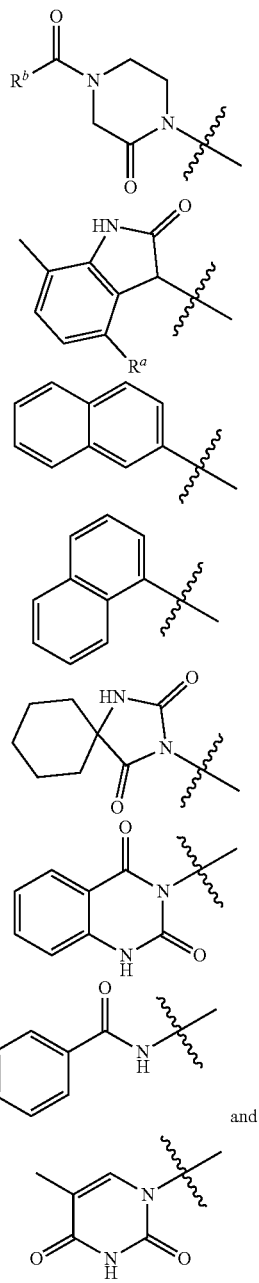

$R^2$ is methyl or ethyl;

$R^3$ is phenyl, optionally substituted at the 3-position with bromo, chloro, fluoro, methyl, or methoxy, and optionally substituted at the 4-position with bromo, chloro, fluoro, methyl, or methoxy;

R⁴ is 4-chloropyridyl, 4-bromopyridyl, or phenyl that is optionally substituted at the 4-position with halo, methyl, ethyl, or methoxy;

R⁵ is selected from the group consisting of:

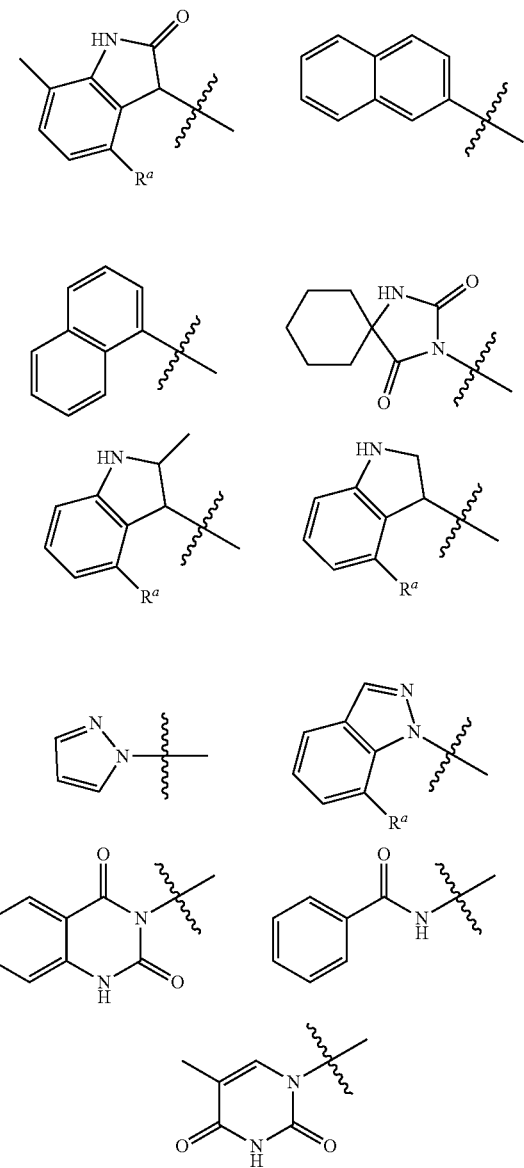

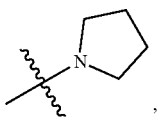

which ring is optionally substituted with carboxy, (C₁-C₆)alkoxycarbonyl, or —C(=O)NR$^c$R$^d$;

R⁷ is 4-chloropyridyl, 4-bromopyridyl, or phenyl that is optionally substituted at the 4-position with halo, methyl, ethyl, or methoxy;

R⁸ is selected from the group consisting of:

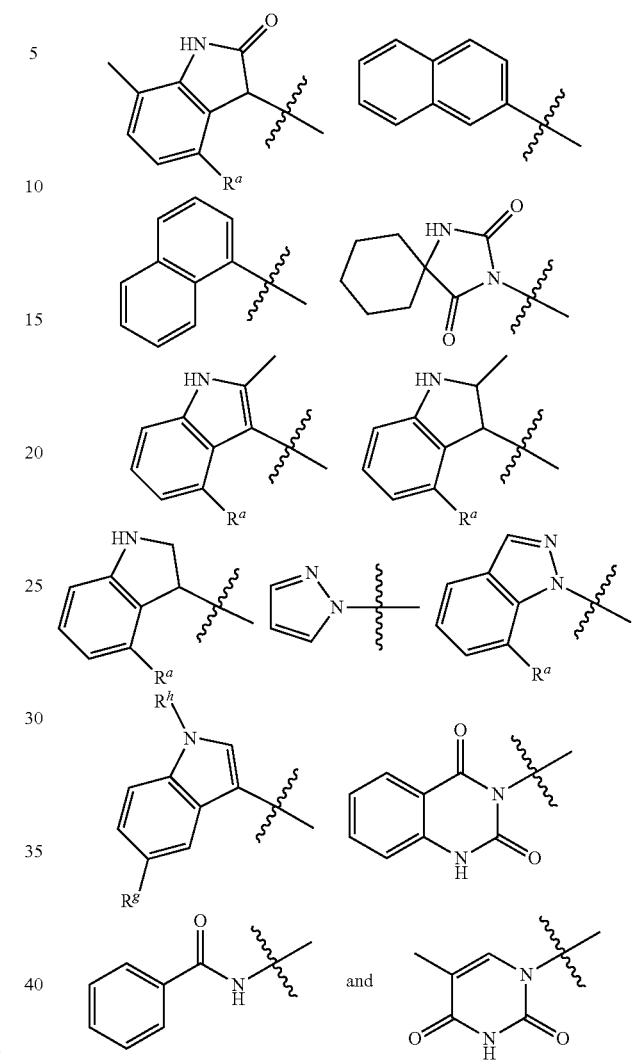

R⁹ is pyridyl that is substituted with phenyl, 4-chlorophenyl, 4-bromophenyl, 4-iodophenyl, or 4-cyanophenyl or R⁹ is imidazole that is substituted with phenyl, 4-chlorophenyl, 4-bromophenyl, 4-iodophenyl, or 4-cyanophenyl;

R¹⁰ is 4-chloropyridyl, 4-bromopyridyl, or phenyl that is optionally substituted at the 4-position with halo, methyl, ethyl, or methoxy;

R$^a$ is H or methyl;

R$^b$ is phenyl that is optionally substituted with one or more groups independently selected from the group consisting of nitro, halo, (C₁-C₆)alkyl, halo(C₁-C₆)alkyl, hydroxy, —SO₂F, and NR$^e$R$^f$;

R$^c$ is H, phenyl, benzyl, or (C₁-C₆)alkyl;

R$^d$ is H, phenyl, benzyl, or (C₁-C₆)alkyl;

R$^e$ is H, hydroxy, or (C₁-C₆)alkyl;

R$^f$ is H or (C₁-C₆)alkyl;

R$^g$ is H, OH, or (C₁-C₆)alkoxy; and

R$^h$ is H or (C₁-C₆)alkyl.

In one aspect the present invention provides a pharmaceutical composition comprising a compound of the invention or a pharmaceutically acceptable salt thereof, and a pharmaceutically acceptable excipient. In one aspect the pharmaceutical composition further comprises a cytochrome P450 inhibitor. In one aspect the cytochrome P450 inhibitor is a CYP3A inhibitor. In one aspect the CYP3A inhibitor is Cobicistat.

In one aspect the present invention provides a method for treating a viral infection in an animal comprising administering to the animal a compound of the invention or a pharmaceutically acceptable salt thereof. In one aspect the viral infection is HIV. In one aspect the method further comprises administering a cytochrome P450 inhibitor to the animal. In one aspect the cytochrome P450 inhibitor is a CYP3A inhibitor. In one aspect the CYP3A inhibitor is Cobicistat.

In one aspect the present invention provides a method for treating a viral infection in an animal comprising administering to the animal, a pharmaceutical composition of the invention.

In one aspect the present invention provides a compound of the invention or a pharmaceutically acceptable salt thereof, for use in medical therapy.

In one aspect the present invention provides a compound of the invention or a pharmaceutically acceptable salt thereof, for the prophylactic or therapeutic treatment of a viral infection (e.g. HIV).

In one aspect the present invention provides a compound of the invention or a pharmaceutically acceptable salt thereof, for the prophylactic or therapeutic treatment of a viral infection, in combination with a cytochrome P450 inhibitor. In one aspect the cytochrome P450 inhibitor is a CYP3A inhibitor. In one aspect the CYP3A inhibitor is Cobicistat.

In one aspect the present invention provides a pharmaceutical composition of the invention for the prophylactic or therapeutic treatment of a viral infection.

In one aspect the present invention provides the use of a compound of the invention or a pharmaceutically acceptable salt thereof, to prepare a medicament for treating a viral infection (e.g. HIV) in an animal. In one aspect the use is in combination with a cytochrome P450 inhibitor. In one aspect the cytochrome P450 inhibitor is a CYP3A inhibitor. In one aspect the CYP3A inhibitor is Cobicistat.

The invention also provides processes and intermediates disclosed herein that are useful for preparing a compound of formula I or a salt thereof.

DETAILED DESCRIPTION

The following definitions are used, unless otherwise described: halo or halogen is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-3}$ means one to three carbons). Examples of alkyl groups include methyl, ethyl, n-propyl, and iso-propyl.

The term "alkoxy" refers to an alkyl groups attached to the remainder of the molecule via an oxygen atom ("oxy"). Examples of alkoxy groups include methoxy, ethoxy, n-propoxy, and iso-propoxy.

The term "halo($C_1$-$C_6$)alkyl" is a ($C_1$-$C_6$)alkyl that is optionally substituted with one or more independently selected halo (e.g., trifluoromethyl).

As used herein a wavy line " ∿ " that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" as used herein includes mammals, such as humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they can rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_3)$alkyl can be methyl, ethyl, propyl, or isopropyl; and $(C_1-C_3)$alkoxy can be methoxy, ethoxy, propoxy, or isopropoxy.

A specific compound or salt is a compound of formula I or a salt thereof.

A specific compound or salt is a compound of formula II or a salt thereof.

A specific compound or salt is a compound of formula III or a salt thereof.

A specific compound or salt is a compound of formula Ia:

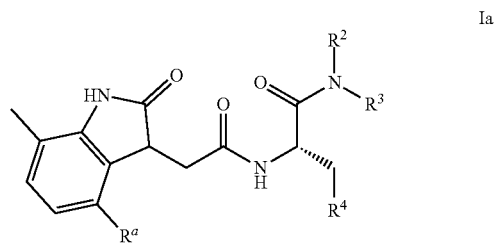

or a salt thereof.

A specific compound or salt is a compound of formula Ia, wherein $R^a$ is H; and $R^3$ is 3-chlorophenyl.

A specific compound or salt is a compound of formula Ia, wherein $R^3$ is phenyl, 3-chlorophenyl, 4-chlorophenyl, 3-fluorophenyl, or 4-fluorophenyl.

A specific compound or salt is a compound of formula Ib:

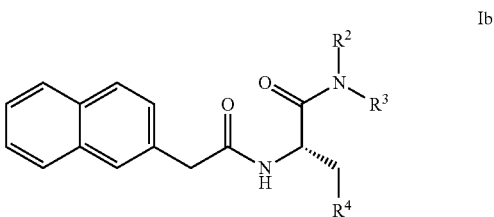

or a salt thereof.

A specific compound or salt is a compound of formula Ib, wherein $R^3$ is 4-methylphenyl or 4-chlorophenyl.

A specific compound or salt is a compound of formula Ic:

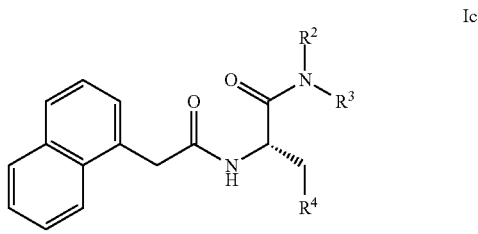

or a salt thereof.

A specific compound or salt is a compound of formula Ic, wherein R³ is phenyl, 4-methylphenyl, or 4-chlorophenyl.

A specific compound or salt is a compound of formula Ie:

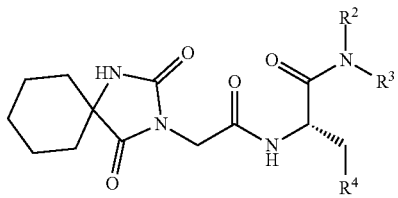

or a salt thereof.

A specific compound or salt is a compound of formula Ie, wherein R³ is phenyl, 4-methylphenyl, 4-methoxyphenyl, or 4-chlorophenyl.

A specific compound or salt is a compound of formula Ig:

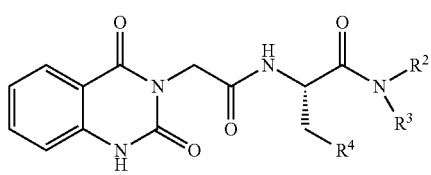

or a salt thereof.

A specific compound or salt is a compound of formula Ih:

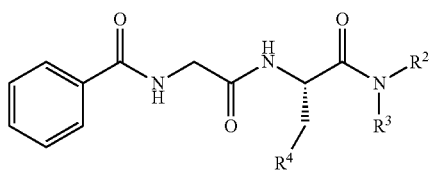

or a salt thereof.

A specific compound or salt is a compound of formula Im

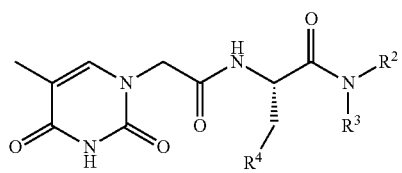

or a salt thereof.

A specific value for R² is methyl.

A specific value for R³ is phenyl, 3-chlorophenyl, 4-chlorophenyl, 3-fluorophenyl, 4-fluorophenyl, 4-methoxyphenyl, 3-bromophenyl, or 4-methylphenyl.

A specific compound or salt is selected form the group consisting of:

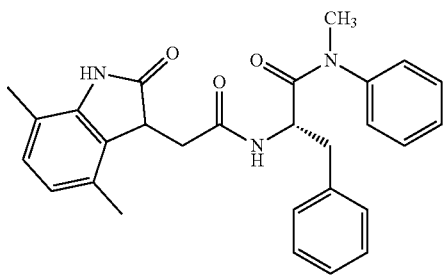

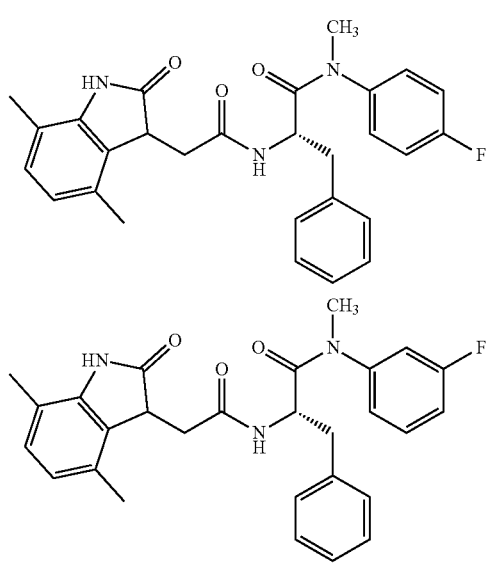

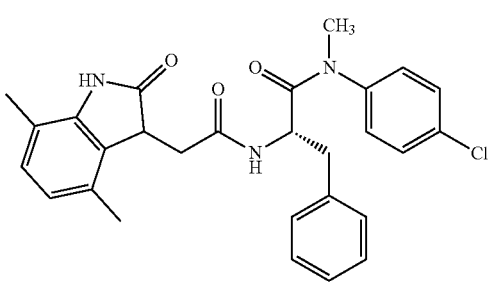

and

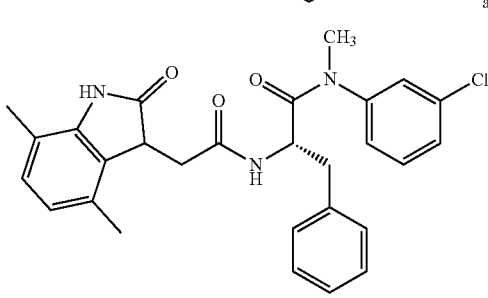

or a salt thereof.

A specific compound or salt is selected form the group consisting of:

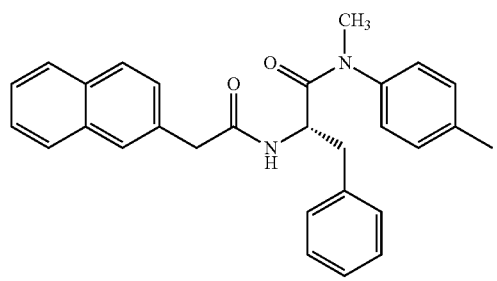

and

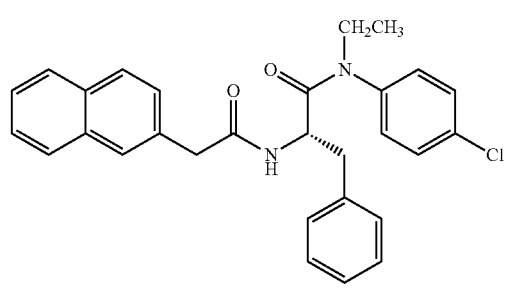

or a salt thereof.

A specific compound or salt is selected form the group consisting of:

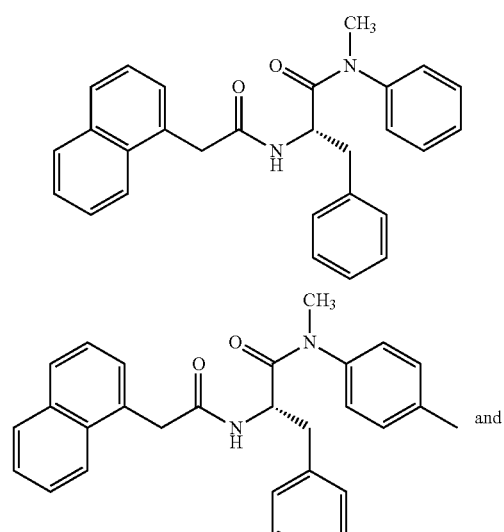

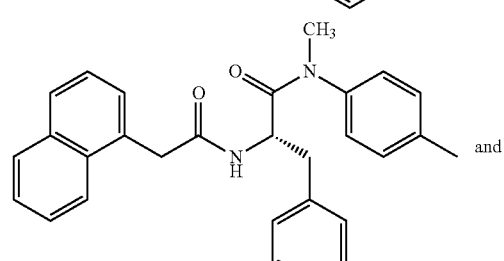

and

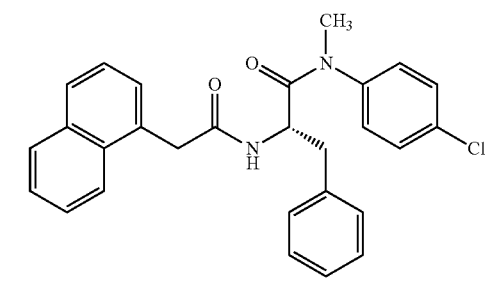

or a salt thereof.

A specific compound or salt is selected form the group consisting of:

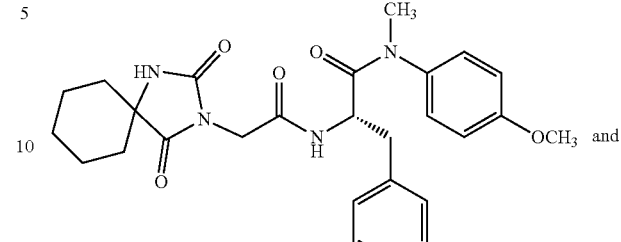

and

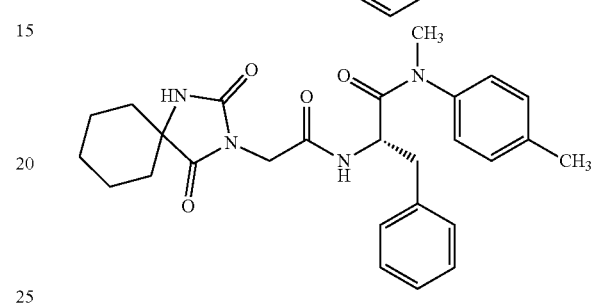

or a salt thereof.

A specific compound or salt is selected form the group consisting of:

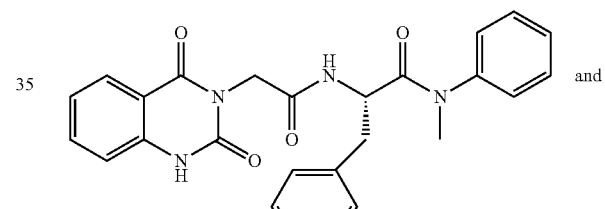

and

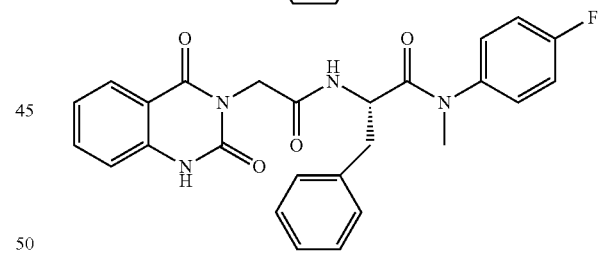

or a salt thereof.

A specific compound or salt is selected form the group consisting of:

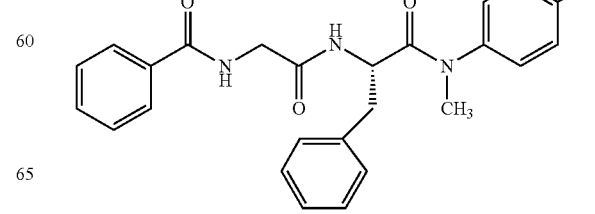

-continued

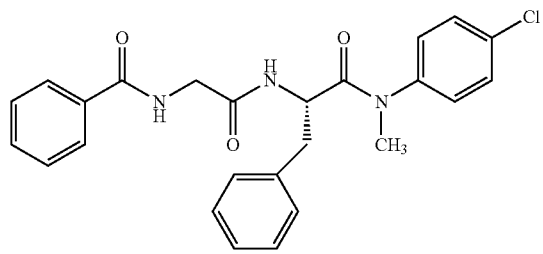

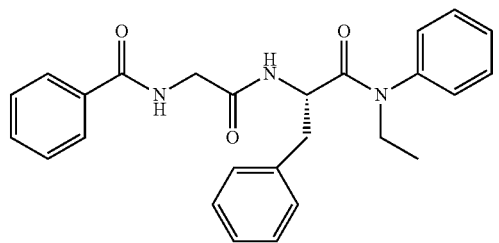

or a salt thereof.

A specific compound or salt is the compound:

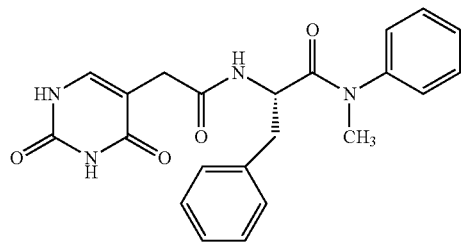 [SMILES: CN(C(=O)[C@H](Cc1ccccc1)NC(=O)Cc1c[nH]c(=O)[nH]c1=O)c1ccccc1]

or a salt thereof.

A specific value for $R^6$ is:

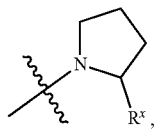

wherein $R^x$ is carboxy, $(C_1-C_6)$alkoxycarbonyl, or —C(=O)NR$^c$R$^d$.

A specific value for $R^6$ is:

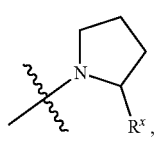

wherein $R^x$ is —C(=O)NR$^c$R$^d$.

A specific compound or salt is:

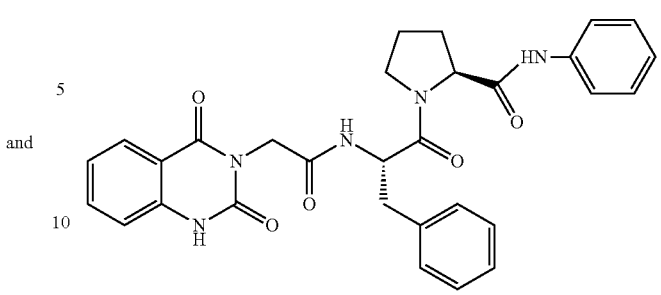

or a salt thereof.

A specific compound or salt is a compound of formula IIIa:

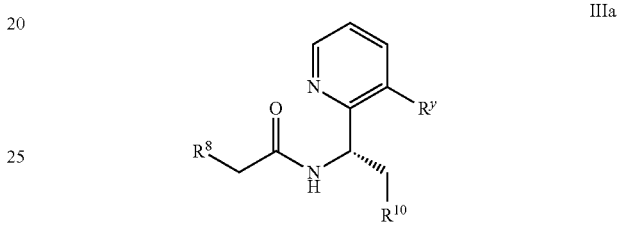

or a salt thereof, wherein $R^y$ is phenyl.

A specific compound or salt is selected from the group consisting of:

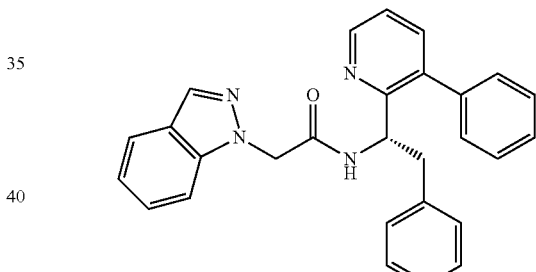

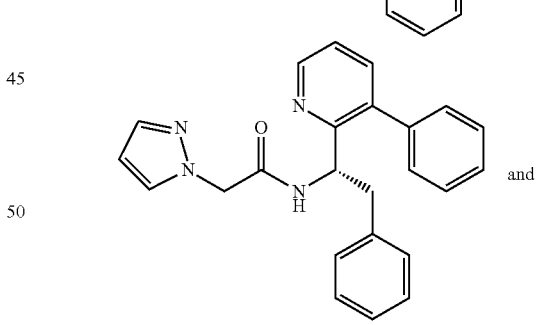

and

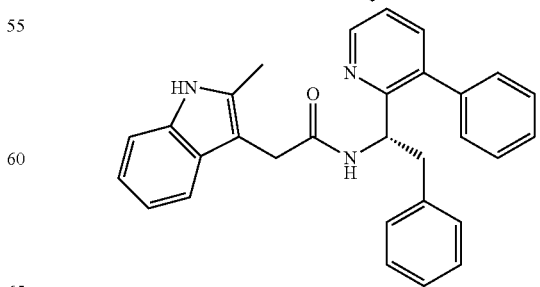

or a salt thereof.

A specific compound or salt is a compound of formula IIIb

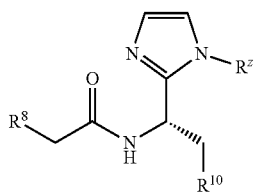

or a salt thereof, wherein $R^z$ is phenyl or 4-cyanophenyl.

A specific compound or salt is selected from the group consisting of:

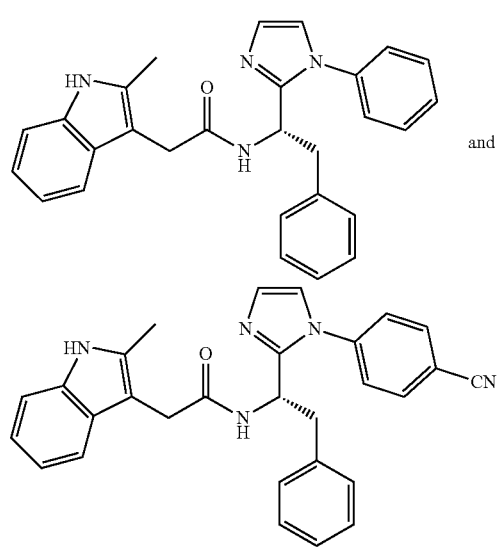

and or a salt thereof.

A specific compound is a compound of formula I, formula II, or formula III:

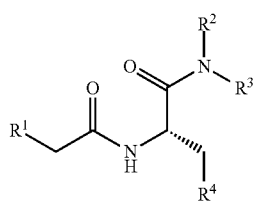
I

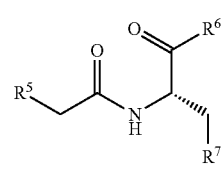
II

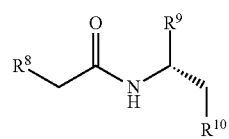
III or a salt thereof, wherein:

$R^1$ is selected from the group consisting of:

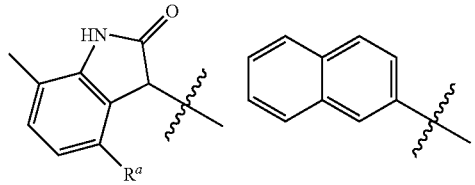

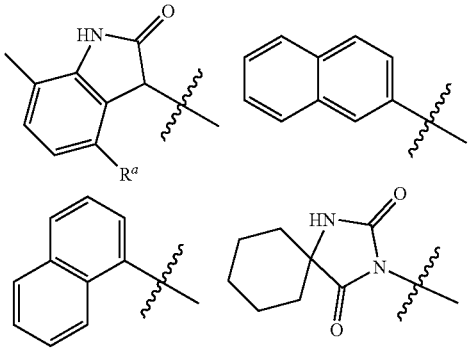

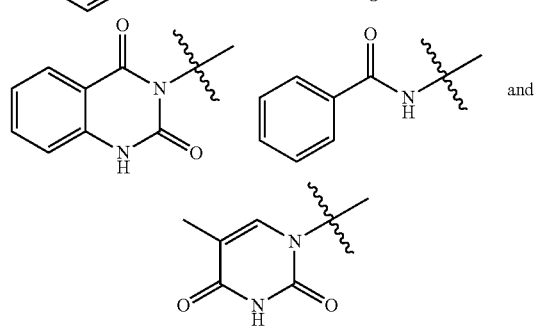

$R^2$ is methyl or ethyl;
$R^3$ is phenyl, optionally substituted at the 3-position with bromo, chloro, fluoro, methyl, or methoxy, and optionally substituted at the 4-position with bromo, chloro, fluoro, methyl, or methoxy;
$R^4$ is 4-chloropyridyl, 4-bromopyridyl, or phenyl that is optionally substituted at the 4-position with halo, methyl, ethyl, or methoxy;
$R^5$ is selected from the group consisting of:

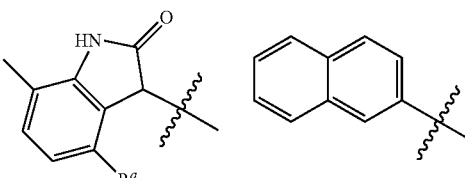

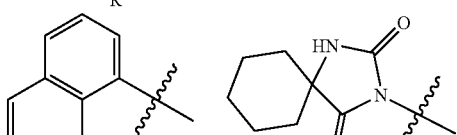

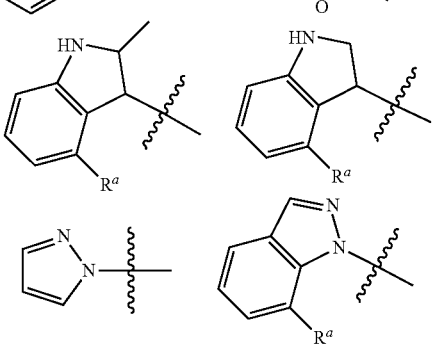

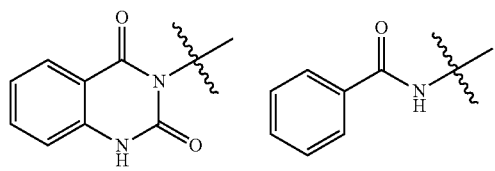

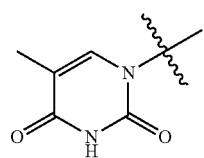

$R^6$ is a ring:

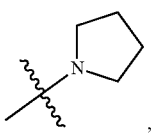 [SMILES: *N1CCCC1]

which ring is optionally substituted with carboxy, $(C_1-C_6)$ alkoxycarbonyl, or —C(=O)NR$^c$R$^d$;

$R^7$ is 4-chloropyridyl, 4-bromopyridyl, or phenyl that is optionally substituted at the 4-position with halo, methyl, ethyl, or methoxy;

$R^8$ is selected from the group consisting of:

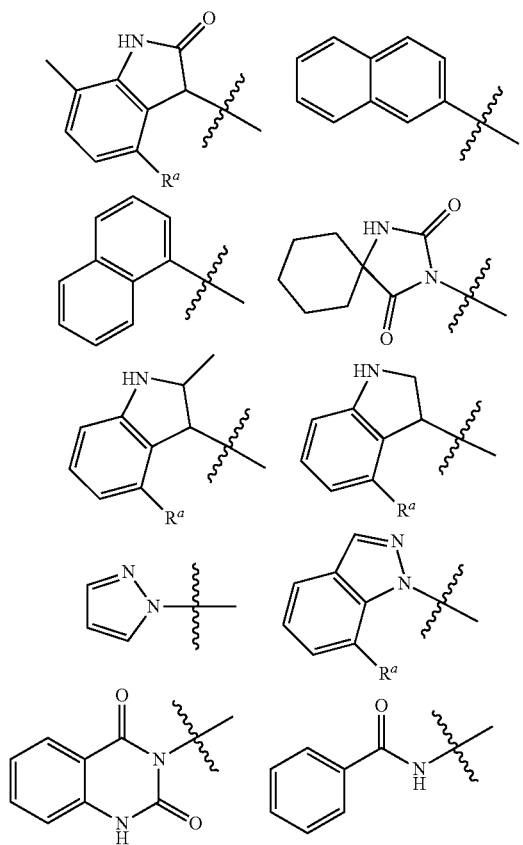

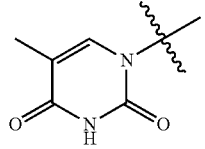

$R^9$ is pyridyl that is substituted with phenyl or 4-cyanophenyl or $R^9$ is imidazole that is substituted with phenyl or 4-cyanophenyl;

$R^{10}$ is 4-chloropyridyl, 4-bromopyridyl, or phenyl that is optionally substituted at the 4-position with halo, methyl, ethyl, or methoxy;

$R^a$ is H or methyl;

$R^c$ is H, phenyl, benzyl, or $(C_1-C_6)$alkyl; and $R^d$ is H, phenyl, benzyl, or $(C_1-C_6)$alkyl.

A specific compound or salt is:

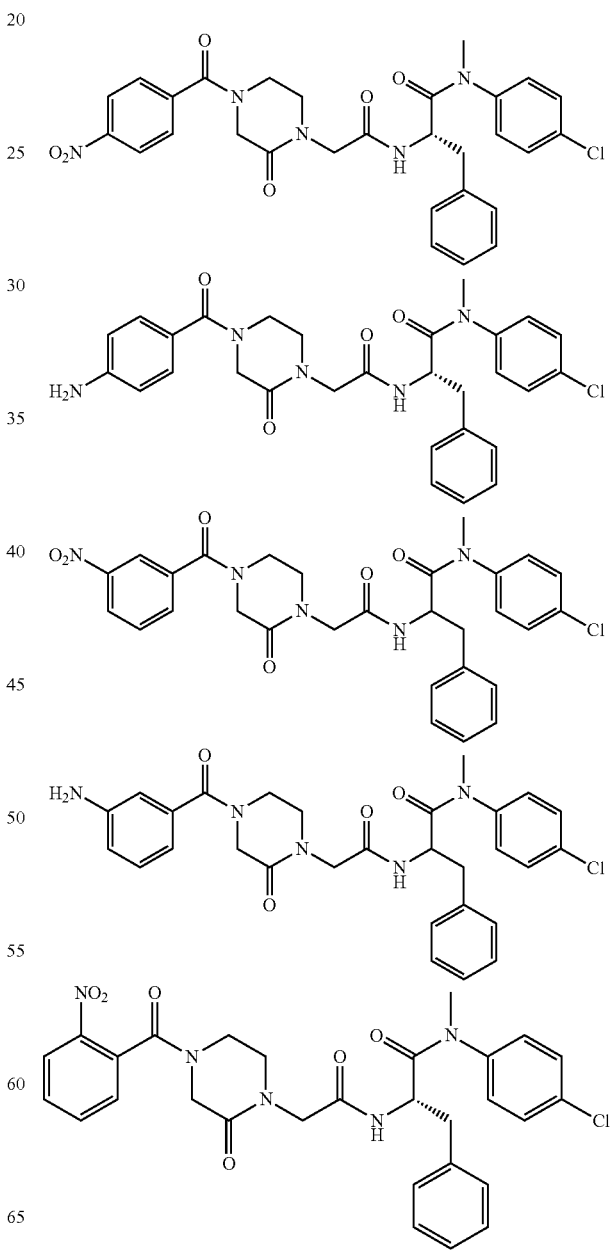

-continued

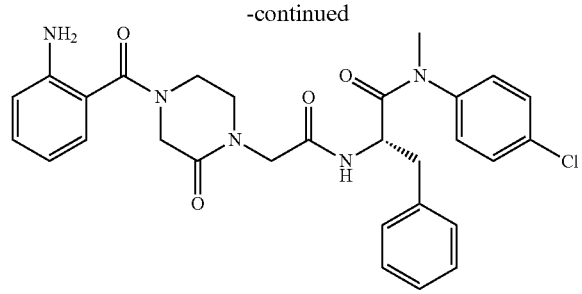

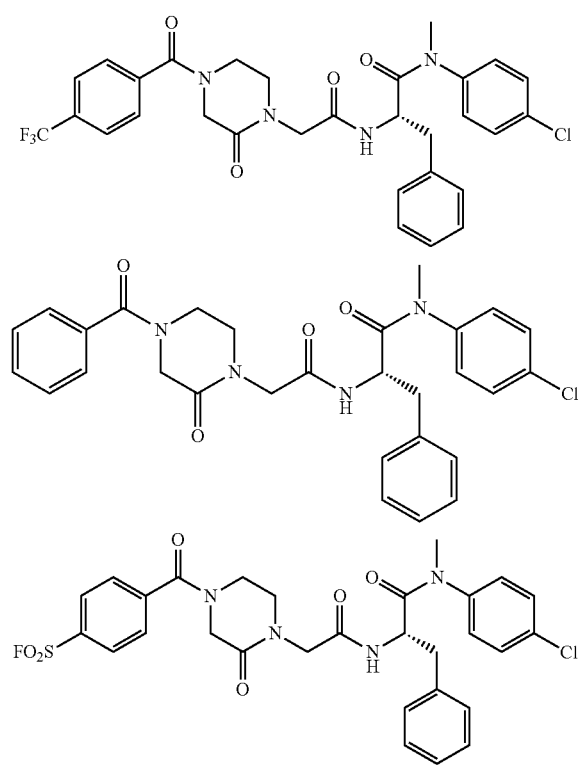

-continued

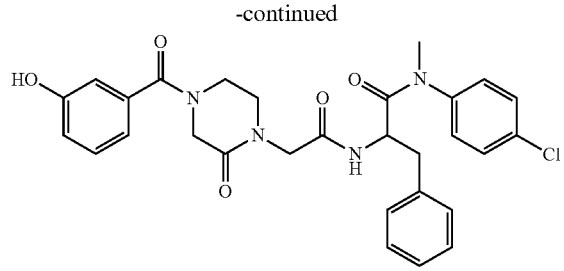

or a salt thereof.

Processes for preparing compounds of formula I are provided as further embodiments of the invention and are illustrated by the following Scheme in which the meanings of the generic radicals are as given above unless otherwise qualified.

Scheme 1

Commercially available (tertbutoxycarbonyl)-L-phenyl-alanine (I) was treated with various amines under a well-established method using T₃P or HATU in the presence of DIPEA to afford II. After removal of Boc protecting group using TFA, an amine III was obtained which was further reacted with acid derivative to produce compounds of the invention.

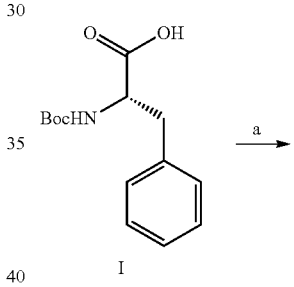

I

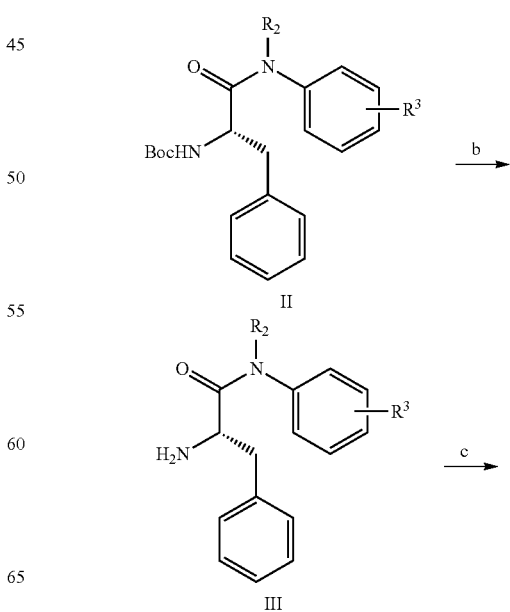

or

-continued

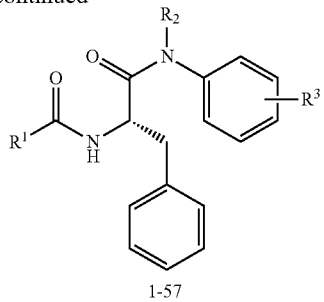

1-57

Reagents and conditions: (a) amine, HATU (or T₃P), DIPEA, DMF, room temperature, 12 hours; (b) TFA; DCM, room temperature, 4-6 hours; (c) acid derivative, HATU, DIPEA, DMF, room temperature, 12 hours.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of HIV. Examples of such agents are described at: aidsinfo.nih.gov/understanding-hiv-aids/fact-sheets/21/58/fda-approved-hiv-medicine, and include Nucleoside Reverse Transcriptase Inhibitors (NRTIs), such as abacavir, emtricitabine, lamivudine, tenofovir disoproxil fumarate, and zidovudine; Non-Nucleoside Reverse Transcriptase Inhibitors (NNRTIs), such as doravin, efavirenz, etravirine, nevirapine, and rilpivirine; Protease Inhibitors, such as atazanavir, darunavir, fosamprenavir, ritonavir, saquinavir, and tipranavir; Fusion Inhibitors, such as enfuvitide; CCR5 Antagonists, such as maraviroc; Integrase Inhibitors such as, doletegravir and raltegravir; Post-Attachment Inhibitors, such as ibalizumab-uiyk; and Pharmacokinetic Enhancers, such as cobicistat. Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal. In one embodiment, the other therapeutic agent is a Nucleoside Reverse Transcriptase Inhibitor (NRTIs), such as abacavir, emtricitabine, lamivudine, tenofovir disoproxil fumarate, or zidovudine. In one embodiment, the other therapeutic agent is a Non-Nucleoside Reverse Transcriptase Inhibitor (NNRTIs), such as doravin, efavirenz, etravirine, nevirapine, or rilpivirine. In one embodiment, the other therapeutic agent is a Protease Inhibitor, such as atazanavir, darunavir, fosamprenavir, ritonavir, saquinavir, or tipranavir. In one embodiment, the other therapeutic agent is a Fusion Inhibitor, such as enfuvitide. In one embodiment, the other therapeutic agent is a CCR5 Antagonist, such as maraviroc. In one embodiment, the other therapeutic agent is an Integrase Inhibitor such as, doletegravir and raltegravir. In one embodiment, the other therapeutic agent is a Post-Attachment Inhibitor, such as ibalizumab-uiyk. In one embodiment, the other therapeutic agent is a Pharmacokinetic Enhancer, such as cobicistat.

Compounds of the invention can also be formulated with or administered in combination with an inhibitor of Cytochrome P450. Metabolic stability is a major absorption, distribution, metabolism and excretion (ADME) property that profoundly impacts drug bioavailability. Peptidomimetics like PF74 are particularly susceptible to phase I metabolism, presumably because they are good substrates for liver metabolizing enzyme subfamily cytochrome P450 3A (CYP3A), which is responsible for the metabolism of at least 50% of all current drugs (Wacher, V. J., et al., *J Pharm Sci* 1998, 87, 1322-30 and Eichelbaum, M.; Burk, O., CYP3A genetics in drug metabolism. *Nat Med* 2001, 7, 285-7). It is known that PF74 is a flawed antiviral candidate due to its prohibitively low metabolic stability (Xu, J. P., et al., *J Drug Des Res* 2018, 5). This was confirmed in our metabolic stability assays, where the half-life ($t_{1/2}$) of PF74 is less than 1 min in both HLMs and MLMs. By contrast, the compound of Example 33 was decisively more stable, particularly in HLMs where its half-life ($t_{1/2}$=31 min) was 44-fold longer than that of PF74 ($t_{1/2}$=0.7 min). When tested in combination with a CYP3A inhibitor Cobicistat (Cobi) (Xu, L. H., et al., *Acs Med Chem Lett* 2010, 1, 209-213), The compound of Example 33 still exhibited significantly longer half-life than that of PF74. Collectively, these observations support Example 33 as a viable antiviral hit and corroborate the hypothesis that the poor metabolic stability of PF74 is due to CYP3A-mediated phase I metabolism.

The invention will now be illustrated by the following non-limiting Examples.

EXAMPLES

All commercial chemicals were used as supplied unless otherwise indicated. Flash chromatography was performed on a Teledyne Combiflash RF-200 with RediSep columns (silica) and indicated mobile phase. $^1$H and $^{13}$C NMR spectra were recorded on a Varian 600 MHz or Bruker 400 spectrometer. Mass data were acquired using an Agilent 6230 TOF LC/MS spectrometer. All NMR and mass spectrometers are located in the shared instrument rooms at the Center for Drug Design, University of Minnesota.

General Procedure for Synthesis of Examples 1-63

To a solution of acid derivative (1 equiv.) in DMF (3 mL), HATU (2 equiv.) and DIPEA (2 equiv.) were add and the mixture was stirred at room temperature for 20 minutes before amine (1.2 equiv.) was added. The mixture was further stirred at room overnight. Upon completion, H$_2$O was added and the reaction mixture was extracted with EtOAc (3×30 mL). The organic phases were combined and washed with brine, dried over anhydrous MgSO$_4$, filtered and concentrated. The product was purified by combi-flash on silica gel using EtOAc in hexane.

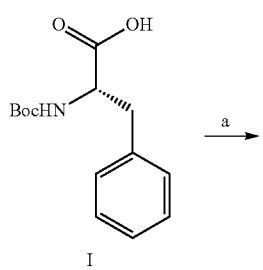

I

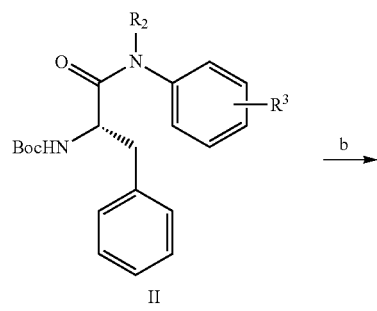

II

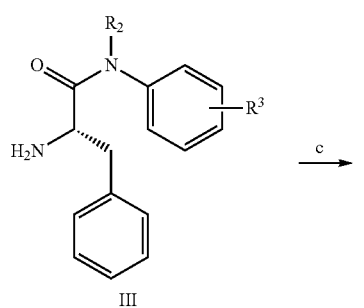

III

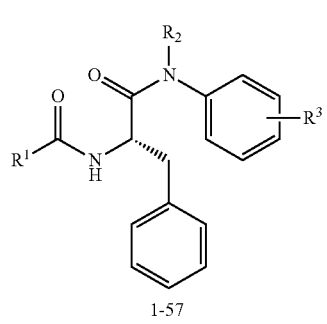

1-57

Reagents and conditions: (a) amine, HATU (or T₃P), DIPEA, DMF, room temperature, 12 hours; (b) TFA; DCM, room temperature, 4-6 hours; (c) acid derivative, HATU, DIPEA, DMF, room temperature, 12 hours.

Example 1. Preparation of (2S)—N-methyl-2-(2-(7-methyl-2-oxoindolin-3-yl)acetamido)-N,3-diphenyl-propanamide (1)

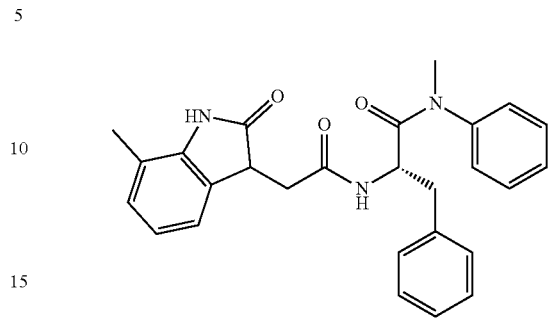

Using the general procedure described above, the title compound was prepared. Yield 70%. $^1$H NMR (600 MHz, CD$_3$OD) δ 7.36-7.31 (m, 3H), 7.22-7.17 (m, 3H), 6.99-6.95 (m, 2H), 6.88-6.83 (m, 3H), 6.75 (t, J=7.6 Hz, 1H), 6.65 (d, J=7.4 Hz, 1H), 4.73-4.63 (m, 1H), 3.72-3.69 (m, 1H), 3.18-3.15 (m, 1H), 2.96-2.82 (m, 2H), 2.71-2.65 (m, 1H), 2.54-2.47 (m, 1H), 2.22 (s, 3H); $^{13}$C NMR (101 MHz, CD$_3$OD) δ 181.8, 181.7, 173.1, 172.3, 172.0, 144.0, 143.9, 142.0, 141.9, 138.2, 138.1, 130.8, 130.5, 130.4, 130.3, 130.2, 130.0, 129.5, 129.3, 128.6, 127.9, 127.8, 123.3, 123.3, 122.9, 122.6, 120.5, 120.4, 53.5, 53.1, 39.5, 39.4, 38.1, 38.0, 37.1, 37.0, 16.7; HRMS-ESI (−) m/z calcd for C$_{27}$H$_{26}$N$_3$O$_3$ [M−H]$^−$ 440.1980, found 440.1985.

Example 2. Preparation of (2S)—N-(4-chlorophenyl)-N-methyl-2-(2-(7-methyl-2-oxoindolin-3-yl)acetamido)-3-phenylpropanamide (2)

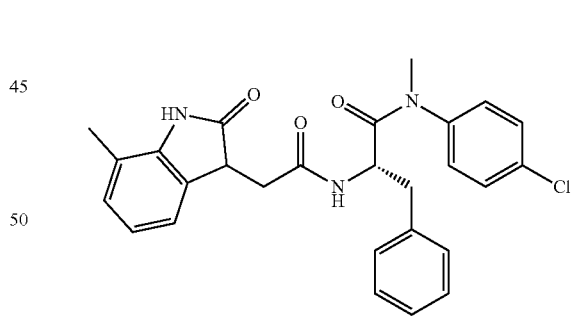

Using the general procedure described above, the title compound was prepared. Yield 70%. $^1$H NMR (600 MHz, CD$_3$OD) δ 7.30-7.21 (m, 5H), 6.99-6.86 (m, 4H), 6.81-6.75 (m, 2H), 6.62 (s, 1H), 4.63-4.55 (m, 1H), 3.73-3.68 (m, 1H), 3.13-3.08 (m, 3H), 2.96-2.82 (m, 2H), 2.71-2.53 (m, 2H), 2.23-2.22 (m, 3H); $^{13}$C NMR (100 MHz, CD$_3$OD) δ 181.8, 181.7, 173.1, 173.0, 172.2, 171.9, 142.6, 142.5, 142.2, 142.0, 138.02, 134.92, 130.72, 130.50, 130.4, 130.3, 130.28, 130.19, 130.1, 130.0, 129.60, 128.0, 123.32, 122.8, 122.6, 120.5, 53.4, 52.9, 44.3, 44.2, 39.71, 39.5, 38.0, 37.8, 37.1, 36.9, 16.7; HRMS-ESI (−) m/z calcd for C$_{27}$H$_{25}$ClN$_3$O$_3$ [M−H]$^−$ 474.1590, found 474.1595.

Example 3. Preparation of (2S)—N-(3-chlorophenyl)-N-methyl-2-(2-(7-methyl-2-oxoindolin-3-yl)acetamido)-3-phenylpropanamide (3)

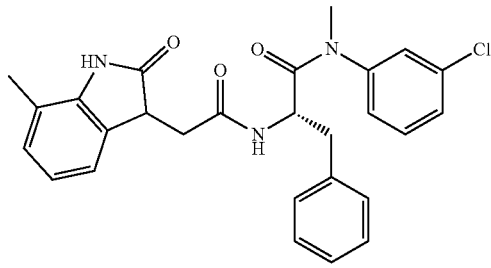 [SMILES: Cc1cccc2c1NC(=O)C2CC(=O)N[C@@H](Cc1ccccc1)C(=O)N(C)c1cccc(Cl)c1]

Using the general procedure described above, the title compound was prepared. Yield 72%. $^1$H NMR (600 MHz, CD$_3$OD) δ 7.31-7.24 (m, 6H), 7.01-6.88 (m, 5H), 6.81-6.77 (m, 1H), 6.67 (s, 1H), 4.62-4.55 (m, 1H), 3.76-3.71 (m, 1H), 3.13-3.09 (m, 3H), 2.96-2.84 (m, 2H), 2.73-2.69 (m, 1H), 2.55-2.51 (m, 1H), 2.23 (s, 3H); $^{13}$C NMR (100 MHz, CD$_3$OD) δ 181.75, 173.0, 172.9, 172.3, 172.0, 145.2, 145.0, 142.1, 142.0, 137.9, 135.9, 131.8, 130.5, 130.3, 130.1, 130.0, 129.7, 129.6, 129.4, 128.8, 128.1, 127.24, 123.4, 123.3, 122.9, 122.7, 122.6, 120.5, 53.6, 53.1, 44.3, 39.8, 39.7, 38.0, 37.8, 37.1, 36.9, 16.7; HRMS-ESI (−) m/z calcd for C$_{27}$H$_{25}$ClN$_3$O$_3$ [M−H]$^-$ 474.1590, found 474.1594.

Example 4. Preparation of (2S)—N-(3-fluorophenyl)-N-methyl-2-(2-(7-methyl-2-oxoindolin-3-yl)acetamido)-3-phenylpropanamide (4)

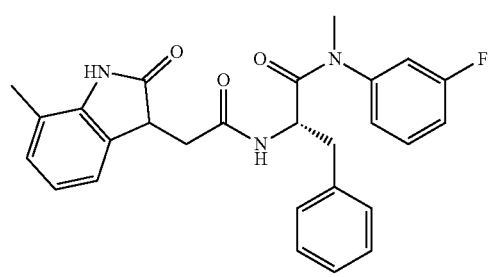 [SMILES: Cc1cccc2c1NC(=O)C2CC(=O)N[C@@H](Cc1ccccc1)C(=O)N(C)c1cccc(F)c1]

Using the general procedure described above, the title compound was prepared. Yield 69%. $^1$H NMR (600 MHz, CD$_3$OD) δ 7.34-7.22 (m, 4H), 7.08-7.05 (m, 1H), 7.00-6.87 (m, 5H), 6.79-6.73 (m, 2H), 6.57 (s, 1H), 4.67-4.59 (m, 1H), 3.75-3.70 (m, 1H), 3.15-3.11 (m, 3H), 2.97-2.82 (m, 2H), 2.73-2.68 (m, 1H), 2.55-2.50 (m, 1H), 2.22 (s, 3H); HRMS-ESI (−) m/z calcd for C$_{27}$H$_{25}$FN$_3$O$_3$ [M−H]$^-$ 458.1885, found 458.1890.

Example 5. Preparation of (2S)-2-(2-(4,7-dimethyl-2-oxoindolin-3-yl)acetamido)-N-methyl-N,3-diphenylpropanamide (5)

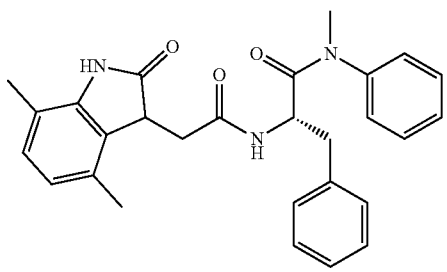 [SMILES: Cc1ccc(C)c2c1NC(=O)C2CC(=O)N[C@@H](Cc1ccccc1)C(=O)N(C)c1ccccc1]

Using the general procedure described above, the title compound was prepared. Yield 58%. $^1$H NMR (600 MHz, CD$_3$OD) δ 7.30-7.24 (m, 2H), 7.20-7.14 (m, 4H), 6.92-6.82 (m, 3H), 6.69-6.62 (m, 1H), 6.45 (s, 1H), 4.58-4.52 (m, 1H), 3.68-3.67 (m, 1H), 3.14-3.06 (m, 3H), 3.01-2.81 (m, 3H), 2.65-2.59 (m, 1H), 2.23-2.16 (m, 6H); $^{13}$C NMR (100 MHz, CD$_3$OD) δ 182.1, 182.0, 173.1, 172.9, 171.8, 171.3, 143.9, 143.6, 142.5, 142.2, 138.1, 133.1, 132.8, 130.8, 130.6, 130.5, 130.4, 130.3, 130.2, 129.4, 129.2, 129.1, 128.5, 127.8, 125.0, 124.9, 117.9, 117.8, 53.1, 52.6, 39.8, 39.5, 38.0, 37.8, 36.1, 36.0, 18.6, 16.4; HRMS-ESI (−) m/z calcd for C$_{24}$H$_{28}$N$_3$O$_3$ [M−H]$^-$ 454.2136, found 454.2145.

Example 6. Preparation of (2S)-2-(2-(4,7-dimethyl-2-oxoindolin-3-yl)acetamido)-N-(4-fluorophenyl)-N-methyl-3-phenylpropanamide (6)

Using the general procedure described above, the title compound was prepared. Yield 65%. $^1$H NMR (600 MHz, CD$_3$OD) δ 8.27-8.14 (m, 1H), 7.31-7.18 (m, 3H), 6.99-6.82 (m, 6H), 6.70-6.64 (m, 1H), 6.31 (s, 1H), 4.53-4.46 (m, 1H), 3.69-3.65 (m, 1H), 3.10-3.01 (m, 3H), 2.99-2.85 (m, 3H), 2.65-2.61 (m, 1H), 2.23-2.17 (m, 6H); HRMS-ESI (−) m/z calcd for C$_{28}$H$_{27}$FN$_3$O$_3$ [M−H]$^-$ 472.2042, found 472.2047.

Example 7. Preparation of (2S)-2-(2-(4,7-dimethyl-2-oxoindolin-3-yl)acetamido)-N-(3-fluorophenyl)-N-methyl-3-phenylpropanamide (7)

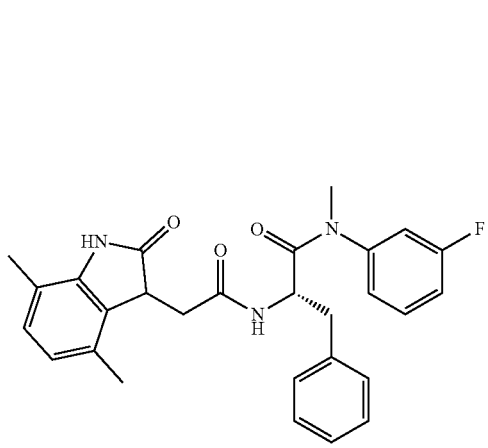 [SMILES: Cc1ccc(C)c2c1NC(=O)C2CC(=O)N[C@@H](Cc1ccccc1)C(=O)N(C)c1cccc(F)c1]

Using the general procedure described above, the title compound was prepared. Yield 68%. $^1$H NMR (600 MHz, CD$_3$OD) δ 7.28-7.11 (m, 4H), 7.05-6.86 (m, 4H), 6.69-6.41 (m, 2H), 6.19-6.04 (m, 1H), 4.56-4.50 (m, 1H), 3.70-3.65 (m, 1H), 3.11-3.02 (m, 3H), 3.00-2.85 (m, 3H), 2.67-2.64 (m, 1H), 2.21-2.17 (m, 6H); HRMS-ESI (−) m/z calcd for C$_{28}$H$_{27}$FN$_3$O$_3$ [M−H]$^-$ 472.2042, found 472.2046.

Example 8. Preparation of (2S)—N-(4-chlorophenyl)-2-(2-(4,7-dimethyl-2-oxoindolin-3-yl)acetamido)-N-methyl-3-phenylpropanamide (8)

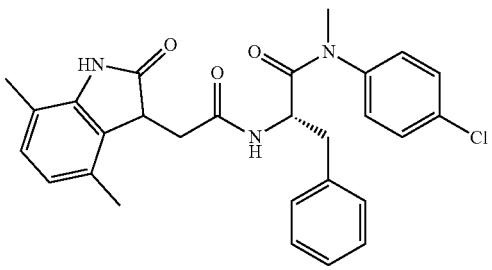 [SMILES: Cc1ccc(C)c2c1NC(=O)C2CC(=O)N[C@@H](Cc1ccccc1)C(=O)N(C)c1ccc(Cl)cc1]

Using the general procedure described above, the title compound was prepared. Yield 72%. $^1$H NMR (600 MHz, CD$_3$OD) δ 7.24-7.18 (m, 4H), 7.08 (d, J=8.6 Hz, 1H), 6.92-6.85 (m, 3H), 6.70-6.63 (m, 2H), 6.23 (s, 1H), 4.51-4.45 (m, 1H), 3.68-3.63 (m, 1H), 3.09-2.99 (m, 3H), 2.91-2.84 (m, 3H), 2.65-2.60 (m, 1H), 2.23-2.16 (m, 6H); $^{13}$C NMR (100 MHz, CD$_3$OD) δ 182.1, 181.9, 173.0, 172.7, 171.8, 171.1, 142.7, 142.5, 142.2, 138.0, 134.9, 134.7, 133.0, 132.8, 130.7, 130.6, 130.5, 130.4, 130.3, 130.1, 129.5, 127.9, 127.8, 127.7, 125.0, 124.9, 117.9, 117.8, 53.0, 52.4, 44.2, 44.1, 39.9, 39.6, 37.9, 37.6, 36.0, 18.6, 16.4; HRMS-ESI (−) m/z calcd for C$_{28}$H$_{27}$ClN$_3$O$_3$ [M−H]$^-$ 488.1746, found 488.1750.

Example 9. Preparation of (2S)—N-(3-chlorophenyl)-2-(2-(4,7-dimethyl-2-oxoindolin-3-yl)acetamido)-N-methyl-3-phenylpropanamide (9)

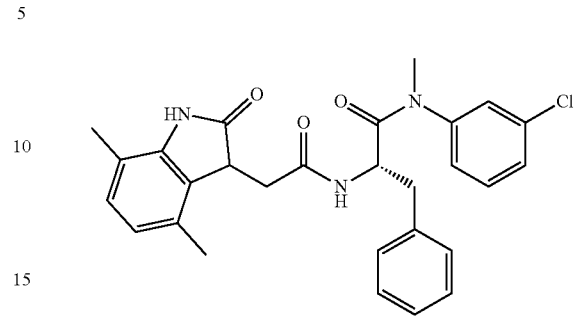

Using the general procedure described above, the title compound was prepared. Yield 79%. $^1$H NMR (600 MHz, CD$_3$OD) δ 7.27-7.07 (m, 6H), 6.91-6.85 (m, 3H), 6.68-6.63 (m, 1H), 6.29 (s, 1H), 4.51-4.46 (m, 1H), 3.70-3.65 (m, 1H), 3.07-2.99 (m, 3H), 2.96-2.84 (m, 3H), 2.66-2.63 (m, 1H), 2.21-2.16 (m, 6H); $^{13}$C NMR (100 MHz, CD$_3$OD) δ 182.0, 181.9, 172.9, 172.7, 171.8, 171.3, 145.0, 144.7, 142.5, 142.1, 137.9, 137.8, 135.8, 135.6, 133.0, 132.8, 131.8, 131.6, 130.5, 130.3, 129.6, 129.3, 128.6, 128.0, 127.8, 127.2, 127.1, 125.0, 124.9, 117.9, 117.8, 53.1, 52.6, 44.2, 39.8, 37.9, 37.7, 36.1, 18.6, 16.5; HRMS-ESI (−) m/z calcd for C$_{28}$H$_{27}$ClN$_3$O$_3$ [M−H]$^-$ 488.1746, found 488.1751.

Example 10. Preparation of (S)—N-methyl-2-(2-(naphthalen-2-yl)acetamido)-N,3-diphenylpropanamide (10)

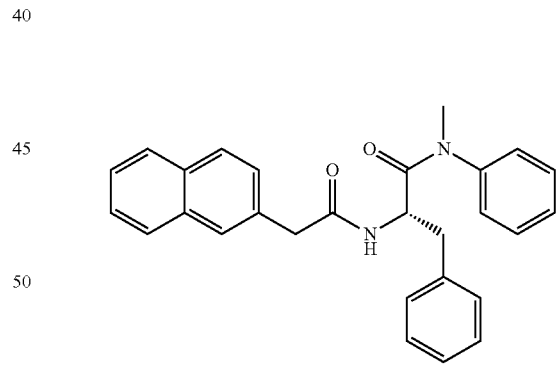

Using the general procedure described above, the title compound was prepared. Yield 79%. $^1$H NMR (600 MHz, CD$_3$OD) δ 8.26 (d, J=7.5 Hz, 1H), 7.81-7.74 (m, 3H), 7.64 (s, 1H), 7.46-7.42 (m, 2H), 7.35-7.34 (m, 3H), 7.28-7.27 (m, 1H), 7.15-7.03 (m, 4H), 6.81 (d, J=7.2 Hz, 2H), 4.69-4.65 (m, 1H), 3.66-3.61 (m, 2H), 3.19 (s, 3H), 2.95 (dd, J=13.4, 6.4 Hz, 1H), 2.72 (dd, J=13.4, 8.4 Hz, 1H); $^{13}$C NMR (150 MHz, CD$_3$OD) δ 173.4, 173.3, 144.0, 138.1, 135.0, 134.2, 133.9, 130.9, 130.1, 129.4, 129.4, 129.1, 128.8, 128.7, 128.6, 128.6, 128.3, 127.8, 127.1, 126.7, 53.6, 43.5, 39.0, 38.1; HRMS-ESI (−) m/z calcd for C$_{28}$H$_{25}$N$_2$O$_2$ [M−H]$^-$ 421.1922, found 421.1927.

Example 11. Preparation of (S)—N-methyl-2-(2-(naphthalen-2-yl)acetamido)-3-phenyl-N-(p-tolyl)propanamide (11)

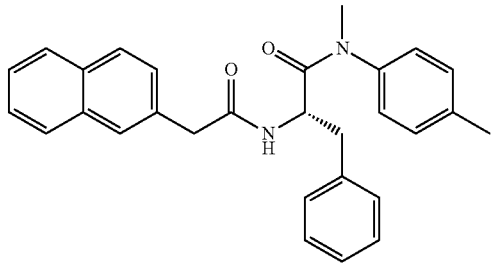 [SMILES: Cc1ccc(N(C)C(=O)[C@H](Cc2ccccc2)NC(=O)Cc2ccc3ccccc3c2)cc1]

Using the general procedure described above, the title compound was prepared. Yield 58%. $^1$H NMR (600 MHz, CDCl$_3$) δ 7.83-7.77 (m, 3H), 7.63 (s, 1H), 7.49-7.45 (m, 2H), 7.28-7.26 (m, 1H), 7.14-7.05 (m, 5H), 6.79-6.75 (m, 4H), 6.17 (d, J=8.2 Hz, 1H), 4.84-4.80 (m, 1H), 3.67-3.62 (m, 2H), 3.17 (s, 3H), 2.81 (dd, J=13.4, 6.9 Hz, 1H), 2.62 (dd, J=13.4, 7.1 Hz, 1H), 2.35 (s, 3H); $^{13}$C NMR (100 MHz, CDCl$_3$) δ 171.4, 170.0, 139.9, 138.1, 136.1, 133.6, 132.5, 132.2, 130.4, 129.2, 128.6, 128.3, 128.1, 127.7, 127.7, 127.3, 127.0, 126.7, 126.2, 125.9, 51.0, 43.8, 38.8, 37.7, 21.1; HRMS-ESI (−) m/z calcd for C$_{29}$H$_{27}$N$_2$O$_2$ [M−H]$^-$ 435.2079, found 435.2083.

Example 12. Preparation of (S)—N-(4-chlorophenyl)-N-methyl-2-(2-(naphthalen-2-yl)acetamido)-3-phenylpropanamide (12)

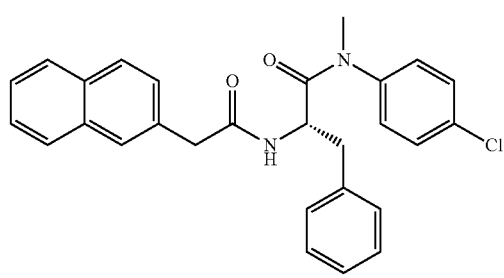 [SMILES: CN(C(=O)[C@H](Cc1ccccc1)NC(=O)Cc1ccc2ccccc2c1)c1ccc(Cl)cc1]

Using the general procedure described above, the title compound was prepared. Yield 70%. $^1$H NMR (600 MHz, CD$_3$OD) δ 7.80-7.74 (m, 3H), 7.65 (s, 1H), 7.45-7.41 (m, 2H), 7.30-7.26 (m, 3H), 7.18-7.13 (m, 3H), 6.88-6.87 (m, 4H), 4.59 (t, J=7.5 Hz, 1H), 3.65-3.61 (m, 2H), 3.12 (s, 3H), 2.95 (dd, J=13.3, 7.5 Hz, 1H), 2.74 (dd, J=13.3, 7.5 Hz, 1H); $^{13}$C NMR (100 MHz, CD$_3$OD) δ 173.3, 173.2, 142.6, 137.9, 135.0, 134.2, 133.9, 130.8, 130.3, 129.5, 129.1, 128.8, 128.7, 128.6, 128.3, 128.0, 127.1, 126.7, 53.5, 43.4, 39.2, 38.0; HRMS-ESI (−) m/z calcd for C$_{28}$H$_{24}$ClN$_2$O$_2$ [M−H]$^-$ 455.1532, found 455.1531.

Example 13. Preparation of (S)—N-(3-chlorophenyl)-N-methyl-2-(2-(naphthalen-2-yl)acetamido)-3-phenylpropanamide (13)

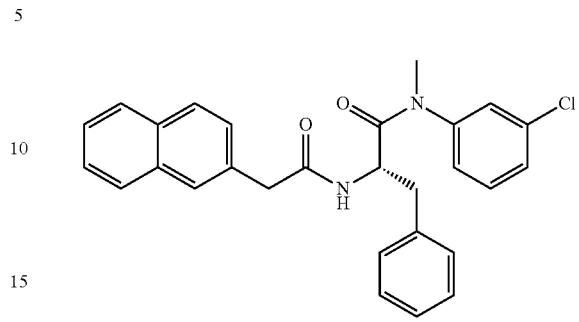

Using the general procedure described above, the title compound was prepared. Yield 90%. $^1$H NMR (600 MHz, CD$_3$OD) δ 7.79-7.74 (m, 3H), 7.67 (s, 1H), 7.44-7.40 (m, 2H), 7.32-7.24 (m, 3H), 7.19-7.13 (m, 3H), 6.93-6.76 (m, 4H), 4.58 (t, J=7.4 Hz, 1H), 3.64 (s, 2H), 3.11 (s, 3H), 2.95 (dd, J=13.1, 7.9 Hz, 1H), 2.75 (dd, J=13.1, 7.3 Hz, 1H); $^{13}$C NMR (100 MHz, CD$_3$OD) δ 173.4, 173.1, 145.1, 137.8, 135.9, 135.0, 134.2, 133.9, 131.9, 130.2, 129.6, 129.4, 129.1, 128.8, 128.7, 128.7, 128.6, 128.3, 128.1, 127.2, 127.1, 126.7, 53.6, 43.4, 39.4, 38.0; HRMS-ESI (−) m/z calcd for C$_{28}$H$_{24}$ClN$_2$O$_2$ [M−H]$^-$ 455.1532, found 455.1533.

Example 14. Preparation of (S)—N-(3-fluorophenyl)-N-methyl-2-(2-(naphthalen-2-yl)acetamido)-3-phenylpropanamide (14)

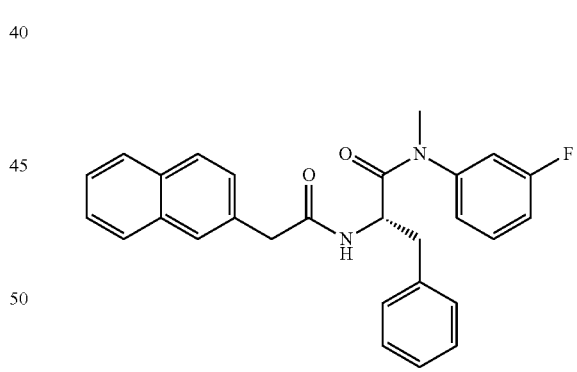

Using the general procedure described above, the title compound was prepared. Yield 79%. $^1$H NMR (600 MHz, CD$_3$OD) δ 7.79-7.73 (m, 3H), 7.66 (s, 1H), 7.44-7.40 (m, 2H), 7.31-7.27 (m, 2H), 7.17-7.11 (m, 3H), 7.06 (t, J=7.9 Hz, 1H), 6.87-6.81 (m, 3H), 6.62 (s, 1H), 4.63 (t, J=7.4 Hz, 1H), 3.66-3.61 (m, 2H), 3.13 (s, 3H), 2.95 (dd, J=13.2, 7.5 Hz, 1H), 2.74 (dd, J=13.2, 7.6 Hz, 1H); $^{13}$C NMR (100 MHz, CD$_3$OD) δ 173.4, 173.2, 164.2 (d, $J_{CF}$=247.4 Hz), 145.4 (d, $J_{CF}$=9.7 Hz), 137.9, 135.0, 134.2, 133.9, 132.1 (d, $J_{CF}$=9.1 Hz), 130.2, 129.5, 129.1, 128.8, 128.7, 128.6, 128.3, 128.0, 127.1, 126.7, 124.7, 116.2 (d, $J_{CF}$=21.3 Hz), 115.9 (d, $J_{CF}$=23.1 Hz), 53.6, 43.4, 39.3, 38.0; HRMS-ESI (−) m/z calcd for C$_{28}$H$_{24}$FN$_2$O$_2$ [M−H]$^-$ 439.1827, found 439.1830.

Example 15. Preparation of (S)—N-ethyl-2-(2-(naphthalen-2-yl)acetamido)-N,3-diphenylpropanamide (15)

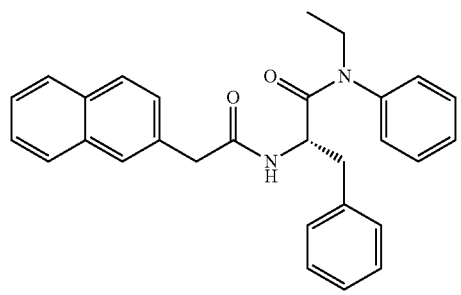 [SMILES: CCN(C(=O)[C@H](Cc1ccccc1)NC(=O)Cc1ccc2ccccc2c1)c1ccccc1]

Using the general procedure described above, the title compound was prepared. Yield 80%. ¹H NMR (600 MHz, CDCl₃) δ 7.83-7.78 (m, 3H), 7.64 (s, 1H), 7.50-7.45 (m, 2H), 7.36-7.34 (m, 3H), 7.27-7.26 (m, 1H), 7.14 (t, J=7.4 Hz, 1H), 7.06 (t, J=7.6 Hz, 2H), 6.91-6.86 (m, 1H), 6.73 (d, J=7.3 Hz, 2H), 6.08 (d, J=8.1 Hz, 1H), 4.72-4.68 (m, 1H), 3.81-3.75 (m, 1H), 3.67-3.62 (m, 2H), 3.59-3.53 (m, 1H), 2.82 (dd, J=13.4, 6.9 Hz, 1H), 2.60 (dd, J=13.4, 7.1 Hz, 1H), 1.06 (t, J=7.2 Hz, 3H); ¹³C NMR (100 MHz, CDCl₃) δ 170.7, 169.9, 140.8, 136.1, 133.6, 132.5, 132.2, 129.7, 129.3, 128.6, 128.4, 128.3, 128.1, 127.7, 127.7, 127.3, 126.8, 126.2, 125.9, 51.4, 44.6, 43.8, 38.8, 12.8; HRMS-ESI (−) m/z calcd for $C_{29}H_{27}N_2O_2$ [M−H]⁻ 435.2079, found 435.2081.

Example 16. Preparation of (S)—N-ethyl-2-(2-(naphthalen-2-yl)acetamido)-N,3-diphenylpropanamide (16)

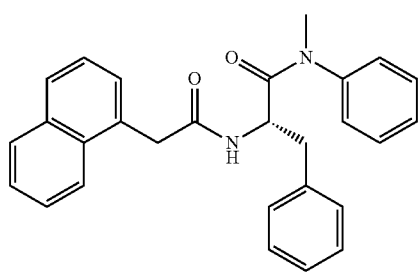 [SMILES: CN(C(=O)[C@H](Cc1ccccc1)NC(=O)Cc1cccc2ccccc12)c1ccccc1]

Using the general procedure described above, the title compound was prepared. (S)—N-methyl-2-(2-(naphthalen-1-yl)acetamido)-N,3-diphenylpropanamide (31). Yield 70%. ¹H NMR (600 MHz, CD₃OD) δ 7.86-7.83 (m, 2H), 7.76 (d, J=8.2 Hz, 1H), 7.46-7.42 (m, 2H), 7.39-7.36 (m, 1H), 7.33-7.29 (m, 4H), 7.17-7.10 (m, 3H), 7.00 (m, 2H), 6.77 (d, J=7.3 Hz, 2H), 4.68-4.66 (m, 1H), 3.94 (s, 2H), 3.17 (s, 3H), 2.92 (dd, J=13.4, 6.3 Hz, 1H), 2.70 (dd, J=13.4, 8.4 Hz, 2H); ¹³C NMR (150 MHz, CD₃OD) δ 173.3, 173.2, 143.9, 138.0, 135.3, 133.5, 132.8, 130.8, 130.1, 129.6, 129.4, 129.3, 129.0, 128.8, 128.6, 127.8, 127.3, 126.7, 126.5, 124.9, 53.5, 40.9, 39.0, 38.1; HRMS-ESI (−) m/z calcd for $C_{28}H_{25}N_2O_2$ [M−H]⁻ 421.1922, found 421.1928.

Example 17. Preparation of (S)—N-methyl-2-(2-(naphthalen-1-yl)acetamido)-3-phenyl-N-(p-tolyl)propanamide (17)

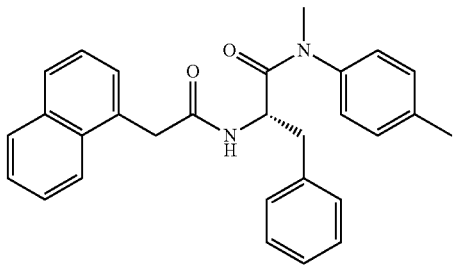 [SMILES: Cc1ccc(N(C)C(=O)[C@H](Cc2ccccc2)NC(=O)Cc2cccc3ccccc23)cc1]

Using the general procedure described above, the title compound was prepared. Yield 69%. ¹H NMR (600 MHz, CDCl₃) δ 7.87-7.85 (m, 2H), 7.80 (d, J=8.2 Hz, 1H), 7.50-7.41 (m, 3H), 7.35 (d, J=6.9 Hz, 1H), 7.13-7.08 (m, 3H), 7.01 (t, J=7.6 Hz, 2H), 6.75 (s, 1H), 6.60 (d, J=7.4 Hz, 2H), 6.08 (d, J=8.3 Hz, 1H), 4.82-4.78 (m, 1H), 3.99-3.90 (m, 2H), 3.12 (s, 3H), 2.68 (dd, J=13.3, 6.9 Hz, 1H), 2.51 (dd, J=13.4, 7.0 Hz, 1H), 2.35 (s, 3H); ¹³C NMR (100 MHz, CDCl₃) δ 171.2, 169.9, 139.8, 138.1, 136.0, 133.9, 132.1, 131.0, 130.4, 129.1, 128.7, 128.3, 128.2, 128.2, 127.0, 126.6, 126.5, 126.0, 125.7, 123.8, 51.0, 41.6, 38.7, 37.6, 21.1; HRMS-ESI (−) m/z calcd for $C_{29}H_{27}N_2O_2$ [M−H]⁻ 435.2079, found 435.2085.

Example 18. Preparation of (S)—N-(4-chlorophenyl)-N-methyl-2-(2-(naphthalen-1-yl)acetamido)-3-phenylpropanamide (18)

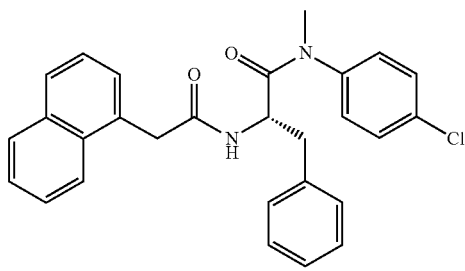 [SMILES: CN(C(=O)[C@H](Cc1ccccc1)NC(=O)Cc1cccc2ccccc12)c1ccc(Cl)cc1]

Using the general procedure described above, the title compound was prepared. Yield 80%. ¹H NMR (600 MHz, CD₃OD) δ 7.90-7.84 (m, 2H), 7.77 (d, J=8.2 Hz, 1H), 7.46-7.45 (m, 2H), 7.40-7.37 (m, 1H), 7.32 (d, J=6.9 Hz, 1H), 7.25-7.15 (m, 5H), 6.86-6.85 (m, 4H), 4.59 (t, J=7.5 Hz, 1H), 3.98-3.93 (m, 2H), 3.12 (s, 3H), 2.93 (dd, J=13.3, 7.4 Hz, 1H), 2.74 (dd, J=13.3, 7.6 Hz, 1H); ¹³C NMR (100 MHz, CD₃OD) δ 173.3, 173.2, 142.6, 138.0, 135.4, 135.0, 133.6, 132.8, 130.8, 130.3, 130.2, 129.7, 129.6, 129.1, 128.9, 128.0, 127.3, 126.8, 126.6, 124.9, 53.5, 40.8, 39.2, 38.0; HRMS-ESI (−) m/z calcd for $C_{28}H_{24}ClN_2O_2$ [M−H]⁻ 455.1532, found 455.1534.

Example 19. Preparation of (S)—N-(3-chlorophenyl)-N-methyl-2-(2-(naphthalen-1-yl)acetamido)-3-phenylpropanamide (19)

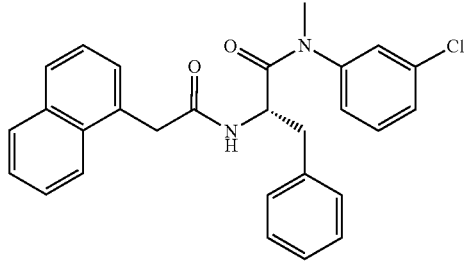 [SMILES: CN(C(=O)[C@H](Cc1ccccc1)NC(=O)Cc1cccc2ccccc12)c1cccc(Cl)c1]

Using the general procedure described above, the title compound was prepared. Yield 82%. $^1$H NMR (600 MHz, CD$_3$OD) δ 7.91-7.90 (m, 1H), 7.85-7.83 (m, 1H), 7.76 (d, J=8.2 Hz, 1H), 7.47-7.44 (m, 2H), 7.40-7.16 (m, 8H), 6.91-6.85 (m, 3H), 4.60-4.57 (m, 1H), 3.99-3.93 (m, 2H), 3.11 (s, 3H), 2.93 (dd, J=13.1, 7.8 Hz, 1H), 2.74 (dd, J=13.1, 7.3 Hz, 1H); $^{13}$C NMR (100 MHz, CD$_3$OD) δ 173.3, 173.1, 145.1, 137.8, 135.9, 135.3, 133.6, 132.8, 131.9, 130.2, 129.7, 129.6, 129.4, 129.0, 128.9, 128.7, 128.1, 127.3, 127.2, 126.8, 126.6, 124.9, 53.6, 40.8, 39.3, 38.0; HRMS-ESI (−) m/z calcd for C$_{28}$H$_{24}$ClN$_2$O$_2$ [M−H]$^-$ 455.1532, found 455.1535.

Example 20. Preparation of (S)—N-(3-fluorophenyl)-N-methyl-2-(2-(naphthalen-1-yl)acetamido)-3-phenylpropanamide (20)

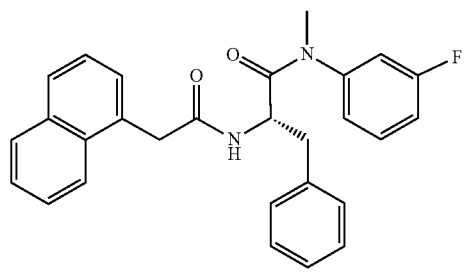 [SMILES: CN(C(=O)[C@H](Cc1ccccc1)NC(=O)Cc1cccc2ccccc12)c1cccc(F)c1]

Using the general procedure described above, the title compound was prepared. Yield 65%. $^1$H NMR (600 MHz, CD$_3$OD) δ 8.23 (d, J=6.7 Hz, 1H), 7.90-7.76 (m, 3H), 7.46-7.26 (m, 6H), 7.20-7.14 (m, 3H), 7.05 (t, J=7.8 Hz, 1H), 6.85-6.80 (m, 3H), 6.61 (s, 1H), 4.66-4.63 (m, 1H), 3.96 (s, 2H), 3.13 (s, 3H), 2.94 (dd, J=13.2, 7.3 Hz, 1H), 2.74 (dd, J=13.1, 7.7 Hz, 1H); $^{13}$C NMR (100 MHz, CD$_3$OD) δ 173.4, 173.1, 164.2 (d, J=247.5 Hz), 145.4 (d, J=9.5 Hz), 137.9, 135.3, 133.6, 132.7, 132.1 (d, J=9.2 Hz), 130.2, 129.7, 129.5, 129.0, 128.8, 128.0, 127.3, 126.8, 126.5, 124.9, 124.7, 116.2 (d, J=21.1 Hz), 115.9 (d, J=22.7 Hz), 53.5, 40.8, 39.2, 37.9; HRMS-ESI (−) m/z calcd for C$_{28}$H$_{24}$FN$_2$O$_2$ [M−H]$^-$ 439.1827, found 439.1831.

Example 21. Preparation of (S)—N-ethyl-2-(2-(naphthalen-1-yl)acetamido)-N,3-diphenylpropanamide (21)

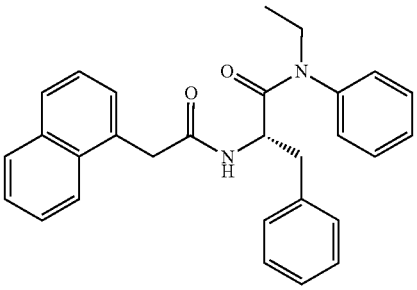 [SMILES: CCN(C(=O)[C@H](Cc1ccccc1)NC(=O)Cc1cccc2ccccc12)c1ccccc1]

Using the general procedure described above, the title compound was prepared. Yield 69%. $^1$H NMR (600 MHz, CDCl$_3$) δ 7.87-7.85 (m, 2H), 7.80 (d, J=8.2 Hz, 1H), 7.50-7.41 (m, 3H), 7.36-7.32 (m, 4H), 7.09 (t, J=7.4 Hz, 1H), 7.02-6.99 (m, 2H), 6.83 (s, 1H), 6.60 (d, J=7.4 Hz, 2H), 6.07 (d, J=8.3 Hz, 1H), 4.70-4.66 (m, 1H), 3.99-3.90 (m, 2H), 3.74-3.71 (m, 1H), 3.53-3.47 (m, 1H), 2.69 (dd, J=13.3, 6.9 Hz, 1H), 2.50 (dd, J=13.3, 7.0 Hz, 1H), 1.01 (t, J=7.2 Hz, 3H); $^{13}$C NMR (100 MHz, CDCl$_3$) δ 170.5, 169.9, 140.7, 136.0, 133.9, 132.1, 131.0, 129.7, 129.2, 128.7, 128.4, 128.3, 128.2, 128.2, 126.6, 126.5, 126.0, 125.7, 123.8, 51.3, 44.6, 41.6, 38.8, 12.7; HRMS-ESI (−) m/z calcd for C$_{29}$H$_{27}$N$_2$O$_2$ [M−H]$^-$ 435.2079, found 435.2083.

Example 22. Preparation of 2-(2-(2,4-dioxo-1,3-diazaspiro[4.5]decan-3-yl)acetamido)-N-methyl-N,3-diphenylpropanamide

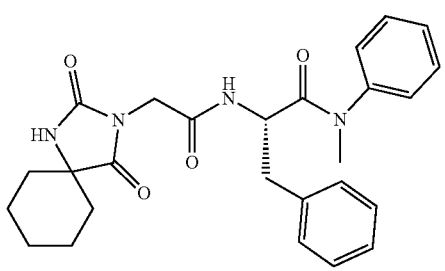 [SMILES: CN(C(=O)[C@H](Cc1ccccc1)NC(=O)CN1C(=O)NC2(CCCCC2)C1=O)c1ccccc1]

Using the general procedure described above, the title compound was prepared. $^1$H NMR (600 MHz, DMSO-d6) δ 8.65 (s, 1H), 8.53 (d, J=7.8 Hz, 1H), 7.45-7.32 (m, 3H), 7.20-7.12 (m, 4H), 6.82-6.77 (m, 2H), 4.42-4.38 (m, 1H), 3.95-3.82 (m, 2H), 3.13 (s, 3H), 2.81 (dd, J=13.2, 6.2 Hz, 1H), 2.61 (dd, J=13.5, 9.2 Hz, 1H), 1.64-1.59 (m, 4H), 1.57-1.45 (m, 5H), 1.29-1.24 (m, 1H); $^{13}$C NMR (151 MHz, DMSO-d6) δ 176.9, 171.0, 166.1, 155.8, 143.1, 137.7, 130.0, 129.2, 129.2, 128.6, 128.3, 127.9, 126.9, 61.5, 52.1, 37.8, 37.6, 33.7, 24.8, 21.2; HRMS (ESI) m/z calcd for C$_{26}$H$_{31}$N$_4$O$_4$ [M+H]$^+$ 463.2340, found 463.2337.

Example 23. Preparation of 2-(2-(2,4-dioxo-1,3-diazaspiro[4.5]decan-3-yl)acetamido)-N-(4-methoxyphenyl)-N-methyl-3-phenylpropanamide

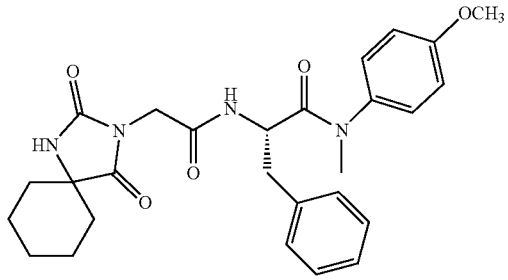 [SMILES: COc1ccc(N(C)C(=O)[C@H](Cc2ccccc2)NC(=O)CN2C(=O)NC3(CCCCC3)C2=O)cc1]

Using the general procedure described above, the title compound was prepared. $^1$H NMR (600 MHz, DMSO-d6) δ 8.65 (s, 1H), 8.50 (d, J=7.9 Hz, 1H), 7.20-7.14 (m, 3H), 7.07-6.99 (m, 2H), 6.93 (d, J=8.3 Hz, 2H), 6.84 (d, J=7.0 Hz, 2H), 4.41-4.35 (m, 1H), 3.95-3.79 (m, 2H), 3.76 (s, 3H), 3.08 (s, 3H), 2.83 (dd, J=13.5, 5.3 Hz, 1H), 2.61 (dd, J=13.4, 8.8 Hz, 1H), 1.64-1.58 (m, 4H), 1.54-1.42 (m, 5H), 1.30-1.23 (m, 1H); $^{13}$C NMR (151 MHz, DMSO-d6) δ 176.9, 171.2, 166.0, 158.9, 155.8, 137.7, 135.8, 129.5, 129.1, 128.8, 128.4, 127.1, 115.3, 114.9, 61.5, 55.9, 55.7, 52.0, 51.8, 37.9, 33.7, 24.9, 21.2; HRMS (ESI) m/z calcd for $C_{27}H_{33}N_4O_5$ [M+H]+ 493.2445, found 493.2449.

Example 24. Preparation of 2-(2-(2,4-dioxo-1,3-diazaspiro[4.5]decan-3-yl)acetamido)-N-methyl-3-phenyl-N-(p-tolyl)propenamide

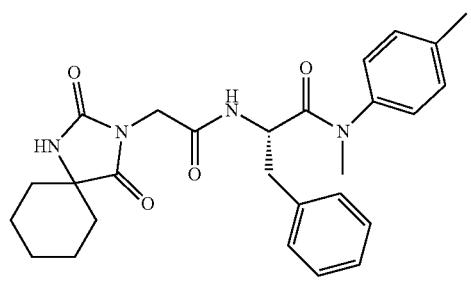 [SMILES: Cc1ccc(N(C)C(=O)[C@H](Cc2ccccc2)NC(=O)CN2C(=O)NC3(CCCCC3)C2=O)cc1]

Using the general procedure described above, the title compound was prepared. $^1$H NMR (600 MHz, DMSO-d6) δ 8.65 (s, 1H), 8.50 (d, J=7.9 Hz, 1H), 7.20-7.15 (m, 4H), 6.98 (d, J=7.1 Hz, 2H), 6.85-6.80 (m, 2H), 4.44-4.39 (m, 1H), 3.96-3.82 (m, 2H), 3.09 (s, 3H), 2.82 (dd, J=12.5, 7.4 Hz, 1H), 2.61 (dd, J=13.2, 8.9 Hz, 1H), 2.31 (s, 3H), 1.66-1.59 (m, 4H), 1.54-1.44 (m, 5H), 1.31-1.24 (m, 1H); $^{13}$C NMR (151 MHz, DMSO-d6) δ 176.9, 171.0, 166.0, 155.8, 140.6, 137.7, 137.7, 130.5, 129.7, 129.3, 128.6, 127.6, 126.9, 61.5, 51.9, 38.0, 37.6, 33.7, 24.8, 21.2, 21.1; HRMS (ESI) m/z calcd for $C_{27}H_{33}N_4O_4$ [M+H]+ 477.2496, found 477.2494.

Example 25. Preparation of 2-(2-(2,4-dioxo-1,3-diazaspiro[4.5]decan-3-yl)acetamido)-N-(4-fluorophenyl)-N-methyl-3-phenylpropanamide

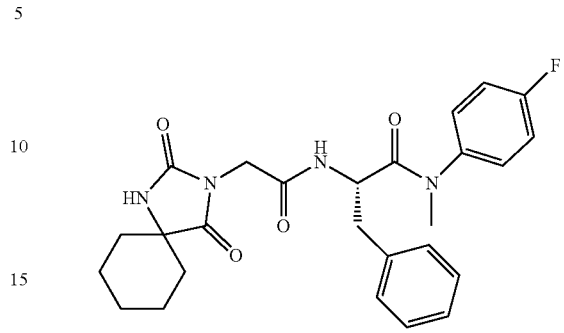

Using the general procedure described above, the title compound was prepared. Yield 69%. $^1$H NMR (600 MHz, CD3OD) δ 7.32-7.23 (m, 5H), 7.03-7.00 (m, 2H), 6.98-6.96 (m, 2H), 4.60-4.58 (m, 1H), 4.16-4.04 (m, 2H), 3.13 (s, 3H), 2.97 (dd, J=13.1, 8.4 Hz, 1H), 2.75 (dd, J=13.1, 6.6 Hz, 1H), 1.83-1.77 (m, 4H), 1.66-1.63 (m, 3H), 1.58-1.53 (m, 2H), 1.43-1.37 (m, 1H); $^{13}$C NMR (150 MHz, CD3OD) δ 172.9, 168.0, 163.3 (d, J=246.8 Hz), 157.7, 139.9, 139.9, 137.9, 130.6 (d, J=7.6 Hz), 130.4, 129.6, 128.0, 117.4 (d, J=23.0 Hz), 63.3, 53.2, 40.9, 39.6, 38.1, 34.6, 25.8, 22.5; HRMS (ESI) m/z calcd for $C_{26}H_{28}FN_4O_4$ [M−H]− 479.2100, found 479.2106.

Example 26. Preparation of 2-(2-(2,4-dioxo-1,3-diazaspiro[4.5]decan-3-yl)acetamido)-N-(3-fluorophenyl)-N-methyl-3-phenylpropanamide (30)

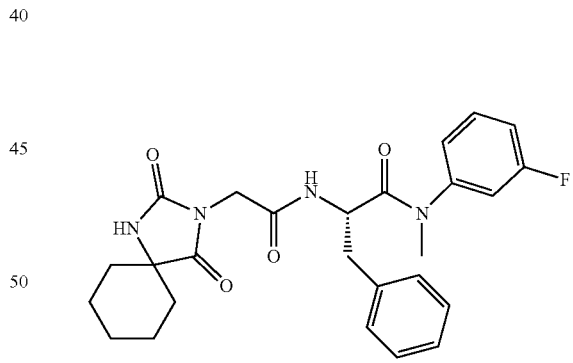

Using the general procedure described above, the title compound was prepared. Yield 70%. $^1$H NMR (600 MHz, CD3OD) δ 7.33-7.23 (m, 5H), 7.06 (t, J=8.3 Hz, 1H), 6.97-6.96 (m, 2H), 6.73 (s, 1H), 6.47 (s, 1H), 4.64-4.61 (m, 1H), 4.17-4.05 (m, 2H), 3.14 (s, 3H), 2.97 (dd, J=13.0, 8.6 Hz, 1H), 2.77 (dd, J=13.1, 6.4 Hz, 1H), 1.84-1.79 (m, 4H), 1.67-1.64 (m, 3H), 1.59-1.52 (m, 2H), 1.43-1.37 (m, 1H); $^{13}$C NMR (150 MHz, CD3OD) δ 178.9, 172.7, 168.1, 164.2 (d, J=247.4 Hz), 157.8, 145.3 (d, J=9.6 Hz), 137.8, 132.1 (d, J=9.1 Hz), 130.4, 129.6, 128.1, 124.6, 116.1 (d, J=21.1 Hz), 115.8 (d, J=22.9 Hz), 63.3, 53.4, 40.9, 39.8, 37.9, 34.6, 25.8, 22.5; HRMS-ESI (−) m/z calcd for $C_{26}H_{28}FN_4O_4$ [M−H]− 479.2100, found 479.2100.

Example 27. Preparation of N-(4-chlorophenyl)-2-(2-(2,4-dioxo-1,3-diazaspiro[4.5]decan-3-yl)acetamido)-N-methyl-3-phenylpropanamide

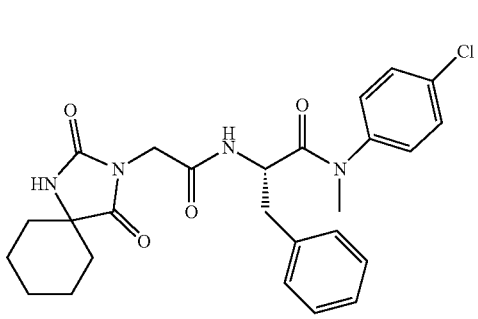 [SMILES: CN(C(=O)[C@H](Cc1ccccc1)NC(=O)CN1C(=O)NC2(CCCCC2)C1=O)c1ccc(Cl)cc1]

Using the general procedure described above, the title compound was prepared. $^1$H NMR (400 MHz, DMSO-d6) δ 8.67 (s, 1H), 8.60 (d, J=7.7 Hz, 1H), 7.45 (d, J=8.5 Hz, 2H), 7.22-7.18 (m, 3H), 7.10 (d, J=8.1 Hz, 2H), 6.91-6.87 (m, 2H), 4.40-4.32 (m, 1H), 3.98-3.82 (m, 2H), 2.90-2.83 (m, 1H), 2.66 (dd, J=13.2, 8.3 Hz, 1H), 1.70-1.60 (m, 4H), 1.56-1.41 (m, 5H), 1.31-1.28 (m, 1H); $^{13}$C NMR (100 MHz, DMSO-d6) δ 177.0, 170.9, 166.2, 155.8, 142.0, 137.5, 132.8, 130.0, 129.8, 129.3, 128.7, 127.1, 61.6, 52.0, 38.0, 37.5, 33.7, 24.8, 21.3; HRMS (ESI) m/z calcd for $C_{26}H_{30}ClN_4O_4$ [M+H]$^+$ 497.1950, found 497.1952.

Example 28. Preparation of N-(3-chlorophenyl)-2-(2-(2,4-dioxo-1,3-diazaspiro[4.5]decan-3-yl)acetamido)-N-methyl-3-phenylpropanamide (31)

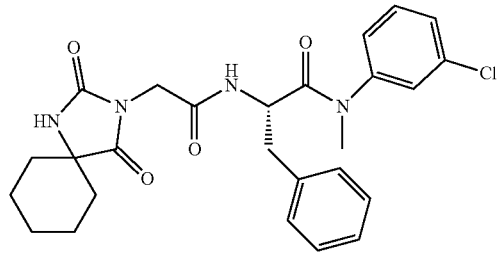 [SMILES: CN(C(=O)[C@H](Cc1ccccc1)NC(=O)CN1C(=O)NC2(CCCCC2)C1=O)c1cccc(Cl)c1]

Using the general procedure described above, the title compound was prepared. Yield 72%. $^1$H NMR (600 MHz, CD$_3$OD) δ 7.32-7.25 (m, 7H), 6.98-6.96 (m, 2H), 4.60-4.58 (m, 1H), 4.17-4.05 (m, 2H), 3.12 (s, 3H), 2.97 (dd, J=13.0, 9.0 Hz, 1H), 2.77 (dd, J=13.0, 6.2 Hz, 1H), 1.84-1.78 (m, 4H), 1.68-1.64 (m, 3H), 1.59-1.53 (m, 2H), 1.44-1.37 (m, 1H); HRMS-ESI (−) m/z calcd for $C_{26}H_{28}ClN_4O_4$ [M−H]$^-$ 495.1805, found 495.1810.

Example 29. Preparation of N-(3-bromophenyl)-2-(2-(2,4-dioxo-1,3-diazaspiro[4.5]decan-3-yl)acetamido)-N-methyl-3-phenylpropanamide (32)

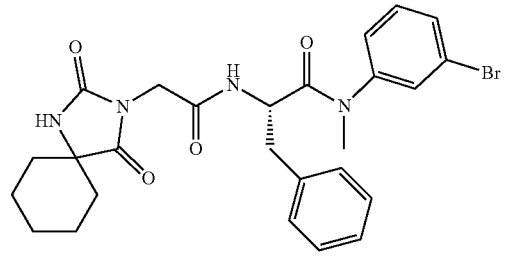 [SMILES: CN(C(=O)[C@H](Cc1ccccc1)NC(=O)CN1C(=O)NC2(CCCCC2)C1=O)c1cccc(Br)c1]

Using the general procedure described above, the title compound was prepared. Yield 68%. $^1$H NMR (600 MHz, DMSO-d6) δ 8.65 (s, 1H), 8.60 (d, J=7.3 Hz, 1H), 7.54 (d, J=7.9 Hz, 1H), 7.33 (t, J=8.0 Hz, 1H), 7.20-7.13 (m, 5H), 6.88-6.87 (m, 2H), 4.34-4.31 (m, 1H), 3.95-3.84 (m, 2H), 3.08 (s, 3H), 2.86 (dd, J=13.4, 5.9 Hz, 1H), 2.66 (dd, J=14.4, 7.2 Hz, 1H), 1.63-1.48 (m, 9H), 1.29-1.23 (m, 1H); $^{13}$C NMR (100 MHz, DMSO-d6) δ 177.0, 171.0, 166.2, 155.8, 144.6, 137.5, 131.7, 131.3, 130.7, 129.3, 128.8, 127.2, 127.1, 122.3, 61.6, 52.2, 38.1, 37.5, 33.7, 24.9, 21.3; HRMS-ESI (−) m/z calcd for $C_{26}H_{28}BrN_4O_4$ [M−H]$^-$ 539.1299, found 539.1297.

Example 30. Preparation of 2-(2-(2,4-dioxo-1,3-diazaspiro[4.5]decan-3-yl)acetamido)-N-ethyl-N,3-diphenylpropanamide

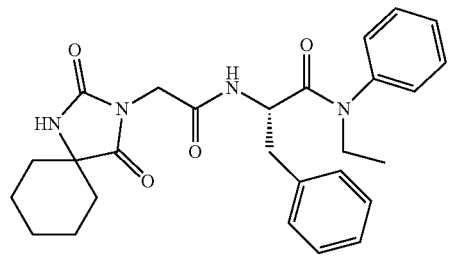 [SMILES: CCN(C(=O)[C@H](Cc1ccccc1)NC(=O)CN1C(=O)NC2(CCCCC2)C1=O)c1ccccc1]

Using the general procedure described above, the title compound was prepared. $^1$H NMR (400 MHz, DMSO-d6) δ 8.65 (s, 1H), 8.49 (d, J=7.9 Hz, 1H), 7.46-7.39 (m, 3H), 7.20-7.16 (m, 3H), 7.08-7.04 (m, 2H), 6.86-6.81 (m, 2H), 4.35-4.28 (m, 1H), 3.98-3.83 (m, 2H), 3.69-3.55 (m, 2H), 2.86 (dd, J=13.4, 5.5 Hz, 1H), 2.62 (dd, J=13.4, 8.5 Hz, 1H), 1.65-1.53 (m, 4H), 1.56-1.45 (m, 5H), 1.34-1.25 (m, 1H), 0.97 (t, J=7.1 Hz, 3H); $^{13}$C NMR (100 MHz, DMSO-d6) δ 170.0, 170.4, 166.0, 155.8, 141.3, 137.7, 130.0, 129.4, 128.9, 128.6, 128.5, 127.0, 61.5, 52.3, 44.2, 38.0, 33.7, 24.9, 21.3, 13.1; HRMS (ESI) m/z calcd for $C_{27}H_{33}N_4O_4$ [M+H]$^+$ 477.2496, found 477.2500.

Example 31. Preparation of (S)-2-(2-(2,4-dioxo-1,4-dihydroquinazolin-3(2H)-yl)acetamido)-N-methyl-N,3-diphenylpropanamide

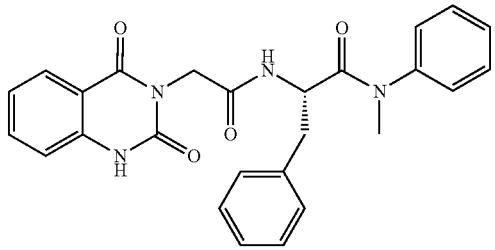 [SMILES: CN(C(=O)[C@H](Cc1ccccc1)NC(=O)Cn1c(=O)[nH]c2ccccc2c1=O)c1ccccc1]

Using the general procedure described above, the title compound was prepared. $^1$H NMR (400 MHz, DMSO-d6) δ 11.45 (s, 1H), 8.63 (d, J=7.5 Hz, 1H), 7.91 (d, J=7.7 Hz, 1H), 7.68 (t, J=7.7 Hz, 1H), 7.41-7.35 (m, 1H), 7.30-7.03 (m, 9H), 6.84-6.81 (m, 2H), 4.56-4.44 (m, 3H), 3.14 (s, 3H), 2.93-2.78 (m, 1H), 2.75-2.58 (m, 1H). $^{13}$C NMR (100 MHz, DMSO-d6) δ 171.2, 166.9, 166.7, 162.1, 153.4, 150.4, 142.6, 137.8, 137.6, 135.6, 133.3, 129.9, 129.3, 128.6, 127.9, 126.1, 123.1, 116.0, 115.6, 112.1, 55.6, 42.4, 42.3, 37.6; HRMS (ESI) m/z calcd for $C_{26}H_{24}N_4O_4$ [M+H]$^+$ 457.187, found 457.1867.

Example 32. Preparation of (S)-2-(2-(2,4-dioxo-1,4-dihydroquinazolin-3(2H)-yl)acetamido)-N-(4-fluorophenyl)-N-methyl-3-phenylpropanamide

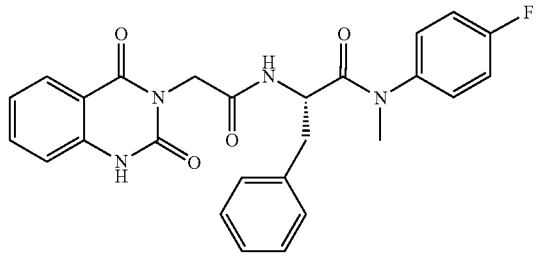 [SMILES: CN(C(=O)[C@H](Cc1ccccc1)NC(=O)Cn1c(=O)[nH]c2ccccc2c1=O)c1ccc(F)cc1]

Using the general procedure described above, the title compound was prepared. $^1$H NMR (400 MHz, DMSO-d6) δ 11.45 (s, 1H), 8.66 (d, J=7.2 Hz, 1H), 7.91 (d, J=7.2 Hz, 1H), 7.71-7.66 (m, 1H), 7.48-7.08 (m, 8H), 6.91 (d, J=6.3 Hz, 2H), 4.67-4.21 (m, 3H), 3.10 (s, J=25.7 Hz, 3H), 2.88 (d, J=8.5 Hz, 1H), 2.72-2.70 (m, 1H). $^{13}$C NMR (100 MHz, DMSO-d6) δ 171.2, 169.6, 166.9, 163.5, 152.8, 150.4, 142.7, 137.9, 137.8, 135.7, 134.5, 133.2, 129.4, 129.1, 128.7, 127.9, 127.0, 125.5, 124.1, 123.1, 119.8, 116.8, 115.7, 55.5, 42.4, 42.1, 37.4; HRMS (ESI) m/z calcd for $C_{26}H_{23}FN_4O_4$ [M+H]$^+$475.1776, found 475.1774.

Example 33. Preparation of (S)-1-((2-(2,4-dioxo-1,4-dihydroquinazolin-3(2H)-yl)acetyl)-L-phenylalanyl)-N-phenylpyrrolidine-2-carboxamide

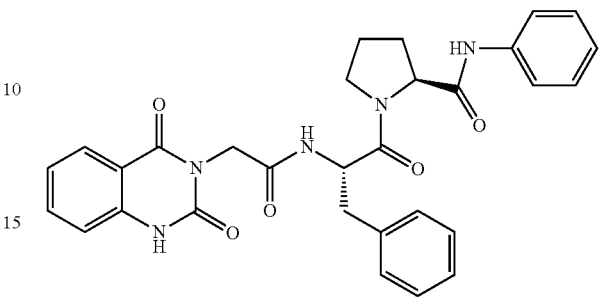

Using the general procedure described above, the title compound was prepared. $^1$H NMR (400 MHz, DMSO-d6) δ 11.45 (s, 1H), 8.61 (d, J=7.7 Hz, 1H), 7.91 (d, J=7.8 Hz, 1H), 7.68 (t, J=7.7 Hz, 1H), 7.24-7.20 (m, 6H), 7.04-6.98 (m, 2H), 6.94-6.89 (m, 4H), 4.54-4.52 (m, 1H), 4.46-4.33 (m, 2H), 3.79-3.75 (m, 3H), 3.12-3.09 (m, 3H), 2.90-2.83 (m, 2H), 2.68 (dd, J=13.4, 8.7 Hz, 1H). $^{13}$C NMR (100 MHz, DMSO-d6) δ 171.4, 166.8, 162.1, 158.9, 150.4, 139.9, 137.9, 135.9, 135.6, 129.4, 129.1, 128.6, 127.9, 126.9, 123.0, 115.6, 115.0, 114.1, 55.8, 51.9, 42.5, 37.9, 37.8, 36.2, 31.2; HRMS (ESI) m/z calcd for $C_{30}H_{29}N_5O_5$ [M+H]$^+$ 540.2241, found 540.2243.

Example 34. Preparation of (S)—N-(2-((1-(methyl(phenyl)amino)-1-oxo-3-phenylpropan-2-yl)amino)-2-oxoethyl)benzamide

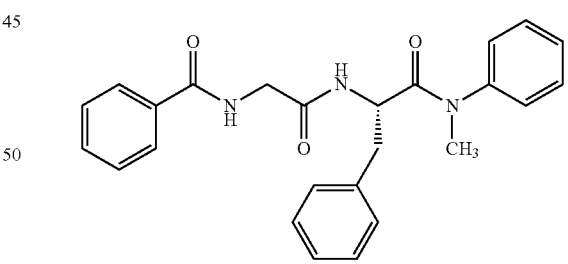

Using the general procedure described above, the title compound was prepared. $^1$H NMR (600 MHz, CDCl$_3$) δ 7.80 (d, J=7.4 Hz, 2H), 7.50 (t, J=7.3 Hz, 1H), 7.42 (t, J=7.7 Hz, 1H), 7.37-7.35 (m, 3H), 7.20-7.18 (m, 3H), 6.91-6.90 (m, 3H), 6.83 (brs, 1H), 4.85 (q, J=7.4 Hz, 1H), 4.15-4.07 (m, 2H), 3.24 (s, 3H), 2.94 (dd, J=13.3, 7.2 Hz, 1H), 2.76 (dd, J=13.3, 7.1 Hz, 1H); $^{13}$C NMR (150 MHz, CDCl$_3$) δ 171.1, 168.0, 167.4, 142.3, 136.0, 133.7, 131.7, 129.8, 129.3, 128.5, 128.5, 128.3, 127.3, 127.1, 127.0, 51.4, 43.2, 39.2, 37.7; HRMS-ESI (−) m/z calcd for $C_{25}H_{24}N_3O_3$ [M−H]$^−$ 414.1824, found 414.1823.

Example 35. Preparation of (S)—N-(2-((1-(methyl (p-tolyl)amino)-1-oxo-3-phenylpropan-2-yl)amino)-2-oxoethyl)benzamide

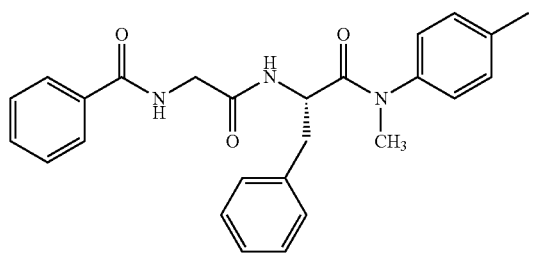 [SMILES: Cc1ccc(N(C)C(=O)[C@H](Cc2ccccc2)NC(=O)CNC(=O)c2ccccc2)cc1]

Using the general procedure described above, the title compound was prepared. $^1$H NMR (600 MHz, CDCl$_3$) δ 7.80 (d, J=7.4 Hz, 2H), 7.50 (t, J=7.4 Hz, 1H), 7.43-7.41 (m, 2H), 7.21-7.20 (m, 3H), 7.14 (d, J=8.0 Hz, 2H), 6.94-6.90 (m, 4H), 6.76 (brs, 1H), 4.86 (q, J=7.3 Hz, 1H), 4.14-4.08 (m, 2H), 3.22 (s, 3H), 2.95 (dd, J=13.3, 7.2 Hz, 1H), 2.77 (dd, J=13.3, 7.0 Hz, 1H), 2.37 (s, 3H); $^{13}$C NMR (150 MHz, CDCl$_3$) δ 171.2, 167.9, 167.3, 139.7, 138.2, 136.1, 133.8, 131.7, 130.4, 129.3, 128.5, 128.4, 127.1, 127.0, 126.9, 51.3, 43.1, 39.2, 37.8, 21.1; HRMS-ESI (−) m/z calcd for C$_{26}$H$_{26}$N$_3$O$_3$ [M−H]$^-$ 428.1988, found 428.1989.

Example 36. Preparation of (S)—N-(2-((1-((4-chlorophenyl)(methyl)amino)-1-oxo-3-phenylpropan-2-yl)amino)-2-oxoethyl)benzamide

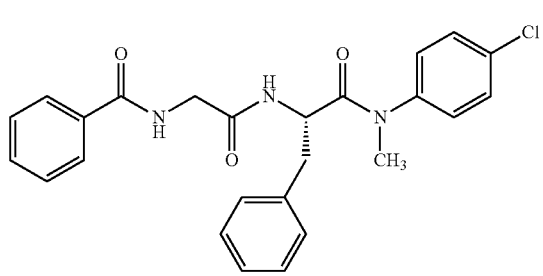 [SMILES: CN(C(=O)[C@H](Cc1ccccc1)NC(=O)CNC(=O)c1ccccc1)c1ccc(Cl)cc1]

Using the general procedure described above, the title compound was prepared. $^1$H NMR (600 MHz, CDCl$_3$) δ 7.81 (d, J=7.2 Hz, 2H), 7.51 (t, J=7.4 Hz, 1H), 7.43 (t, J=7.7 Hz, 2H), 7.28-7.22 (m, 5H), 7.03-6.96 (m, 4H), 6.69 (s, 1H), 4.79 (dd, J=14.7, 8.2 Hz, 1H), 4.14 (d, J=7.4 Hz, 2H), 3.18 (s, 3H), 2.96 (dd, J=13.1, 8.4 Hz, 1H), 2.81 (dd, J=13.1, 6.4 Hz, 1H); $^{13}$C NMR (150 MHz, CDCl$_3$) δ 171.2, 168.1, 167.4, 140.8, 135.9, 134.0, 133.7, 131.8, 129.8, 129.4, 128.7, 128.6, 128.6, 127.1, 127.1, 51.4, 43.2, 39.5, 37.7; HRMS-ESI (−) m/z calcd for C$_{25}$H$_{23}$ClN$_3$O$_3$ [M−H]$^-$ 448.1433, found 448.1440.

Example 37. Preparation of (S)—N-(2-((1-((3-chlorophenyl)(methyl)amino)-1-oxo-3-phenylpropan-2-yl)amino)-2-oxoethyl)benzamide

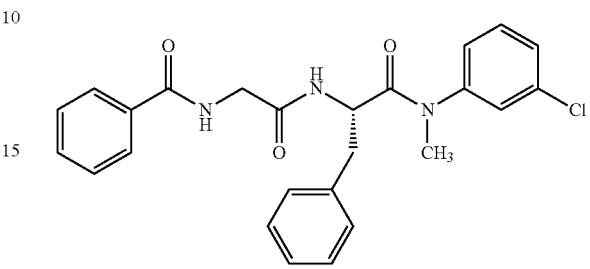

Using the general procedure described above, the title compound was prepared. $^1$H NMR (600 MHz, CD$_3$OD) δ 7.87 (d, J=7.4 Hz, 2H), 7.54 (t, J=7.4 Hz, 1H), 7.46 (t, J=7.7 Hz, 2H), 7.33-7.22 (m, 6H), 6.96-6.94 (m, 3H), 4.62 (t, J=7.8 Hz, 1H), 4.04 (s, 2H), 3.13 (s, 3H), 2.96 (dd, J=13.1, 8.5 Hz, 1H), 2.79 (dd, J=13.1, 6.6 Hz, 1H); $^{13}$C NMR (150 MHz, CD$_3$OD) δ 173.0, 171.0, 170.4, 145.1, 137.7, 135.9, 135.0, 132.9, 131.8, 130.3, 129.7, 129.6, 129.4, 128.7, 128.5, 128.1, 127.3, 53.4, 43.7, 39.6, 38.0; HRMS-ESI (−) m/z calcd for C$_{25}$H$_{23}$ClN$_3$O$_3$ [M−H]$^-$ 448.1433, found 448.1439.

Example 38. Preparation of (S)—N-(2-((1-((4-fluorophenyl)(methyl)amino)-1-oxo-3-phenylpropan-2-yl)amino)-2-oxoethyl)benzamide

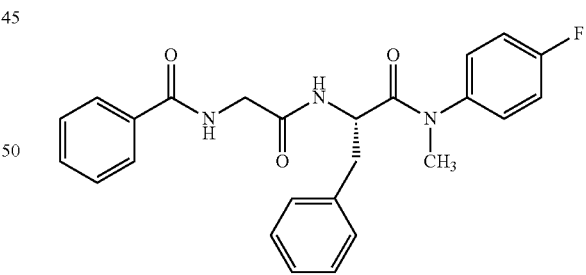

Using the general procedure described above, the title compound was prepared. $^1$H NMR (600 MHz, CD$_3$OD) δ 7.86 (d, J=7.2 Hz, 2H), 7.55 (t, J=8.4 Hz, 1H), 7.48-7.45 (m, 3H), 7.22-7.21 (m, 3H), 7.06-7.03 (m, 3H), 6.95-6.94 (m, 2H), 4.62 (t, J=7.5 Hz, 1H), 4.02 (s, 2H), 3.14 (s, 3H), 2.97 (dd, J=13.2, 7.9 Hz, 1H), 2.77 (dd, J=13.2, 7.0 Hz, 1H); $^{13}$C NMR (150 MHz, CD$_3$OD) δ 173.2, 171.0, 170.4, 163.4 (d, J$_{CF}$=246.9 Hz), 140.0, 137.9, 135.0, 132.9, 130.7 (d, J=7.5 Hz), 130.3, 129.6, 129.5, 128.5, 128.0, 117.3 (d, J=23.1 Hz), 53.2, 43.7, 39.4, 38.1; HRMS-ESI (−) m/z calcd for C$_{25}$H$_{23}$FN$_3$O$_3$ [M−H]$^-$ 432.1729, found 432.1734.

Example 39. Preparation of (S)—N-(2-((1-((3-fluorophenyl)(methyl)amino)-1-oxo-3-phenylpropan-2-yl)amino)-2-oxoethyl)benzamide

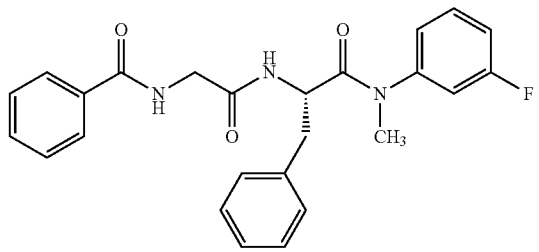 [SMILES: CN(C(=O)[C@H](Cc1ccccc1)NC(=O)CNC(=O)c1ccccc1)c1cccc(F)c1]

Using the general procedure described above, the title compound was prepared. $^1$H NMR (600 MHz, CDCl$_3$) δ 7.82 (d, J=7.6 Hz, 2H), 7.51 (t, J=7.4 Hz, 1H), 7.44-7.42 (m, 2H), 7.32-7.28 (m, 1H), 7.25-7.21 (m, 3H), 7.04-6.95 (m, 5H), 6.73 (s, 1H), 6.33 (s, 1H), 4.85-4.81 (m, 1H), 4.17-4.11 (m, 2H), 3.20 (s, 3H), 2.96 (dd, J=13.1, 8.4 Hz, 1H), 2.82 (dd, J=13.1, 6.4 Hz, 1H); $^{13}$C NMR (100 MHz, CDCl$_3$) δ 171.2, 168.2, 167.5, 162.8 (d, J$_{CF}$=249.3 Hz), 143.7 (d, J$_{CF}$=9.5 Hz), 135.9, 133.7, 131.8, 130.8 (d, J$_{CF}$=9.1 Hz), 129.3, 128.6, 128.6, 127.2, 123.2 (d, J$_{CF}$=2.9 Hz), 115.4 (d, J$_{CF}$=20.9 Hz), 114.7 (d, J=22.2 Hz), 51.5, 43.2, 39.5, 37.6; HRMS-ESI (−) m/z calcd for C$_{25}$H$_{23}$FN$_3$O$_3$ [M−H]$^−$ 432.1729, found 432.1732.

Example 40. Preparation of (S)—N-(2-((1-((3-bromophenyl)(methyl)amino)-1-oxo-3-phenylpropan-2-yl)amino)-2-oxoethyl)benzamide

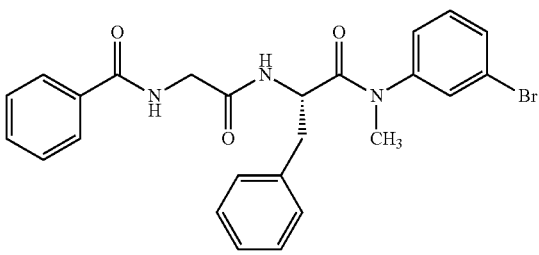 [SMILES: CN(C(=O)[C@H](Cc1ccccc1)NC(=O)CNC(=O)c1ccccc1)c1cccc(Br)c1]

Using the general procedure described above, the title compound was prepared. $^1$H NMR (600 MHz, CD$_3$OD) δ 7.87 (d, J=7.3 Hz, 2H), 7.54 (t, J=7.4 Hz, 1H), 7.48-7.45 (m, 3H), 7.25-7.22 (m, 5H), 6.98-6.95 (m, 3H), 4.62 (t, J=7.8 Hz, 1H), 4.04 (s, 2H), 3.13 (s, 3H), 2.96 (dd, J=13.1, 8.6 Hz, 1H), 2.79 (dd, J=13.1, 6.6 Hz, 1H); $^{13}$C NMR (150 MHz, CD$_3$OD) δ 173.0, 171.0, 170.4, 145.2, 137.7, 135.0, 132.9, 132.4, 132.1, 131.5, 130.3, 129.7, 129.6, 128.5, 128.2, 127.7, 123.6, 53.4, 43.7, 39.6, 38.0; HRMS-ESI (−) m/z calcd for C$_{25}$H$_{23}$BrN$_3$O$_3$ [M−H]$^−$ 492.0928, found 492.0933.

Example 41. Preparation of (S)—N-(2-((1-(ethyl(phenyl)amino)-1-oxo-3-phenylpropan-2-yl)amino)-2-oxoethyl)benzamide

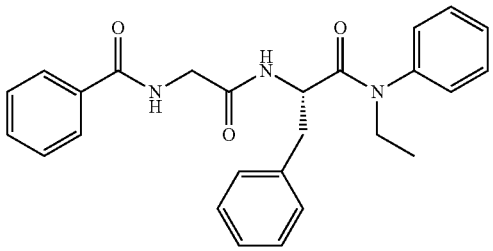 [SMILES: CCN(C(=O)[C@H](Cc1ccccc1)NC(=O)CNC(=O)c1ccccc1)c1ccccc1]

Using the general procedure described above, the title compound was prepared. $^1$H NMR (600 MHz, CDCl$_3$) δ 7.81 (d, J=7.6 Hz, 2H), 7.49-7.45 (m, 2H), 7.40-7.34 (m, 5H), 7.26-7.25 (m, 1H), 7.19-7.16 (m, 3H), 6.93-6.92 (m, 2H), 4.73 (q, J=7.4 Hz, 1H), 4.13-4.08 (m, 2H), 3.85-3.79 (m, 1H), 3.66-3.60 (m, 1H), 2.97 (dd, J=13.3, 7.1 Hz, 1H), 2.78 (dd, J=13.3, 7.3 Hz, 1H), 1.09 (t, J=7.2 Hz, 3H); $^{13}$C NMR (100 MHz, CDCl$_3$) δ 170.8, 168.3, 167.4, 140.7, 136.3, 133.8, 131.6, 129.6, 129.4, 128.5, 128.4, 128.4, 127.2, 126.9, 51.8, 44.8, 43.1, 39.1, 12.8; HRMS-ESI (−) m/z calcd for C$_{26}$H$_{26}$N$_3$O$_3$ [M−H]$^−$ 428.1988, found 428.1990.

Example 42. Preparation of (S)—N-methyl-2-(2-(5-methyl-2,4-dioxo-3,4-dihydropyrimidin-1(2H)-yl)acetamido)-N,3-diphenylpropanamide

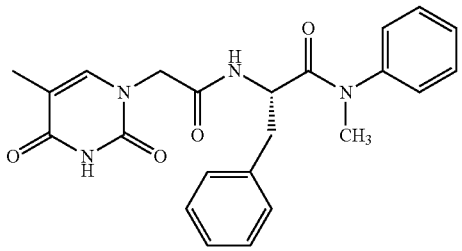 [SMILES: Cc1cn(CC(=O)N[C@@H](Cc2ccccc2)C(=O)N(C)c2ccccc2)c(=O)[nH]c1=O]

Using the general procedure described above, the title compound was prepared. $^1$H NMR (600 MHz, CDCl$_3$) δ 9.35 (s, 1H), 7.50 (s, 1H), 7.38-7.35 (m, 3H), 7.19-7.17 (m, 3H), 6.94-6.86 (m, 4H), 4.84 (q, J=7.8 Hz, 1H), 4.43 (d, J=15.8 Hz, 1H), 4.21 (d, J=15.8 Hz, 1H), 3.26 (s, 3H), 2.92 (dd, J=13.4, 6.8 Hz, 1H), 2.74 (dd, J=13.4, 7.6 Hz, 1H), 1.89 (s, 3H); $^{13}$C NMR (150 MHz, CDCl$_3$) δ 171.2, 166.0, 164.1, 151.1, 142.2, 140.4, 136.0, 129.9, 129.3, 128.4, 127.2, 126.9, 110.9, 51.5, 49.6, 38.9, 37.8, 12.4; HRMS-ESI (−) m/z calcd for C$_{23}$H$_{23}$N$_4$O$_4$ [M−H]$^−$ 419.1725, found 419.1730.

Example 43. Preparation of (S)—N-methyl-2-(2-(5-methyl-2,4-dioxo-3,4-dihydropyrimidin-1(2H)-yl)acetamido)-3-phenyl-N-(p-tolyl)propenamide

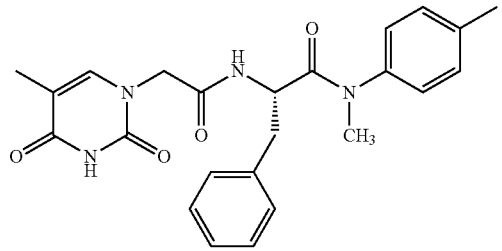

Using the general procedure described above, the title compound was prepared. $^1$H NMR (600 MHz, CDCl$_3$) δ 9.47 (s, 1H), 7.61 (d, J=8.5 Hz, 1H), 7.19-7.14 (m, 5H), 6.95-6.89 (m, 3H), 6.80 (brs, 1H), 4.87-4.83 (m, 1H), 4.45 (d, J=15.8 Hz, 1H), 4.20 (d, J=15.8 Hz, 1H), 3.23 (s, 3H), 2.92 (dd, J=13.4, 6.9 Hz, 1H), 2.74 (dd, J=13.4, 7.5 Hz, 1H), 2.36 (s, 3H), 1.89 (s, 3H); $^{13}$C NMR (150 MHz, CDCl$_3$) δ 171.4, 166.0, 164.2, 151.1, 140.5, 139.6, 138.3, 136.1, 130.4, 129.4, 128.4, 126.9, 126.8, 110.9, 51.4, 49.5, 39.0, 37.9, 21.1, 12.4; HRMS-ESI (−) m/z calcd for C$_{24}$H$_{25}$N$_4$O$_4$ [M−H]$^−$ 433.1881, found 433.1890.

Example 44. Preparation of (S)—N-(4-chlorophenyl)-N-methyl-2-(2-(5-methyl-2,4-dioxo-3,4-dihydropyrimidin-1(2H)-yl)acetamido)-3-phenylpropanamide

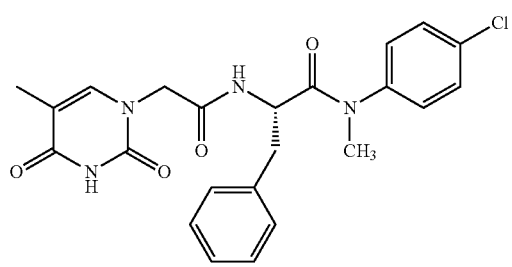 [SMILES: Cc1cn(CC(=O)N[C@@H](Cc2ccccc2)C(=O)N(C)c2ccc(Cl)cc2)c(=O)[nH]c1=O]

Using the general procedure described above, the title compound was prepared. $^1$H NMR (600 MHz, CDCl$_3$) δ 9.48 (s, 1H), 7.56 (d, J=8.4 Hz, 1H), 7.28 (d, J=8.6 Hz, 2H), 7.23-7.22 (m, 3H), 6.98-6.97 (m, 1H), 6.94-6.92 (m, 2H), 6.73 (brs, 1H), 4.78 (dd, J=15.3, 8.0 Hz, 1H), 4.43 (d, J=15.8 Hz, 1H), 4.24 (d, J=15.8 Hz, 1H), 3.20 (s, 3H), 2.93 (dd, J=13.2, 8.0 Hz, 1H), 2.78 (dd, J=13.2, 6.9 Hz, 1H), 1.91 (s, 3H); $^{13}$C NMR (150 MHz, CDCl$_3$) δ 171.3, 166.1, 164.2, 151.1, 140.6, 140.4, 135.8, 134.1, 129.9, 129.4, 128.6, 128.5, 127.0, 111.0, 51.5, 49.6, 39.2, 37.8, 12.4; HRMS-ESI (−) m/z calcd for C$_{23}$H$_{22}$ClN$_4$O$_4$ [M−H]$^−$ 453.1335, found 453.1340.

Example 45. Preparation of (S)—N-(3-chlorophenyl)-N-methyl-2-(2-(5-methyl-2,4-dioxo-3,4-dihydropyrimidin-1(2H)-yl)acetamido)-3-phenylpropanamide

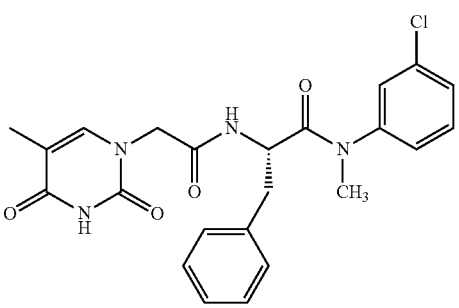

Using the general procedure described above, the title compound was prepared. $^1$H NMR (600 MHz, CD$_3$OD) δ 7.33-7.26 (m, 7H), 6.96 (m, 3H), 4.59 (t, J=7.6 Hz, 1H), 4.40 (q, J=16.4 Hz, 2H), 3.13 (s, 3H), 2.98 (dd, J=13.0, 8.7 Hz, 1H), 2.79 (dd, J=13.1, 6.6 Hz, 1H), 1.86 (s, 3H); $^{13}$C NMR (150 MHz, CD$_3$OD) δ 172.9, 168.9, 167.0, 153.0, 145.0, 143.6, 137.7, 135.9, 131.9, 130.3, 129.7, 129.4, 128.7, 128.2, 127.3, 111.0, 53.5, 50.5, 39.6, 38.0, 12.2; HRMS-ESI (−) m/z calcd for C$_{23}$H$_{22}$ClN$_4$O$_4$ [M−H]$^−$ 453.1335, found 453.1339.

Example 46. Preparation of (S)—N-(4-fluorophenyl)-N-methyl-2-(2-(5-methyl-2,4-dioxo-3,4-dihydropyrimidin-1(2H)-yl)acetamido)-3-phenylpropanamide

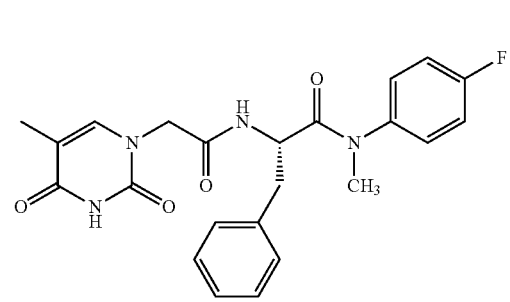 [SMILES: Cc1cn(CC(=O)N[C@@H](Cc2ccccc2)C(=O)N(C)c2ccc(F)cc2)c(=O)[nH]c1=O]

Using the general procedure described above, the title compound was prepared. $^1$H NMR (600 MHz, CD$_3$OD) δ 7.25-7.23 (m, 4H), 7.03-6.95 (m, 6H), 4.58 (t, J=7.5 Hz, 1H), 4.41-4.35 (m, 2H), 3.14 (s, 3H), 2.98 (dd, J=13.2, 8.1 Hz, 1H), 2.77 (dd, J=13.2, 7.0 Hz, 1H), 1.86 (s, 3H); $^{13}$C NMR (150 MHz, CD$_3$OD) δ 173.1, 168.9, 167.0, 163.4 (d, J$_{CF}$=247.1 Hz), 153.0, 143.6, 139.9 (d, J$_{CF}$=3.0 Hz), 137.9, 130.7, 130.4, 129.6, 128.1, 117.4 (d, J$_{CF}$=23.0 Hz), 111.0, 53.4, 50.5, 39.4, 38.1, 12.2; HRMS-ESI (−) m/z calcd for C$_{23}$H$_{22}$FN$_4$O$_4$ [M−H]$^−$ 437.1631, found 437.1635.

Example 47. Preparation of (S)—N-(3-fluorophenyl)-N-methyl-2-(2-(5-methyl-2,4-dioxo-3,4-dihydropyrimidin-1(2H)-yl)acetamido)-3-phenylpropanamide

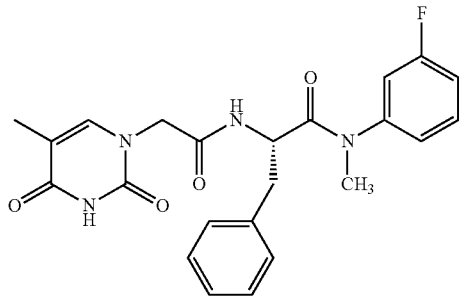 [SMILES: Cc1cn(CC(=O)N[C@@H](Cc2ccccc2)C(=O)N(C)c2cccc(F)c2)c(=O)[nH]c1=O]

Using the general procedure described above, the title compound was prepared. $^1$H NMR (600 MHz, CDCl$_3$) δ 9.77 (s, 1H), 7.79 (d, J=8.2 Hz, 1H), 7.32-7.29 (m, 1H), 7.25-7.21 (m, 3H), 7.04-7.00 (m, 2H), 6.93-6.92 (m, 2H), 6.77 (s, 1H), 6.37 (s, 1H), 4.84-4.80 (m, 1H), 4.46-4.28 (m, 2H), 3.21 (s, 3H), 2.94 (dd, J=13.2, 8.1 Hz, 1H), 2.80 (dd, J=13.2, 6.9 Hz, 1H), 1.91 (s, 3H); $^{13}$C NMR (100 MHz, CDCl$_3$) δ 171.4, 166.2, 164.3, 1162.8 (d, J=249.4 Hz), 151.3, 143.5 (d, J=9.4 Hz), 140.6, 135.9, 130.9 (d, J=9.1 Hz), 129.3, 128.5, 127.1, 123.2, 115.5 (d, J=20.9 Hz), 114.7 (d, J=22.3 Hz), 111.0, 51.7, 49.6, 39.2, 37.7, 12.4; HRMS-ESI (−) m/z calcd for C$_{23}$H$_{22}$FN$_4$O$_4$ [M−H]$^-$ 437.1631, found 437.1632.

Example 48. Preparation of (S)—N-(3-bromophenyl)-N-methyl-2-(2-(5-methyl-2,4-dioxo-3,4-dihydropyrimidin-1(2H)-yl)acetamido)-3-phenylpropanamide

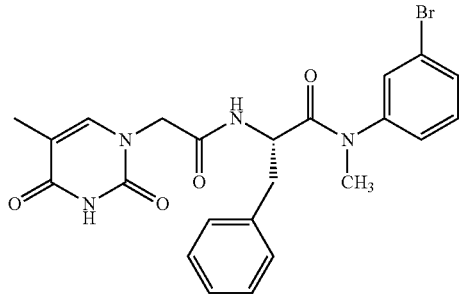

Using the general procedure described above, the title compound was prepared. $^1$H NMR (600 MHz, CD$_3$OD) δ 7.47 (d, J=7.9 Hz, 1H), 7.28-7.22 (m, 6H), 7.01-6.95 (m, 3H), 4.60-4.57 (m, 1H), 4.40 (q, J=16.5 Hz, 2H), 3.13 (s, 3H), 2.97 (dd, J=13.1, 8.7 Hz, 1H), 2.79 (dd, J=13.1, 6.6 Hz, 1H), 1.86 (s, 3H); $^{13}$C NMR (150 MHz, CD$_3$OD) δ 172.8, 168.9, 167.0, 153.0, 145.1, 143.6, 137.6, 132.4, 132.1, 131.5, 130.3, 129.7, 128.2, 127.7, 123.6, 111.0, 53.5, 50.5, 39.6, 38.0, 12.2; HRMS-ESI (−) m/z calcd for C$_{23}$H$_{22}$BrN$_4$O$_4$ [M−H]$^-$ 497.0830, found 497.0835.

Example 49. Preparation of (S)-2-(2-methyl-1H-indol-3-yl)-N-(2-phenyl-1-(3-phenylpyridin-2-yl)ethyl)acetamide

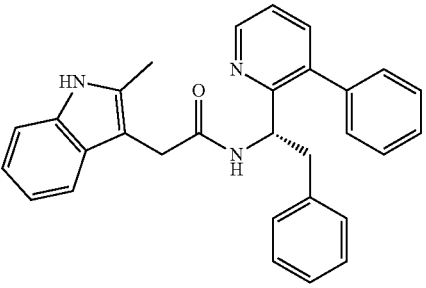 [SMILES: Cc1[nH]c2ccccc2c1CC(=O)N[C@@H](Cc1ccccc1)c1ncccc1-c1ccccc1]

Using the general procedure described above, the title compound was prepared. $^1$H NMR (400 MHz, CDCl$_3$) δ 8.29 (dd, J=4.8, 1.6 Hz, 1H), 8.20 (s, 1H), 7.38-7.25 (m, 5H), 7.22-7.16 (m, 1H), 7.12-7.01 (m, 2H), 7.04-6.94 (m, 4H), 6.90 (t, J=7.4 Hz, 2H), 6.81 (d, J=8.6 Hz, 1H), 6.44 (d, J=7.3 Hz, 2H), 5.52 (q, J=7.4 Hz, 1H), 3.55 (d, J=1.7 Hz, 2H), 2.78-2.60 (m, 2H), 2.19 (s, 3H). $^{13}$C NMR (100 MHz, CDCl$_3$) δ 170.8, 156.9, 147.8, 138.2, 137.9, 137.1, 136.9, 135.5, 133.4, 129.3, 129.2, 128.6, 128.5 128.1, 127.8, 126.2, 122.1, 121.4, 119.7, 118.1, 110.5, 104.9, 51.7, 42.1, 32.5, 11.7. HRMS (ESI) m/z calcd for C$_{30}$H$_{27}$N$_3$O [M−H]$^-$ 444.2081, found 444.2083.

Example 50. Preparation of (S)-2-(1H-indazol-1-yl)-N-(2-phenyl-1-(3-phenylpyridin-2-yl)ethyl)acetamide

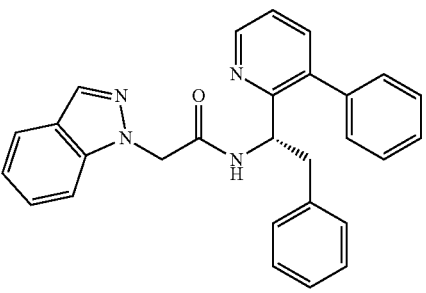 [SMILES: O=C(Cn1ncc2ccccc21)N[C@@H](Cc1ccccc1)c1ncccc1-c1ccccc1]

Using the general procedure described above, the title compound was prepared. $^1$H NMR (400 MHz, CDCl$_3$) δ 8.39 (d, J=4.9 Hz, 1H), 8.12 (s, 1H), 7.77 (d, J=8.1 Hz, 1H), 7.47-7.14 (m, 8H), 7.10-6.89 (m, 6H), 6.48 (d, J=7.5 Hz, 2H), 5.53 (q, J=7.4 Hz, 1H), 5.02 (d, J=1.8 Hz, 2H), 2.85-2.68 (m, 2H). $^{13}$C NMR (100 MHz, CDCl$_3$) δ 166.7, 156.1, 147.8, 140.3, 138.3, 137.9, 136.9, 136.7, 135.1, 129.3, 129.1, 128.7, 128.1, 128.0, 127.9, 127.2, 126.4, 124.4, 122.4, 121.4, 109.2, 52.4, 51.8, 42.1. HRMS (ESI) m/z calcd for C$_{28}$H$_{24}$N$_4$O [M−H]$^-$ 431.1877, found 431.1878.

Example 51. Preparation of (S)—N-(2-phenyl-1-(3-phenylpyridin-2-yl)ethyl)-2-(1H-pyrazol-1-yl)acetamide

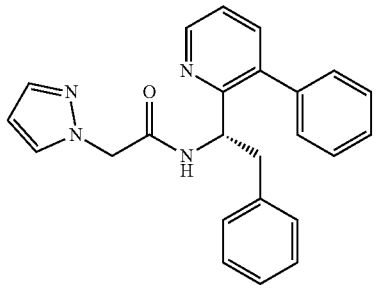 [SMILES: O=C(Cn1cccn1)N[C@@H](Cc1ccccc1)c1ncccc1-c1ccccc1]

Using the general procedure described above, the title compound was prepared. $^1$H NMR (400 MHz, CDCl$_3$) δ 8.46 (dd, J=4.9, 1.7 Hz, 1H), 7.67-7.57 (m, 2H), 7.50-7.34 (m, 4H), 7.28 (p, J=3.6 Hz, 3H), 7.24-7.11 (m, 2H), 7.07-6.87 (m, 5H), 6.56-6.49 (m, 2H), 6.29 (t, J=2.2 Hz, 1H), 5.47 (q, J=7.5 Hz, 1H), 4.73 (d, J=3.6 Hz, 2H), 2.87-2.72 (m, 2H). $^{13}$C NMR (100 MHz, CDCl$_3$) δ 166.2, 156.2, 148.1, 141.0, 137.9, 136.9, 132.2, 130.9, 129.4, 129.1, 128.7, 128.5, 128.1, 127.8, 126.3, 122.3, 106.7, 55.2, 51.9, 42.3. HRMS (ESI) m/z calcd for C$_{24}$H$_{22}$N$_4$O [M−H]$^-$ 381.1721, found 381.1725.

Example 52. Preparation of (S)-2-(2-methyl-1H-indol-3-yl)-N-(2-phenyl-1-(1-phenyl-1H-imidazol-2-yl)ethyl)acetamide

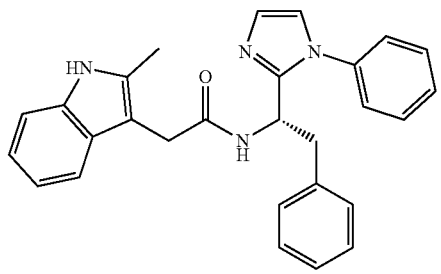 [SMILES: Cc1[nH]c2ccccc2c1CC(=O)N[C@@H](Cc1ccccc1)c1nccn1-c1ccccc1]

Using the general procedure described above, the title compound was prepared. $^1$H NMR (600 MHz, CDCl$_3$) δ 8.75 (s, 1H), 7.40 (d, J=7.8 Hz, 1H), 7.35 (tt, J=7.8, 2.4 Hz, 1H), 7.30 (dd, J=8.4, 6.9 Hz, 2H), 7.20 (d, J=7.8 Hz, 1H), 7.15-6.99 (m, 7H), 6.85-6.80 (m, 3H), 6.71-6.67 (m, 2H), 5.29 (td, J=9.0, 5.8 Hz, 1H), 3.64 (s, 2H), 3.04 (dd, J=12.9, 9.6 Hz, 1H), 2.98 (dd, J=12.9, 5.8 Hz, 1H), 2.20 (s, 3H). $^{13}$C NMR (100 MHz, CDCl$_3$) δ 171.2, 147.8, 136.4, 136.2, 135.6, 133.6, 129.5, 129.4, 129.0, 128.9, 128.5, 128.4, 126.8, 126.2, 121.5, 121.0, 119.7, 117.9, 110.6, 104.5, 47.2, 41.9, 32.4, 11.8. HRMS (ESI) m/z calcd for C$_{28}$H$_{26}$N$_4$O [M+H]$^+$ 435.2179, found 435.2182.

Example 53. Preparation of (S)—N-(1-(1-(4-cyanophenyl)-1H-imidazol-2-yl)-2-phenylethyl)-2-(2-methyl-1H-indol-3-yl)acetamide

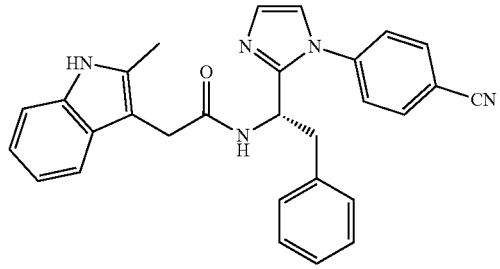 [SMILES: Cc1[nH]c2ccccc2c1CC(=O)N[C@@H](Cc1ccccc1)c1nccn1-c1ccc(C#N)cc1]

Using the general procedure described above, the title compound was prepared. $^1$H NMR (600 MHz, CDCl$_3$) δ 8.44 (s, 1H), 7.55 (d, J=8.4 Hz, 2H), 7.40 (d, J=7.8 Hz, 1H), 7.26 (t, J=4.0 Hz, 1H), 7.15-7.01 (m, 6H), 6.94 (d, J=8.3 Hz, 2H), 6.78-6.73 (m, 2H), 6.67-6.62 (m, 2H), 5.16 (ddd, J=9.7, 8.4, 6.0 Hz, 1H), 3.65 (d, J=3.9 Hz, 2H), 3.01-2.91 (m, 2H), 2.31 (s, 3H). $^{13}$C NMR (100 MHz, CDCl$_3$) δ 171.4, 147.8, 140.2, 136.4, 135.6, 133.6, 133.5, 133.3, 129.3, 128.5, 128.4, 128.4, 126.9, 121.7, 120.3, 119.9, 117.9, 117.8, 112.5, 110.7, 104.3, 47.5, 42.2, 32.3, 11.8. HRMS (ESI) m/z calcd for C$_{29}$H$_{25}$N$_5$O [M+H]$^+$ 460.2132, found 460.2133.

Example 54. Preparation of (S)-2-(1H-indol-3-yl)-N-(2-phenyl-1-(3-(4-chlorophenyl)pyridin-2-yl)ethyl)acetamide

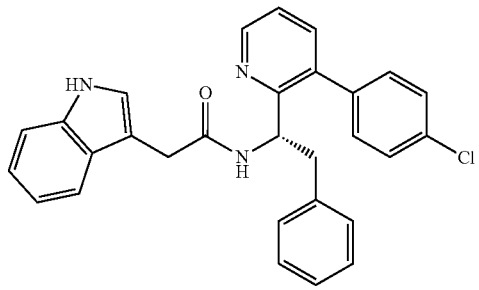 [SMILES: O=C(Cc1c[nH]c2ccccc12)N[C@@H](Cc1ccccc1)c1ncccc1-c1ccc(Cl)cc1]

Using the general procedure described above, the title compound was prepared. $^1$H NMR (400 MHz, CDCl$_3$) δ 8.48-8.40 (m, 2H), 7.42 (dd, J=16.3, 7.9 Hz, 2H), 7.34-7.24 (m, 3H), 7.24-7.09 (m, 2H), 7.03 (dt, J=10.1, 3.4 Hz, 4H), 6.95 (t, J=7.5 Hz, 2H), 6.87 (d, J=8.0 Hz, 2H), 6.54-6.47 (m, 2H), 5.47 (q, J=7.8 Hz, 1H), 3.68 (s, 2H), 2.89-2.81 (m, 2H). $^{13}$C NMR (100 MHz, CDCl$_3$) δ 171.05, 156.81, 147.26, 138.90, 136.68, 136.58, 135.97, 134.23, 130.61, 129.32, 128.72, 128.28, 127.29, 126.50, 123.88, 122.59, 122.37, 119.83, 118.96, 111.39, 109.04, 51.86, 42.16, 33.67 (one carbon merging). HRMS (ESI) m/z calcd for C$_{29}$H$_{24}$ClN$_3$O [M+H]$^-$ 464.1535, found 464.1535.

Example 55. Preparation of (S)-2-(5-methoxy-1H-indol-3-yl)-N-(2-phenyl-1-(3-(4-chlorophenyl)pyridin-2-yl)ethyl)acetamide

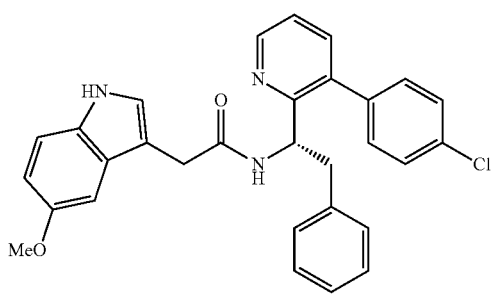 [SMILES: COc1ccc2[nH]cc(CC(=O)N[C@@H](Cc3ccccc3)c3ncccc3-c3ccc(Cl)cc3)c2c1]

Using the general procedure described above, the title compound was prepared. $^1$H NMR (600 MHz, CDCl$_3$) δ 8.47 (d, J=4.9 Hz, 1H), 8.43 (s, 1H), 7.55 (s, 1H), 7.35 (s, 2H), 7.32-7.28 (m, 2H), 7.23 (dt, J=8.7, 2.3 Hz, 1H), 7.14 (s, 1H), 7.06 (t, J=7.4 Hz, 1H), 6.95 (t, J=7.5 Hz, 4H), 6.89 (d, J=2.3 Hz, 1H), 6.83 (dq, J=8.7, 2.1 Hz, 1H), 6.52 (d, J=7.5 Hz, 2H), 5.47 (q, J=7.8 Hz, 1H), 3.75 (s, 3H), 3.69 (d, J=4.9 Hz, 2H), 2.97 (d, J=7.6 Hz, 2H). $^{13}$C NMR (100 MHz, CDCl$_3$) δ 171.42, 156.54, 154.33, 136.29, 134.60, 131.59, 130.60, 129.19, 128.83, 128.35, 127.67, 126.63, 124.82, 123.05, 112.85, 112.18, 108.64, 100.39, 55.94, 51.90, 41.89, 33.70 (four carbons are too short to pick between 147-134 ppm). HRMS (ESI) m/z calcd for C$_{30}$H$_{26}$ClN$_3$O$_2$ [M+H]$^-$ 494.1641, found 494.1640.

Example 56. Preparation of (S)-2-(5-hydroxy-1H-indol-3-yl)-N-(2-phenyl-1-(3-(4-chlorophenyl)pyridin-2-yl)ethyl)acetamide

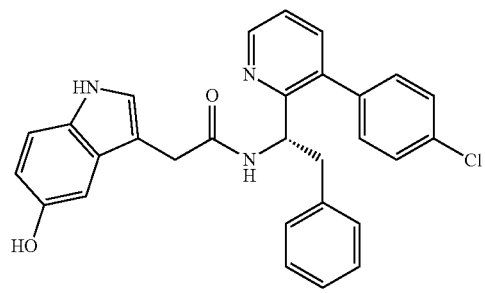 [SMILES: O=C(Cc1c[nH]c2ccc(O)cc12)N[C@@H](Cc1ccccc1)c1ncccc1-c1ccc(Cl)cc1]

Using the general procedure described above, the title compound was prepared. $^1$H NMR (600 MHz, CDCl$_3$) δ 8.53 (d, J=4.9 Hz, 1H), 8.43 (s, 1H), 7.44 (d, J=7.7 Hz, 1H), 7.33 (s, 1H), 7.26 (dd, J=16.3, 8.0 Hz, 3H), 7.15 (d, J=8.6 Hz, 1H), 7.10 (t, J=7.4 Hz, 1H), 7.00 (dd, J=17.4, 9.9 Hz, 4H), 6.93 (d, J=7.9 Hz, 2H), 6.82 (dd, J=8.7, 2.3 Hz, 1H), 6.56 (d, J=7.5 Hz, 2H), 5.51 (q, J=7.7 Hz, 1H), 3.68-3.59 (m, 2H), 2.97 (d, J=7.5 Hz, 2H). $^{13}$C NMR (100 MHz, CDCl$_3$) δ 171.81, 156.58, 150.47, 147.10, 139.28, 136.84, 136.51, 135.79, 134.21, 131.50, 130.60, 129.29, 128.68, 128.32, 128.02, 126.53, 124.83, 122.84, 112.59, 112.11, 108.01, 103.43, 52.08, 41.90, 33.57. HRMS (ESI) m/z calcd for C$_{29}$H$_{24}$ClN$_3$O$_2$ [M+H]$^-$ 480.1484, found 480.1486.

Example 57. Preparation of (S)-2-(1-ethyl-1H-indol-3-yl)-N-(2-phenyl-1-(3-(4-chlorophenyl)pyridin-2-yl)ethyl)acetamide

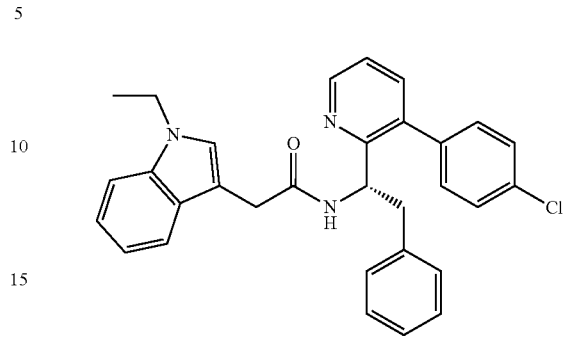

Using the general procedure described above, the title compound was prepared. $^1$H NMR (400 MHz, CDCl$_3$) δ 8.32 (dd, J=4.8, 1.7 Hz, 1H), 7.33 (dt, J=8.0, 1.0 Hz, 1H), 7.30-7.24 (m, 1H), 7.23-7.02 (m, 6H), 6.92 (dddd, J=8.0, 5.4, 2.8, 1.2 Hz, 3H), 6.88-6.81 (m, 2H), 6.76 (d, J=8.0 Hz, 2H), 6.44-6.37 (m, 2H), 5.34 (td, J=8.1, 6.7 Hz, 1H), 4.02 (q, J=7.3 Hz, 2H), 3.60-3.53 (m, 2H), 2.74 (dd, J=7.4, 2.3 Hz, 2H), 1.33 (t, J=7.3 Hz, 3H). $^{13}$C NMR (100 MHz, CDCl$_3$) δ 171.01, 156.88, 147.39, 138.68, 136.80, 136.51, 136.27, 136.08, 134.15, 130.61, 129.33, 128.70, 128.22, 127.93, 126.58, 126.43, 122.47, 121.84, 119.33, 119.21, 109.47, 107.72, 51.78, 42.15, 41.01, 33.62, 15.60. HRMS (ESI) m/z calcd for C$_{31}$H$_{28}$ClN$_3$O [M+H]$^-$ 492.1848, found 492.1843.

Example 58. Preparation of (S)-2-(1-ethyl-5-methoxy-1H-indol-3-yl)-N-(2-phenyl-1-(3-(4-chlorophenyl)pyridin-2-yl)ethyl)acetamide

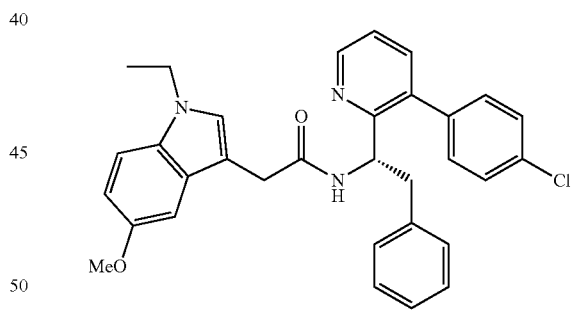

Using the general procedure described above, the title compound was prepared. $^1$H NMR (400 MHz, CDCl$_3$) δ 8.45 (dd, J=4.7, 1.7 Hz, 1H), 7.42 (d, J=7.4 Hz, 1H), 7.33-7.16 (m, 4H), 7.12-7.00 (m, 3H), 6.99-6.89 (m, 6H), 6.87 (dd, J=5.6, 3.0 Hz, 1H), 6.56-6.49 (m, 2H), 5.47 (td, J=8.2, 6.7 Hz, 1H), 4.13 (q, J=7.3 Hz, 2H), 3.75 (s, 3H), 3.66 (s, 2H), 2.88 (d, J=6.6 Hz, 2H), 1.46 (t, J=7.3 Hz, 3H). $^{13}$C NMR (101 MHz, CDCl$_3$) δ 171.19, 156.86, 154.12, 136.71, 134.20, 131.58, 130.62, 129.28, 128.71, 128.23, 128.18, 127.13, 126.45, 122.54, 112.10, 110.33, 107.15, 100.64, 55.96, 51.86, 42.11, 41.18, 33.67, 15.65 (four carbons are too short to pick between 148-135 ppm). HRMS (ESI) m/z calcd for C$_{32}$H$_{30}$ClN$_3$O$_2$ [M+H]$^-$ 522.1954, found 522.1954.

Example 59. Preparation of (S)-2-(5-methoxy-1H-indol-3-yl)-N-(2-phenyl-1-(3-(4-bromophenyl)pyridin-2-yl)ethyl)acetamide

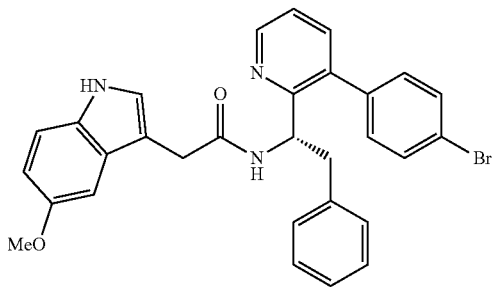

Using the general procedure described above, the title compound was prepared. ¹H NMR (400 MHz, CDCl₃) δ 8.44 (dd, J=5.0, 1.7 Hz, 1H), 8.19 (s, 1H), 7.47 (d, J=7.5 Hz, 1H), 7.31-7.20 (m, 5H), 7.15-7.10 (m, 1H), 7.08-6.98 (m, 1H), 6.98-6.77 (m, 7H), 6.50 (dd, J=8.0, 1.4 Hz, 2H), 5.45 (q, J=7.8 Hz, 1H), 3.72 (s, 3H), 3.67 (s, 2H), 2.90 (d, J=7.6 Hz, 2H). ¹³C NMR (101 MHz, CDCl₃) δ 171.32, 156.65, 154.40, 137.28, 136.41, 134.53, 131.57, 130.63, 129.64, 129.24, 128.82, 128.34, 128.04, 127.71, 126.61, 124.72, 122.92, 112.96, 112.16, 108.84, 100.42, 55.94, 51.90, 41.95, 33.72 (one carbon merging).

Example 60. Preparation of (S)-2-(1-ethyl-1H-indol-3-yl)-N-(2-phenyl-1-(3-(4-bromophenyl)pyridin-2-yl)ethyl)acetamide

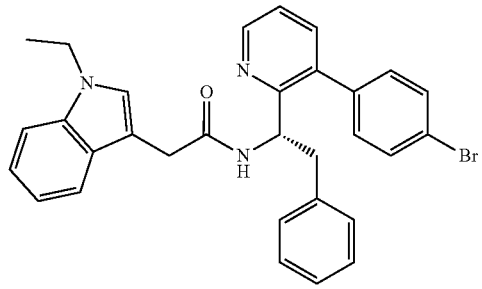 [SMILES: CCn1cc(CC(=O)N[C@@H](Cc2ccccc2)c2ncccc2-c2ccc(Br)cc2)c2ccccc21]

Using the general procedure described above, the title compound was prepared. ¹H NMR (600 MHz, CDCl₃) δ 8.50 (s, 1H), 7.48 (d, J=7.8 Hz, 1H), 7.32 (dd, J=23.0, 8.2 Hz, 4H), 7.21 (t, J=7.6 Hz, 1H), 7.11 (s, 1H), 7.07 (q, J=7.5 Hz, 3H), 6.98 (t, J=7.5 Hz, 2H), 6.93 (s, 2H), 6.55 (d, J=7.5 Hz, 2H), 5.48 (q, J=7.8 Hz, 1H), 4.17 (q, J=7.3 Hz, 2H), 3.71 (s, 2H), 2.93 (s, 2H), 1.48 (t, J=7.3 Hz, 3H). ¹³C NMR (101 MHz, CDCl₃) δ 171.13, 156.85, 136.71, 136.28, 134.29, 130.63, 129.82, 129.33, 129.18, 128.75, 128.50, 128.27, 127.94, 127.17, 126.65, 126.49, 122.62, 121.83, 119.34, 119.23, 109.48, 107.69, 51.80, 42.09, 41.03, 33.62, 15.61.

Example 61. Preparation of (S)-2-(5-methoxy-1H-indol-3-yl)-N-(2-phenyl-1-(1-(4-chlorophenyl)-1H-imidazol-2-yl)ethyl)acetamide

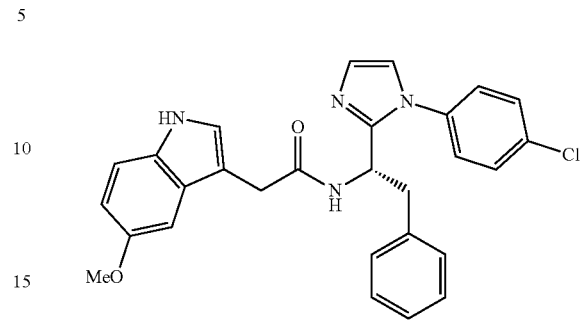

Using the general procedure described above, the title compound was prepared. ¹H NMR (400 MHz, CDCl₃) δ 8.81 (s, 1H), 7.47-7.39 (m, 1H), 7.31-7.19 (m, 3H), 7.18-7.11 (m, 2H), 7.08-7.00 (m, 3H), 6.97 (d, J=2.4 Hz, 1H), 6.83 (dt, J=8.8, 1.7 Hz, 1H), 6.82-6.68 (m, 3H), 6.70-6.61 (m, 2H), 5.16 (ddd, J=10.4, 8.2, 5.4 Hz, 1H), 3.81 (s, 3H), 3.70 (d, J=2.0 Hz, 2H), 3.14 (ddd, J=13.5, 10.5, 3.0 Hz, 1H), 2.99 (ddd, J=12.8, 5.6, 2.3 Hz, 1H). ¹³C NMR (101 MHz, CDCl₃) δ 171.80, 154.37, 148.30, 136.01, 135.47, 134.08, 131.69, 129.68, 129.29, 128.64, 127.66, 127.56, 127.02, 125.35, 124.93, 120.99, 112.77, 112.30, 108.18, 100.41, 56.05, 47.53, 41.65, 33.49. HRMS (ESI) m/z calcd for C₂₈H₂₅ClN₄O₂ [M+H]⁻ 483.1593, found 483.1598.

Example 62. Preparation of (S)-2-(5-methoxy-1H-indol-3-yl)-N-(2-phenyl-1-(1-(4-bromophenyl)-1H-imidazol-2-yl)ethyl)acetamide

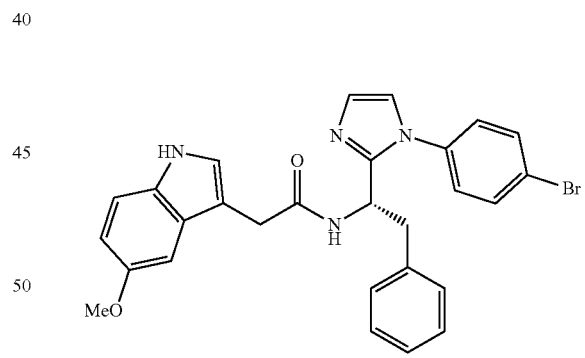

Using the general procedure described above, the title compound was prepared. ¹H NMR (600 MHz, CDCl₃) δ 8.50 (d, J=8.1 Hz, 1H), 8.25 (s, 1H), 7.48-7.43 (m, 3H), 7.38 (s, 1H), 7.24 (s, 1H), 7.18 (t, J=7.5 Hz, 1H), 7.10-7.04 (m, 3H), 6.83 (dd, J=8.9, 2.3 Hz, 2H), 6.73 (s, 2H), 6.68 (d, J=7.5 Hz, 2H), 5.20-5.13 (m, 1H), 3.85 (s, 3H), 3.82 (s, 1H), 3.74 (d, J=15.8 Hz, 1H), 3.58 (t, J=12.4 Hz, 1H), 3.12 (dd, J=13.1, 5.5 Hz, 1H). ¹³C NMR (100 MHz, CDCl₃) δ 173.04, 154.37, 149.03, 134.95, 133.16, 132.49, 131.53, 129.18, 129.11, 127.79, 127.63, 127.59, 125.53, 125.28, 121.53, 119.60, 112.60, 112.22, 108.14, 100.68, 56.24, 47.89, 40.50, 33.38. HRMS (ESI) m/z calcd for C₂₈H₂₅BrN₄O₂ [M+H]⁻ 527.1088, found 527.1092.

Example 63. Preparation of (S)-2-(5-methoxy-1H-indol-3-yl)-N-(2-phenyl-1-(1-(4-iodophenyl)-1H-imidazol-2-yl)ethyl)acetamide

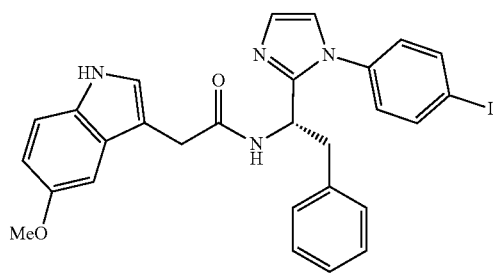 [SMILES: COc1ccc2[nH]cc(CC(=O)N[C@@H](Cc3ccccc3)c3nccn3-c3ccc(I)cc3)c2c1]

Using the general procedure described above, the title compound was prepared. ¹H NMR (400 MHz, CDCl₃) δ 8.47 (s, 1H), 7.92 (d, J=8.3 Hz, 1H), 7.63 (d, J=8.7 Hz, 2H), 7.27-7.20 (m, 3H), 7.16-7.05 (m, 1H), 7.09-6.98 (m, 3H), 6.83 (dd, J=8.8, 2.4 Hz, 1H), 6.73 (dd, J=8.8, 1.3 Hz, 1H), 6.70-6.63 (m, 2H), 6.55 (d, J=8.1 Hz, 2H), 5.17 (ddd, J=11.0, 8.2, 5.6 Hz, 1H), 3.83 (s, 3H), 3.77-3.64 (m, 2H), 3.33 (t, J=12.0 Hz, 1H), 3.09-2.94 (m, 1H). ¹³C NMR (100 MHz, CDCl₃) δ 172.33, 154.38, 148.55, 138.90, 135.53, 134.34, 131.60, 129.24, 128.84, 127.82, 127.73, 127.28, 125.17, 122.71, 121.12, 112.72, 112.25, 108.24, 100.54, 95.91, 56.14, 47.66, 41.12, 33.45. HRMS (ESI) m/z calcd for $C_{28}H_{25}IN_4O_2$ [M+H]⁻ 575.0949, found 575.0945.

Examples 64-75

Using the following general synthetic route, the compounds of Examples 64-75 were prepared.

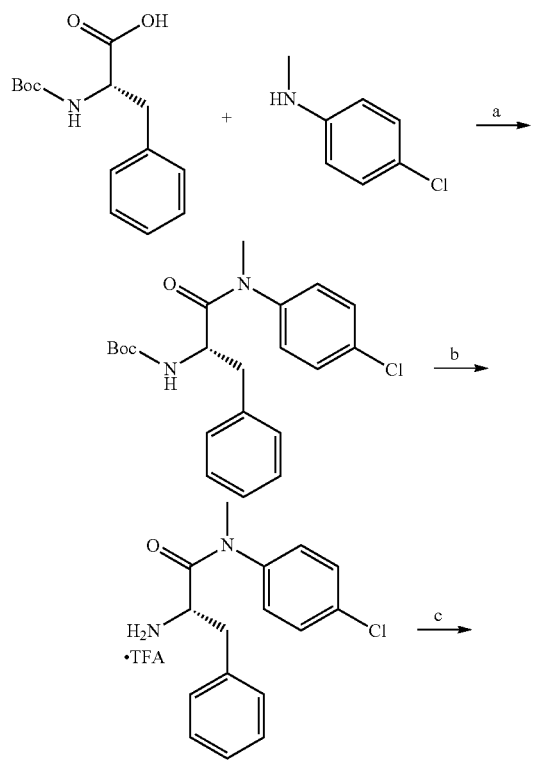

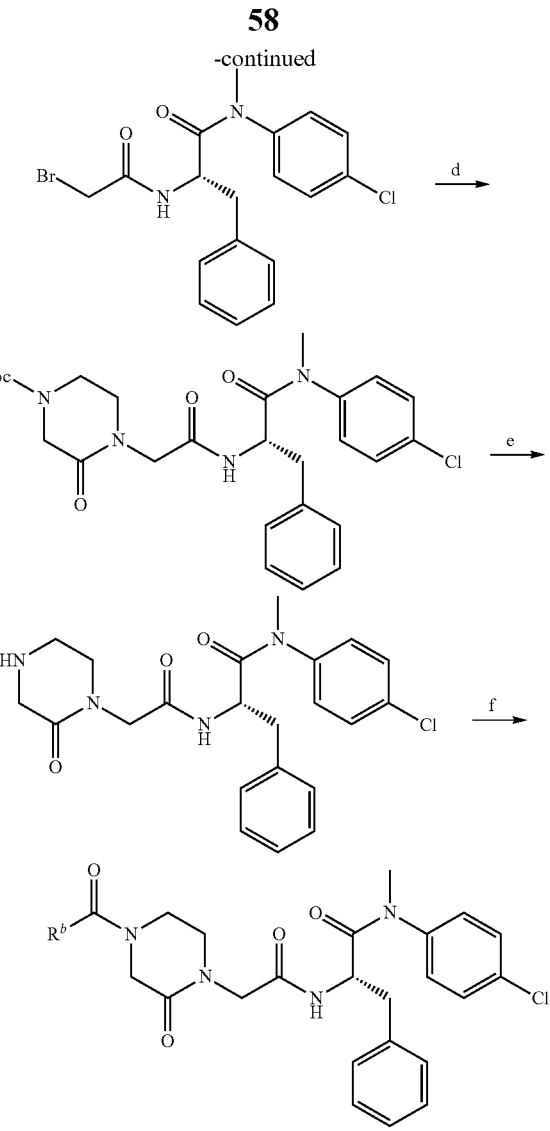

Example 64. Preparation of (S)—N-(4-chlorophenyl)-N-methyl-2-(2-(4-(2-nitrobenzoyl)-2-oxopiperazin-1-yl)acetamido)-3-phenylpropanamide

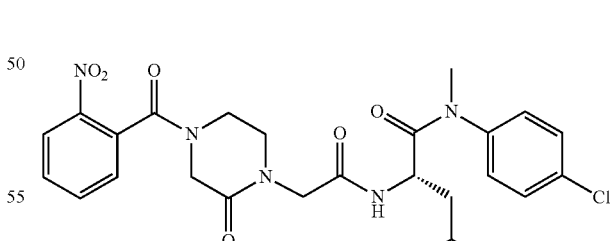

Using the general procedure described above, the title compound was prepared. Yield 95%. ¹H NMR (400 MHz, CDCl₃) δ 8.22-8.15 (m, 1H), 7.74 (t, J=7.5 Hz, 1H), 7.68-7.57 (m, 1H), 7.47-7.38 (m, 1H), 7.31-7.18 (m, 5H), 6.94 (dq, J=7.3, 3.6 Hz, 2H), 6.87-6.74 (m, 2H), 4.75 (dt, J=15.9, 7.8 Hz, 1H), 4.46 (s, 1H), 4.25-3.72 (m, 4H), 3.61-3.28 (m, 3H), 3.16 (s, 3H), 2.91 (dt, J=13.4, 8.3 Hz, 1H), 2.77 (dt, J=13.9, 7.1 Hz, 1H). $^{13}$C NMR (100 MHz, CDCl$_3$) δ 171.3, 167.0, 166.9, 165.1, 145.4, 140.9, 136.1, 135.0, 134.1, 131.8, 130.6, 130.0, 129.5, 128.8, 128.7, 128.1, 127.2, 125.1, 51.4, 50.3, 50.2, 46.8, 39.7, 39.2, 37.8. HRMS (ESI) m/z calcd for C$_{29}$H$_{28}$ClN$_5$O$_6$ [M–H]$^-$ 576.1655, found 576.1652.

Example 65. Preparation of (S)—N-(4-chlorophenyl)-N-methyl-2-(2-(4-(3-nitrobenzoyl)-2-oxopiperazin-1-yl)acetamido)-3-phenylpropanamide

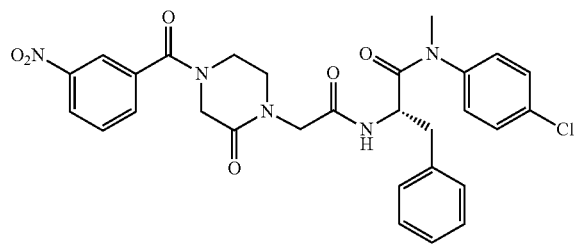 [SMILES: CN(C(=O)[C@H](Cc1ccccc1)NC(=O)CN1CCN(C(=O)c2cccc([N+](=O)[O-])c2)CC1=O)c1ccc(Cl)cc1]

Using the general procedure described above, the title compound was prepared. Yield 88%. $^1$H NMR (400 MHz, CDCl$_3$) δ 8.33 (dq, J=6.5, 2.0 Hz, 2H), 7.79 (dt, J=7.7, 1.4 Hz, 1H), 7.69-7.61 (m, 1H), 7.32-7.25 (m, 2H), 7.28-7.20 (m, 3H), 6.93 (dt, J=6.0, 3.4 Hz, 2H), 6.77 (d, J=9.2 Hz, 2H), 4.75 (q, J=7.6 Hz, 1H), 4.49-3.67 (m, 6H), 3.52-3.41 (m, 2H), 3.17 (s, 3H), 2.90 (dd, J=13.2, 7.7 Hz, 1H), 2.74 (dd, J=13.3, 6.9 Hz, 1H). $^{13}$C NMR (100 MHz, CDCl$_3$) δ 171.4, 167.6, 167.0, 165.2, 148.3, 140.9, 136.2, 135.9, 134.3, 133.4, 130.2, 130.1, 129.5, 128.8, 128.7, 127.2, 125.4, 122.7, 51.4, 50.1, 47.5, 39.4, 39.2, 37.9. HRMS (ESI) m/z calcd for C$_{29}$H$_{28}$ClN$_5$O$_6$ [M–H]$^-$ 576.1655, found 576.1669.

Example 66. Preparation of (S)—N-(4-chlorophenyl)-N-methyl-2-(2-(4-(4-nitrobenzoyl)-2-oxopiperazin-1-yl)acetamido)-3-phenylpropanamide

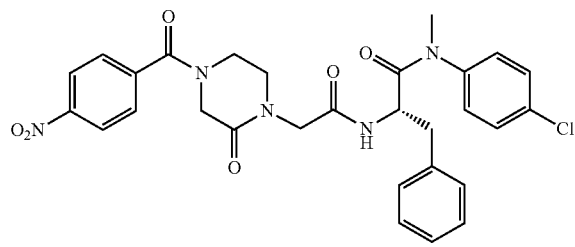 [SMILES: CN(C(=O)[C@H](Cc1ccccc1)NC(=O)CN1CCN(C(=O)c2ccc([N+](=O)[O-])cc2)CC1=O)c1ccc(Cl)cc1]

Using the general procedure described above, the title compound was prepared. Yield 92%. $^1$H NMR (400 MHz, CDCl$_3$) δ 8.34-8.26 (m, 2H), 7.63 (d, J=8.5 Hz, 2H), 7.32-7.19 (m, 5H), 6.92 (dd, J=6.6, 2.9 Hz, 2H), 6.76 (d, J=7.8 Hz, 2H), 4.75 (q, J=7.6 Hz, 1H), 4.42 (s, 1H), 4.23-3.84 (m, 4H), 3.60 (s, 1H), 3.49-3.42 (m, 2H), 3.17 (s, 3H), 2.90 (dd, J=13.3, 7.7 Hz, 1H), 2.74 (dd, J=13.3, 6.8 Hz, 1H). $^{13}$C NMR (100 MHz, CDCl$_3$) δ 171.9, 167.9, 166.9, 164.9, 148.9, 140.9, 140.6, 135.9, 134.3, 130.1, 129.7, 129.5, 128.8, 128.7, 127.6, 127.2, 124.2, 51.4, 50.1, 47.3, 44.4, 40.1, 39.2, 37.9. HRMS (ESI) m/z calcd for C$_{29}$H$_{28}$ClN$_5$O$_6$ [M–H]$^-$ 576.1655, found 576.1657.

Example 67. Preparation of (S)—N-(4-chlorophenyl)-N-methyl-2-(2-(2-oxo-4-(4-(trifluoromethyl)benzoyl)piperazin-1-yl)acetamido)-3-phenylpropanamide

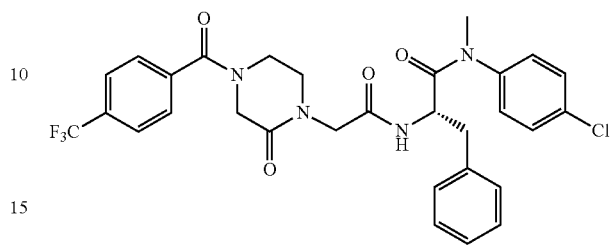

Using the general procedure described above, the title compound was prepared. Yield 98%. $^1$H NMR (400 MHz, CDCl$_3$) δ 7.71 (d, J=8.0 Hz, 2H), 7.56 (d, J=8.0 Hz, 2H), 7.32-7.19 (m, 4H), 6.93 (dd, J=6.6, 2.9 Hz, 2H), 6.76 (d, J=8.7 Hz, 3H), 4.75 (q, J=7.6 Hz, 1H), 4.56-3.77 (m, 5H), 3.62 (s, 1H), 3.42 (s, 2H), 3.17 (s, 3H), 2.90 (dd, J=13.3, 7.8 Hz, 1H), 2.74 (dd, J=13.2, 6.8 Hz, 1H). $^{13}$C NMR (100 MHz, CDCl$_3$) δ 171.3, 168.8, 167.0, 165.8, 140.9, 138.1, 135.9, 134.3, 132.55 (d, J=32.9 Hz), 130.1, 129.5, 128.8, 128.7, 127.8 (d, J=9.9 Hz), 127.2, 125.94 (q, J=3.7 Hz), 125.00, 51.4, 50.2, 47.3, 39.7, 39.2, 37.9. HRMS (ESI) m/z calcd for C$_{30}$H$_{28}$ClF$_3$N$_4$O$_4$ [M–H]$^-$ 599.1678, found 599.1684.

Example 68. Preparation of (S)-2-(2-(4-(2-aminobenzoyl)-2-oxopiperazin-1-yl)acetamido)-N-(4-chlorophenyl)-N-methyl-3-phenylpropanamide

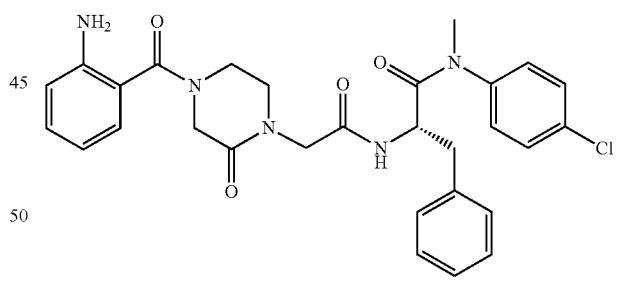

Using the general procedure described above, the title compound was prepared. Yield 39%. $^1$H NMR (600 MHz, CD$_3$OD) δ 7.33 (d, J=8.3 Hz, 2H), 7.28-7.19 (m, 4H), 7.16-7.09 (m, 1H), 6.98-6.93 (m, 2H), 6.88 (s, 2H), 6.79 (d, J=8.1 Hz, 1H), 6.70 (t, J=7.4 Hz, 1H), 4.63 (t, J=7.6 Hz, 1H), 4.29-4.26 (m, 2H), 4.09 (d, J=5.8 Hz, 2H), 3.78 (s, 2H), 3.42-3.33 (m, 2H), 3.15 (d, J=1.7 Hz, 3H), 2.97 (dd, J=13.4, 7.9 Hz, 1H), 2.77 (dd, J=13.3, 7.1 Hz, 1H). $^{13}$C NMR (100 MHz, CDCl$_3$) δ 171.6, 168.6, 167.4, 166.1, 152.3, 151.3, 144.8, 141.0, 136.3, 134.1, 131.7, 129.9, 129.5, 128.9, 128.7, 128.2, 127.1, 120.9, 51.8, 51.7, 50.5, 47.7, 38.8, 37.9. HRMS (ESI) m/z calcd for C$_{29}$H$_{30}$ClN$_5$O$_4$ [M–H]$^-$ 546.1914, found 546.1911.

Example 69. Preparation of (S)-2-(2-(4-(3-amino-benzoyl)-2-oxopiperazin-1-yl)acetamido)-N-(4-chlorophenyl)-N-methyl-3-phenylpropanamide

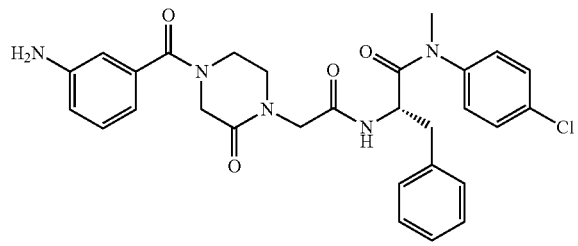 [SMILES: CN(C(=O)[C@H](Cc1ccccc1)NC(=O)CN1CCN(C(=O)c2cccc(N)c2)CC1=O)c1ccc(Cl)cc1]

Using the general procedure described above, the title compound was prepared. Yield 53%. ¹H NMR (600 MHz, CD₃OD) δ 7.33 (d, J=8.3 Hz, 2H), 7.23 (d, J=5.6 Hz, 3H), 7.18 (t, J=7.7 Hz, 1H), 6.97-6.93 (m, 2H), 6.88 (s, 2H), 6.83-6.78 (m, 1H), 6.75 (s, 1H), 6.71 (d, J=7.4 Hz, 1H), 4.63 (t, J=7.6 Hz, 1H), 4.33 (s, 1H), 4.07 (d, J=16.5 Hz, 3H), 3.96 (s, 1H), 3.70 (s, 1H), 3.31 (s, 2H), 3.15 (d, J=2.0 Hz, 3H), 2.97 (dd, J=13.3, 7.8 Hz, 1H), 2.77 (dd, J=13.3, 7.0 Hz, 1H). ¹³C NMR (100 MHz, CDCl₃) δ 171.4, 169.9, 167.4, 166.1, 154.5, 151.8, 150.5, 140.9, 139.2, 136.1, 134.3, 130.1, 129.5, 128.9, 128.7, 127.2, 122.4, 51.9, 50.3, 47.9, 41.7, 38.8, 38.0. HRMS (ESI) m/z calcd for C₂₉H₃₀ClN₅O₄ [M–H]⁻ 546.1914, found 546.1918.

Example 70. Preparation of (S)-2-(2-(4-(4-amino-benzoyl)-2-oxopiperazin-1-yl)acetamido)-N-(4-chlorophenyl)-N-methyl-3-phenylpropanamide

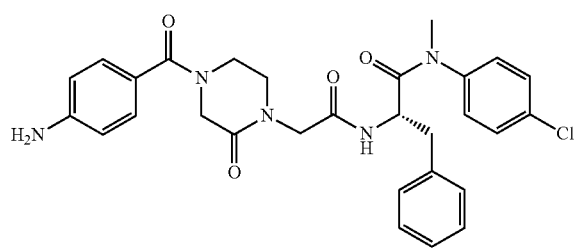 [SMILES: CN(C(=O)[C@H](Cc1ccccc1)NC(=O)CN1CCN(C(=O)c2ccc(N)cc2)CC1=O)c1ccc(Cl)cc1]

Using the general procedure described above, the title compound was prepared. Yield 62%. ¹H NMR (600 MHz, CDCl₃) δ 7.37 (d, J=7.9 Hz, 2H), 7.30 (d, J=8.3 Hz, 2H), 7.25-7.20 (m, 3H), 6.99 (d, J=7.8 Hz, 2H), 6.95-6.91 (m, 2H), 6.85-6.81 (m, 2H), 4.68 (p, J=7.4 Hz, 1H), 4.28 (s, 2H), 4.22 (d, J=15.9 Hz, 1H), 3.87 (dd, J=27.0, 11.4 Hz, 3H), 3.50-3.38 (m, 2H), 3.18 (s, 3H), 2.92 (dd, J=13.4, 7.2 Hz, 1H), 2.83 (dd, J=13.4, 7.3 Hz, 1H). HRMS (ESI) m/z calcd for C₂₉H₃₀ClN₅O₄ [M–H]⁻ 546.1914, found 546.1914.

Example 71. Preparation of (S)-2-(2-(4-benzoyl-2-oxopiperazin-1-yl)acetamido)-N-(4-chlorophenyl)-N-methyl-3-phenylpropanamide

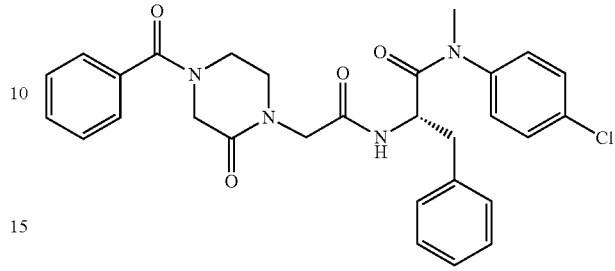

Using the general procedure described above, the title compound was prepared. Yield 94%. ¹H NMR (400 MHz, CDCl₃) δ 7.43 (q, J=4.6, 3.3 Hz, 5H), 7.29 (d, J=1.6 Hz, 1H), 7.28 (d, J=1.5 Hz, 1H), 7.24-7.21 (m, 3H), 6.92 (h, J=4.1 Hz, 2H), 6.76 (d, J=8.7 Hz, 2H), 4.79-4.68 (m, 1H), 4.27 (s, 2H), 4.14-3.61 (m, 4H), 3.39 (s, 2H), 3.17 (s, 3H), 2.89 (dd, J=13.2, 7.7 Hz, 1H), 2.74 (dd, J=13.2, 6.9 Hz, 1H). ¹³C NMR (100 MHz, CDCl₃) δ 171.3, 170.3, 167.1, 165.9, 140.9, 136.0, 134.5, 134.2, 130.7, 130.1, 129.5, 128.82, 128.78, 128.7, 127.4, 127.2, 51.3, 51.2, 50.2, 47.6, 39.2, 37.8. HRMS (ESI) m/z calcd for C₂₉H₂₉ClN₄O₄ [M–H]⁻ 531.1805, found 531.1811.

Example 72. Preparation of (S)—N-(4-chlorophenyl)-2-(2-(4-(2-hydroxybenzoyl)-2-oxopiperazin-1-yl)acetamido)-N-methyl-3-phenylpropanamide

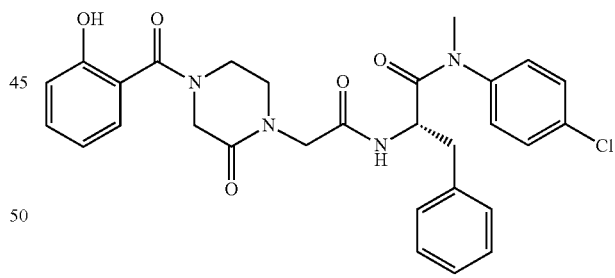

Using the general procedure described above, the title compound was prepared. Yield 64%. ¹H NMR (600 MHz, CDCl₃) δ 7.38-7.27 (m, 4H), 7.27-7.20 (m, 3H), 7.04 (d, J=8.2 Hz, 1H), 6.98-6.92 (m, 3H), 6.86 (d, J=9.0 Hz, 1H), 6.67 (s, 1H), 4.84 (q, J=8.2 Hz, 1H), 4.41 (s, 2H), 4.29-4.23 (m, 1H), 4.11-4.02 (m, 1H), 3.62 (dt, J=13.7, 6.1 Hz, 2H), 3.47 (ddd, J=12.6, 8.9, 4.5 Hz, 1H), 3.32 (d, J=4.5 Hz, 1H), 3.18 (s, 3H), 2.94 (dd, J=13.2, 8.5 Hz, 1H), 2.75 (dd, J=13.2, 7.1 Hz, 1H). ¹³C NMR (100 MHz, CDCl₃) δ 172.4, 169.1, 166.9, 166.8, 166.4, 140.4, 135.7, 134.6, 132.3, 129.6, 128.8, 128.7, 128.6, 127.3, 120.3, 116.7, 51.0, 50.9, 50.8, 48.1, 39.44, 39.41, 38.0. HRMS (ESI) m/z calcd for C₂₉H₂₉ClN₄O₄ [M–H]⁻ 547.1754, found 547.1759.

Example 73. Preparation of (S)—N-(4-chlorophenyl)-2-(2-(4-(3-hydroxybenzoyl)-2-oxopiperazin-1-yl)acetamido)-N-methyl-3-phenylpropanamide

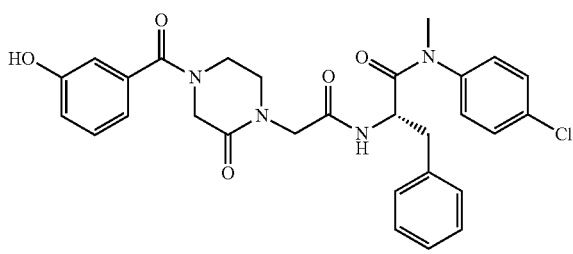 [SMILES: CN(C(=O)[C@H](Cc1ccccc1)NC(=O)CN1CCN(C(=O)c2cccc(O)c2)CC1=O)c1ccc(Cl)cc1]

Using the general procedure described above, the title compound was prepared. Yield 50%. $^1$H NMR (600 MHz, CDCl$_3$) δ 7.33-7.24 (m, 6H), 7.02-6.93 (m, 4H), 6.90 (s, 1H), 6.78 (s, 2H), 4.77 (q, J=7.6 Hz, 1H), 4.52-4.13 (m, 4H), 3.92 (d, J=15.6 Hz, 2H), 3.43 (d, J=51.4 Hz, 2H), 3.20 (s, 3H), 2.94 (dd, J=13.4, 8.0 Hz, 1H), 2.79 (dd, J=13.4, 6.7 Hz, 1H). $^{13}$C NMR (100 MHz, CDCl$_3$) δ 171.8, 170.4, 167.5, 166.2, 157.2, 140.7, 135.8, 135.3, 134.4, 130.4, 130.1, 129.5, 128.8, 128.7, 127.4, 118.6, 118.1, 114.3, 53.6, 51.5, 50.5, 47.8, 39.1, 38.1. HRMS (ESI) m/z calcd for C$_{29}$H$_{29}$ClN$_4$O$_4$ [M−H]$^-$ 547.1754, found 547.1754.

Example 74. Preparation of (S)-3-(4-(2-((1-((4-chlorophenyl)(methyl)amino)-1-oxo-3-phenylpropan-2-yl)amino)-2-oxoethyl)-3-oxopiperazine-1-carbonyl)benzenesulfonyl fluoride

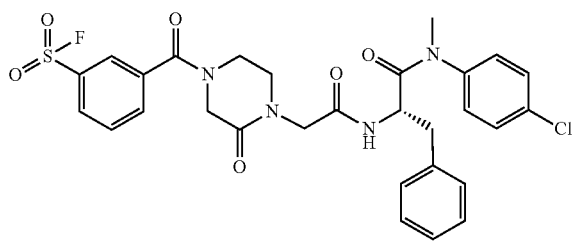 [SMILES: CN(C(=O)[C@H](Cc1ccccc1)NC(=O)CN1CCN(C(=O)c2cccc(S(=O)(=O)F)c2)CC1=O)c1ccc(Cl)cc1]

Using the general procedure described above, the title compound was prepared. Yield 61%. $^1$H NMR (400 MHz, CDCl$_3$) δ 8.14-8.08 (m, 2H), 7.86 (dt, J=7.7, 1.5 Hz, 1H), 7.74 (t, J=7.9 Hz, 1H), 7.32-7.19 (m, 5H), 6.93 (p, J=3.2, 2.5 Hz, 2H), 6.77 (d, J=8.1 Hz, 3H), 4.74 (q, J=7.5 Hz, 1H), 4.54-3.65 (m, 6H), 3.44 (s, 2H), 3.17 (s, 3H), 2.89 (dd, J=13.3, 7.7 Hz, 1H), 2.73 (dd, J=13.3, 6.9 Hz, 1H). $^{13}$C NMR (100 MHz, CDCl$_3$) δ 171.4, 167.2, 167.0, 164.7, 140.8, 136.5, 135.9, 134.4, 134.3, 134.0 (d, J=25.6 Hz), 130.4, 130.2, 130.1, 129.5, 128.8, 128.7, 127.6, 127.2, 51.4, 50.1, 47.2, 39.1, 37.9. HRMS (ESI) m/z calcd for C$_{29}$H$_{28}$ClFN$_4$O$_6$S [M−H]$^-$ 613.1329, found 613.1331.

Example 75. Preparation of (S)-4-(4-(2-((1-((4-chlorophenyl)(methyl)amino)-1-oxo-3-phenylpropan-2-yl)amino)-2-oxoethyl)-3-oxopiperazine-1-carbonyl)benzenesulfonyl fluoride

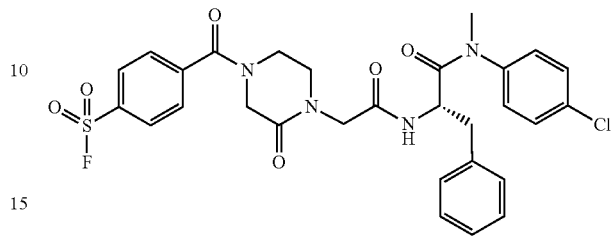

Using the general procedure described above, the title compound was prepared. Yield 53%. $^1$H NMR (400 MHz, CDCl$_3$) δ 8.10 (d, J=8.1 Hz, 2H), 7.70 (d, J=8.0 Hz, 2H), 7.32-7.20 (m, 5H), 6.92 (dd, J=6.6, 2.9 Hz, 2H), 6.76 (s, 3H), 4.75 (q, J=7.5 Hz, 1H), 4.43 (s, 1H), 4.22-3.86 (m, 4H), 3.59 (s, 1H), 3.44 (s, 2H), 3.17 (s, 3H), 2.89 (dd, J=13.3, 7.7 Hz, 1H), 2.73 (dd, J=13.2, 6.8 Hz, 1H). $^{13}$C NMR (101 MHz, CDCl$_3$) δ 171.4, 167.5, 166.9, 165.4, 140.8, 135.9, 134.8 (d, J=25.5 Hz), 134.3, 130.6, 130.1, 129.5, 129.1, 128.8, 128.7, 127.2, 124.3, 51.4, 50.0, 47.8, 39.1, 37.9. HRMS (ESI) m/z calcd for C$_{29}$H$_{28}$ClFN$_4$O$_6$S [M−H]$^-$ 613.1329, found 613.1326.

Example 76. Anti-HIV-1 Activity, Cytotoxicity, and CA Hexamer Stability Profiles for Representative Compounds of the Invention Anti-HIV-1 and Cytotoxicity Assays Anti-HIV-1 activity of PF74 and representative compounds of the invention were examined in TZM-GFP cells. The potency of HIV-1 inhibition by a compound was based on its inhibitory effect on viral LTR-activated GFP expression compared with that of compound-free (DMSO) controls. Briefly, TZM-GFP cells were plated at density of 1×10$^4$ cells per well in a 96-well plate. 24 hours later, media was replaced with increasing concentrations of compound. 24 hours post treatment, cells were exposed to an HIV-1 strain (MOI=1). After incubation for 48 hours, anti-HIV-1 activity was assessed by counting the number of GFP positive cells on a Cytation™ 5 Imaging Reader (BioTek) and 50% effective concentration (EC$_{50}$) values were determined.

The cytotoxicity of each compound was also determined in TZM-GFP cells. Cells were plated at a density of 1×10$^4$ cells per well in a 96-well plate and were continuously exposed to increasing concentrations of a compound for 72 hours. The number of viable cells in each well was determined using a Cell Proliferation Kit II (XTT), and 50% cytotoxicity concentration (CC$_{50}$) values were determined. All the cell-based assays were conducted in duplicate and in at least two independent experiments. For the EC$_{50}$ and CC$_{50}$ dose responses, values were plotted in GraphPad Prism 5 and analyzed with the log (inhibitor) vs. normalized response-variable slope equation. Final values were calculated in each independent assay and the average values were determined. Statistical analysis (calculation of standard deviation) was performed by using Microsoft Excel.

Thermal Shift Assays (TSAs)

Compounds were screened for their effect on CA stability using purified covalently-crosslinked hexameric CA$^{A14C/E45C/W184A/M185A}$ (CA121). CA121 cloned in a pET11a expression plasmid was kindly provided by Dr. Owen Pornillos (University of Virginia, Charlottesville, VA). Protein was expressed in *E. coli* BL21(DE3)RIL and purified as reported previously (Pornillos, O., et al., *Cell* 2009, 137, 1282-1292). The TSA has been previously described (Lo, M.-C., et al., *Anal. Biochem.* 2004, 332, 153-159; Miyazaki, Y., et al., *Front. Microbiol.* 2017, 8, 1413; and Pantoliano, M. W., et al., *J. Biomol. Screen.* 2001, 6, 429-440). Briefly, the TSA was conducted on the PikoReal Real-Time PCR System (Thermo Fisher Scientific) or the QuantStudio 3 Real-Time PCR system (Thermo Fisher Scientific). Each reaction contained 10 μL of 15 μM CA121 in 50 mM sodium phosphate buffer (pH 8.0), 10 μL of 2× Sypro Orange Protein Gel Stain (Life Technologies) in 50 mM sodium phosphate buffer (pH 8.0) and 0.2 μL of DMSO (control) or compound. Compounds were tested at a final concentration of 20 μM. The plate was heated from 25 to 95° C. with a heating rate of 0.2° C./10 sec. The fluorescence intensity was measured with an Ex range of 475-500 nm and Em range of 520-590 nm. The differences in the melting temperature ($\Delta T_m$) of CA hexamer in DMSO ($T_0$) verses in the presence of compound ($T_m$) were calculated using the following formula: $\Delta T_m = T_m - T_0$.

Data for representative compounds of the invention is provided in the following table.

TABLE

Anti-HIV-1 activity, cytotoxicity, and CA hexamer stability profiles for representative compounds of the invention.

| Example | $EC_{50}$ (μM) or % inhibition at 2/20 μM | $CC_{50}$ (μM) | TSA $\Delta Tm$ (° C.) |
|---|---|---|---|
| | 0/91 | >50 | −1.2 |
| | 17/96 | ~50 | −0.4 |
| | 3.3 ± 0.3 | >100 | −1.7 |
| | 0/93 | >50 | −0.9 |

TABLE-continued
Anti-HIV-1 activity, cytotoxicity, and CA hexamer stability profiles for representative compounds of the invention.
| Example | EC$_{50}$ (μM) or % inhibition at 2/20 μM | CC$_{50}$ (μM) | TSA ΔTm (° C.) |
| --- | --- | --- | --- |
| 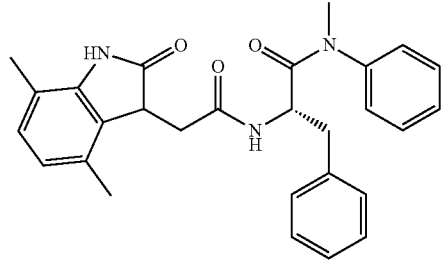 | 4.9 ± 0.3 | >100 | −1.8 |
| 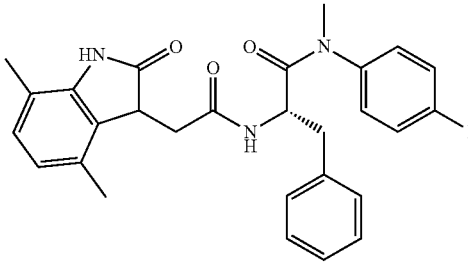 | 5.4 ± 0.5 | >100 | −1.7 |
| 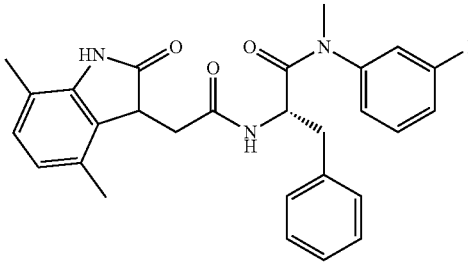 | 5.2 ± 0.4 | 60 ± 6 | −1.8 |
| 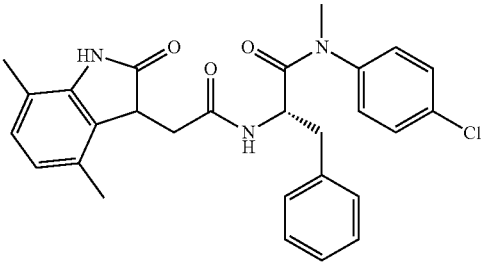 [SMILES: Cc1cccc2c1NC(=O)C2CC(=O)N[C@@H](Cc1ccccc1)C(=O)N(C)c1ccc(Cl)cc1] | 2.8 ± 0.1 | 63 ± 13 | −1.3 |
| 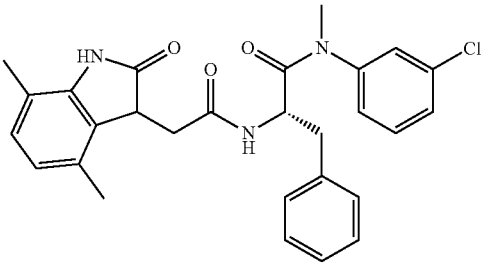 [SMILES: Cc1ccc(C)c2c1NC(=O)C2CC(=O)N[C@@H](Cc1ccccc1)C(=O)N(C)c1cccc(Cl)c1] | 2.1 ± 0.2 | 43 ± 2 | −2.4 |

TABLE-continued
Anti-HIV-1 activity, cytotoxicity, and CA hexamer stability profiles for representative compounds of the invention.
| Example | EC$_{50}$ (μM) or % inhibition at 2/20 μM | CC$_{50}$ (μM) | TSA ΔTm (° C.) |
|---|---|---|---|
| 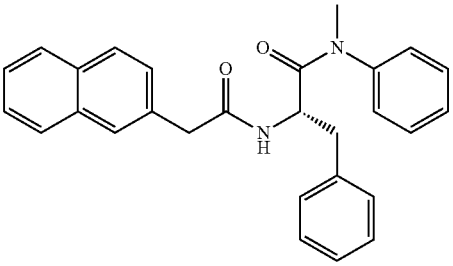 [SMILES: CN(C(=O)[C@H](Cc1ccccc1)NC(=O)Cc1ccc2ccccc2c1)c1ccccc1] | 40/98 | <50 | 4.8 |
| 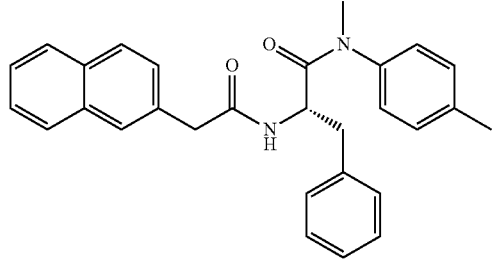 [SMILES: Cc1ccc(N(C)C(=O)[C@H](Cc2ccccc2)NC(=O)Cc2ccc3ccccc3c2)cc1] | 0.99 ± 0.005 | <50 | 6.4 |
| 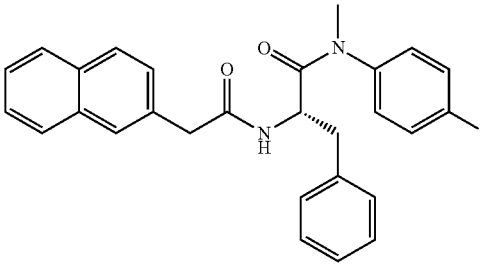 | 0.63 ± 0.02 | <50 | 7.0 |
| 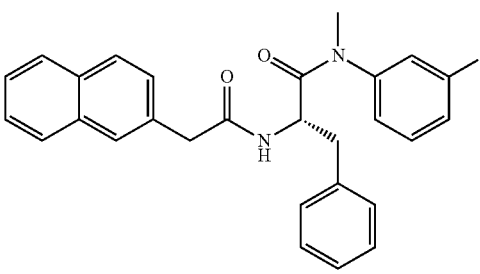 | 0/94 | <50 | 4.3 |
| 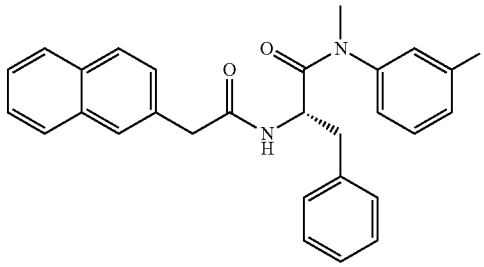 | 0/97 | <50 | 5.2 |

TABLE-continued

Anti-HIV-1 activity, cytotoxicity, and CA hexamer stability profiles for representative compounds of the invention.

| Example | EC$_{50}$ (μM) or % inhibition at 2/20 μM | CC$_{50}$ (μM) | TSA ΔTm (° C.) |
| --- | --- | --- | --- |
| *(2-naphthyl-CH$_2$-C(O)-NH-CH(CH$_2$Ph)-C(O)-N(Et)(Ph))* | 46/97 | <50 | 4.3 |
| *(1-naphthyl-CH$_2$-C(O)-NH-CH(CH$_2$Ph)-C(O)-N(Me)(Ph))* | 1.1 ± 0.04 | <50 | 6.0 |
| *(1-naphthyl-CH$_2$-C(O)-NH-CH(CH$_2$Ph)-C(O)-N(Me)(4-Me-C$_6$H$_4$))* | 1.0 ± 0.2 | <50 | 5.7 |
| *(1-naphthyl-CH$_2$-C(O)-NH-CH(CH$_2$Ph)-C(O)-N(Me)(4-Cl-C$_6$H$_4$))* | 0.83 ± 0.03 | <50 | 7.2 |
| *(1-naphthyl-CH$_2$-C(O)-NH-CH(CH$_2$Ph)-C(O)-N(Me)(3-Cl-C$_6$H$_4$))* | 53/96 | <50 | 4.4 |

TABLE-continued

Anti-HIV-1 activity, cytotoxicity, and CA hexamer stability profiles for representative compounds of the invention.

| Example | EC$_{50}$ (μM) or % inhibition at 2/20 μM | CC$_{50}$ (μM) | TSA ΔTm (° C.) |
|---|---|---|---|
| [structure: naphthalene-CH$_2$-C(O)-NH-CH(CH$_2$Ph)-C(O)-N(CH$_3$)-(3-fluorophenyl)] | 44/97 | <50 | 5.4 |
| [structure: naphthalene-CH$_2$-C(O)-NH-CH(CH$_2$Ph)-C(O)-N(Et)-phenyl] | 1.8 ± 0.09 | <50 | 4.9 |
| [structure: cyclohexane-spiro-hydantoin-N-CH$_2$-C(O)-NH-CH(CH$_2$Ph)-C(O)-N(CH$_3$)-phenyl] | 8.9 ± 1.5 | >100 | 1.3 |
| [structure: cyclohexane-spiro-hydantoin-N-CH$_2$-C(O)-NH-CH(CH$_2$Ph)-C(O)-N(CH$_3$)-(4-methoxyphenyl)] | 5.1 ± 2 | >100 | 1.8 |
| [structure: cyclohexane-spiro-hydantoin-N-CH$_2$-C(O)-NH-CH(CH$_2$Ph)-C(O)-N(CH$_3$)-(4-methylphenyl)] | 1.9 ± 0.5 | >100 | 2.7 |

TABLE-continued

Anti-HIV-1 activity, cytotoxicity, and CA hexamer stability profiles for representative compounds of the invention.

| Example | EC$_{50}$ (μM) or % inhibition at 2/20 μM | CC$_{50}$ (μM) | TSA ΔTm (° C.) |
| --- | --- | --- | --- |
| *[structure with 4-F phenyl]* | 9/99 | >50 | 3.1 |
| *[structure with 3-F phenyl]* | 24/98 | >50 | 1.3 |
| *[structure with 4-Cl phenyl]* | 2.5 ± 0.5 | >100 | 2.2 |
| *[structure with 3-Cl phenyl]* | 9/98 | <50 | 3.3 |
| *[structure with 3-Br phenyl]* | >20 | >50 | 1.5 |

TABLE-continued

Anti-HIV-1 activity, cytotoxicity, and CA hexamer stability profiles for representative compounds of the invention.

| Example | EC$_{50}$ (μM) or % inhibition at 2/20 μM | CC$_{50}$ (μM) | TSA ΔTm (° C.) |
|---|---|---|---|
| *[spirocyclohexyl hydantoin-Gly-Phe-N(Et)(Ph) structure]* | 7.6 ± 0.9 | >100 | 2.0 |
| *[quinazoline-2,4-dione-Gly-Phe-N(Me)(Ph) structure]* | 6.9 ± 0.8 | >100 | 2.7 |
| *[quinazoline-2,4-dione-Gly-Phe-N(Me)(4-F-Ph) structure]* | 8.0 ± 1.3 | >100 | 2.4 |
| *[quinazoline-2,4-dione-Gly-Phe-Pro-NHPh structure]* | 1.6 ± 0.1 | >100 | 2.5 |
| *[benzoyl-Gly-Phe-N(Me)(Ph) structure]* | 15/96 | >50 | 1.3 |

TABLE-continued

Anti-HIV-1 activity, cytotoxicity, and CA hexamer stability profiles for representative compounds of the invention.

| Example | EC$_{50}$ (μM) or % inhibition at 2/20 μM | CC$_{50}$ (μM) | TSA ΔTm (° C.) |
|---|---|---|---|
| *[benzamido-Gly-Phe-N(CH$_3$)-(4-methylphenyl)]* | 1.6 ± 0.02 | >50 | 5.0 |
| *[benzamido-Gly-Phe-N(CH$_3$)-(4-chlorophenyl)]* | 0.88 ± 0.02 | >50 | 4.1 |
| *[benzamido-Gly-Phe-N(CH$_3$)-(3-chlorophenyl)]* | 40/95 | >50 | 2.0 |
| *[benzamido-Gly-Phe-N(CH$_3$)-(4-fluorophenyl)]* | 12/97 | >50 | 2.2 |
| *[benzamido-Gly-Phe-N(CH$_3$)-(3-fluorophenyl)]* | 3/94 | >50 | 0 |

TABLE-continued

Anti-HIV-1 activity, cytotoxicity, and CA hexamer stability profiles for representative compounds of the invention.

| Example | EC$_{50}$ (μM) or % inhibition at 2/20 μM | CC$_{50}$ (μM) | TSA ΔTm (° C.) |
|---|---|---|---|
| (structure) | 38/97 | >50 | 2.2 |
| (structure) | 2.5 ± 0.03 | >50 | −2.5 |
| (structure) | 35/95 | >50 | 0.5 |
| (structure) | 7/85 | >50 | 0.6 |
| (structure) | 1.7 ± 0.2 | >50 | 1.7 |

TABLE-continued

Anti-HIV-1 activity, cytotoxicity, and CA hexamer stability profiles for representative compounds of the invention.

| Example | EC$_{50}$ (μM) or % inhibition at 2/20 μM | CC$_{50}$ (μM) | TSA ΔTm (° C.) |
|---|---|---|---|
| [structure: thymine-CH₂-C(O)-NH-CH(CH₂Ph)-C(O)-N(CH₃)-(3-chlorophenyl)] | 37/95 | >50 | 0.6 |
| [structure: thymine-CH₂-C(O)-NH-CH(CH₂Ph)-C(O)-N(CH₃)-(4-fluorophenyl)] | 6/94 | >50 | 0 |
| [structure: thymine-CH₂-C(O)-NH-CH(CH₂Ph)-C(O)-N(CH₃)-(3-fluorophenyl)] | 0/74 | >50 | 0.9 |
| [structure: thymine-CH₂-C(O)-NH-CH(CH₂Ph)-C(O)-N(CH₃)-(3-bromophenyl)] | 22/99.7 | >50 | 0.5 |
| [structure: 2-methylindole-CH₂-C(O)-NH-CH(CH₂Ph)-(3-phenylpyridin-2-yl)] | 2.6 ± 0.4 | <50 (% viability at 50 μM = 29 ± 12) | 4.5 |

TABLE-continued

Anti-HIV-1 activity, cytotoxicity, and CA hexamer stability profiles for representative compounds of the invention.

| Example | EC$_{50}$ (μM) or % inhibition at 2/20 μM | CC$_{50}$ (μM) | TSA ΔTm (° C.) |
|---|---|---|---|
| (indazole-CH$_2$-C(O)NH-CH(CH$_2$Ph)-(3-phenylpyridin-2-yl)) | 8.8 ± 0.4 | <50 (% viability at 50 μM = 46 ± 13) | 1.0 |
| (pyrazole-CH$_2$-C(O)NH-CH(CH$_2$Ph)-(3-phenylpyridin-2-yl)) | 5.1 ± 0.7 | >50 (% viability at 50 μM = 102 ± 6) | 1.1 |
| (2-methylindole-CH$_2$-C(O)NH-CH(CH$_2$Ph)-(1-phenylimidazol-2-yl)) | 3.7 ± 0.8 | >50 (% viability at 50 μM = 78 ± 6) | 3.9 |
| (2-methylindole-CH$_2$-C(O)NH-CH(CH$_2$Ph)-(1-(4-cyanophenyl)imidazol-2-yl)) | 6.6 ± 0.4 | >50 (% viability at 50 μM = 87 ± 8) | 2.2 |
| (indole-CH$_2$-C(O)NH-CH(CH$_2$Ph)-(3-(4-chlorophenyl)pyridin-2-yl)) | 0.79 ± 0.25 | 22 ± 2 | 7.7 ± 0.2 |

TABLE-continued

Anti-HIV-1 activity, cytotoxicity, and CA hexamer stability profiles for representative compounds of the invention.

| Example | EC$_{50}$ (µM) or % inhibition at 2/20 µM | CC$_{50}$ (µM) | TSA ΔTm (° C.) |
|---|---|---|---|
| 5-methoxyindole-CH$_2$-C(O)-NH-CH(CH$_2$Ph)-(2-(3-(4-chlorophenyl)pyridinyl)) | 1.4 ± 0.7 | 39 ± 0.2 | 7.8 ± 0.3 |
| 5-hydroxyindole-CH$_2$-C(O)-NH-CH(CH$_2$Ph)-(2-(3-(4-chlorophenyl)pyridinyl)) | 0.31 ± 0.07 | 44 ± 1 | 8.7 ± 0.3 |
| 1-ethylindole-CH$_2$-C(O)-NH-CH(CH$_2$Ph)-(2-(3-(4-chlorophenyl)pyridinyl)) | 2.7 ± 0.2 | 41 ± 0.1 | 6.6 ± 0.2 |
| 1-ethyl-5-methoxyindole-CH$_2$-C(O)-NH-CH(CH$_2$Ph)-(2-(3-(4-chlorophenyl)pyridinyl)) | 3.6 ± 0.2 | 48 ± 6 | 5.9 ± 0.2 |
| 5-methoxyindole-CH$_2$-C(O)-NH-CH(CH$_2$Ph)-(2-(3-(4-bromophenyl)pyridinyl)) | 2.1 ± 0.8 | 40 ± 4 | 6.3 ± 0.6 |

TABLE-continued

Anti-HIV-1 activity, cytotoxicity, and CA hexamer stability profiles for representative compounds of the invention.

| Example | EC$_{50}$ (µM) or % inhibition at 2/20 µM | CC$_{50}$ (µM) | TSA ΔTm (° C.) |
|---|---|---|---|
| 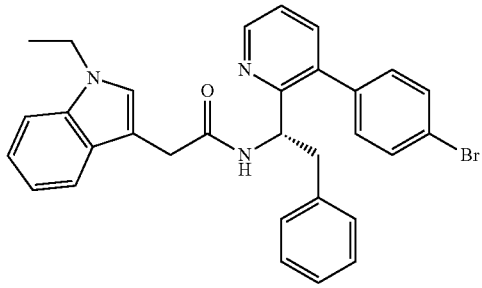 [SMILES: CCn1cc(CC(=O)N[C@@H](Cc2ccccc2)c2ncccc2-c2ccc(Br)cc2)c2ccccc21] | 3.2 ± 0.3 | 41 ± 2 | 6.3 ± 0.1 |
| 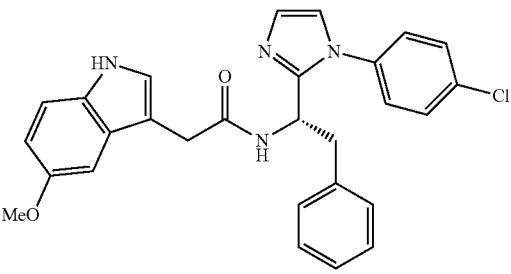 [SMILES: COc1ccc2[nH]cc(CC(=O)N[C@@H](Cc3ccccc3)c3nccn3-c3ccc(Cl)cc3)c2c1] | 3.3 ± 0.03 | 93 ± 2 | 4.0 ± 0.3 |
| 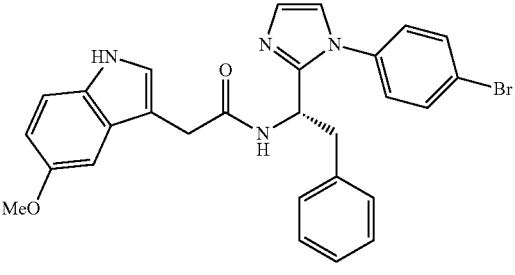 [SMILES: COc1ccc2[nH]cc(CC(=O)N[C@@H](Cc3ccccc3)c3nccn3-c3ccc(Br)cc3)c2c1] | 3.5 ± 0.3 | >100 | 2.8 ± 0.3 |
| 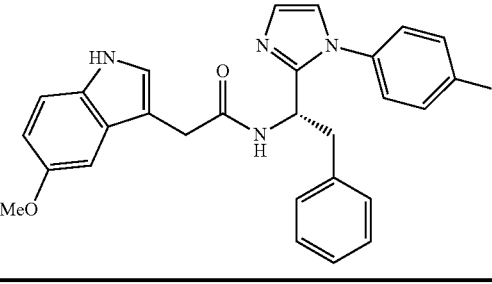 | 3.3 ± 0.2 | >100 | 2.7 ± 0.1 |

Example 77. Metabolic Stability in Liver Microsomes for Representative Compounds of the Invention Microsomal Stability Assay.

The in vitro microsomal stability assay was conducted in duplicate in mouse and human liver microsomal systems, which were supplemented with nicotinamide adenine dinucleotide phosphate (NADPH) as a cofactor. Briefly, a compound (1 µM final concentration) was pre-incubated, in the absence or presence of 0.5 µM Cobicistat (CYP 3A inhibitor, purchased from medchemexpress.com and verified with LCMS), with the reaction mixture containing liver microsomal protein (0.5 mg/mL final concentration) and MgCl$_2$ (1 mM final concentration) in 0.1 M potassium phosphate buffer (pH 7.4) at 37° C. for 15 minutes. The reaction was initiated by addition of 1 mM NADPH, followed by incubation at 37° C. A negative control was performed in parallel in the absence of NADPH to measure any chemical instability or non-NADPH dependent enzymatic degradation for each compound. At various time points (0, 5, 15, 30, and 60 minutes), 1 volume of reaction aliquot was taken and quenched with 3 volumes of acetonitrile containing an appropriate internal standard and 0.1% formic acid. The samples were then vortexed and centrifuged at 15,000 rpm for 5 minutes at 4° C. The supernatants were collected and analyzed by LC-MS/MS to determine the in vitro metabolic half-life ($t_{1/2}$).

Plasma Stability Assay.

The plasma stability assay is performed in duplicate by incubating each selected compound (1 μM final concentration) in normal mouse and human plasma diluted to 80% with 0.1 M potassium phosphate buffer (pH 7.4) at 37° C. At 0 and 3 hours, aliquots of the plasma mixture are taken and quenched with 3 volumes of acetonitrile containing an appropriate internal standard and 0.1% of formic acid. The quenched samples are filtered through the 0.2 μm Agilent Captiva filtration plates and analyzed by LC-MS/MS.

Stability data for representative compounds of the invention is provided in the following table.

| Example | HLM[a] | HLM[a] (+Cobi[c]) | MLM[b] | MLM[b] (+Cobi[c]) |
|---|---|---|---|---|
| (structure) | 7 | — | 1 | — |
| (structure) | 2.5 | 433 | 1.1 | 20 |
| (structure) | 1.5 | — | 0.6 | — |
| (structure) | 6.7 | 107 | 1.4 | 34 |
| (structure) | 1.8 | — | 0.5 | — |

-continued

| Example | HLM [a] | HLM [a] (+Cobi [c]) | MLM [b] | MLM [b] (+Cobi [c]) |
|---|---|---|---|---|
| (naphthalen-2-ylacetyl-Phe-N-methyl-4-chloroanilide structure) | 2.7 | 239 | 1.4 | 18 |
| (naphthalen-1-ylacetyl-Phe-N-methylanilide structure) | 0.6 | — | 0.5 | — |
| (naphthalen-1-ylacetyl-Phe-N-methyl-4-chloroanilide structure) | 1.1 | 102 | 0.6 | 7.4 |
| (quinazolinedione-Gly-Phe-Pro-anilide structure) | 31 | 578 | 2.9 | 85 |
| (cyclohexane-spiro-hydantoin-Gly-Phe-N-methyl-4-methoxyanilide structure) | 5.2 | — | 0.7 | — |

-continued

| Example | HLM[a] | HLM[a] (+Cobi[c]) | MLM[b] | MLM[b] (+Cobi[c]) |
|---|---|---|---|---|
| (hydantoin-spirocyclohexane-CH2-C(O)-NH-CH(CH2Ph)-C(O)-N(Me)-(4-methylphenyl)) | 3.3 | — | 1.2 | — |
| (hydantoin-spirocyclohexane-CH2-C(O)-NH-CH(CH2Ph)-C(O)-N(Me)-(4-fluorophenyl)) | 1.1 | — | 0.5 | — |
| (hydantoin-spirocyclohexane-CH2-C(O)-NH-CH(CH2Ph)-C(O)-N(Me)-(4-chlorophenyl)) | 3.1 | — | 0.9 | — |
| (PhC(O)-NH-CH2-C(O)-NH-CH(CH2Ph)-C(O)-N(CH3)-Ph) | 15 | — | 3.6 | — |
| (PhC(O)-NH-CH2-C(O)-NH-CH(CH2Ph)-C(O)-N(CH3)-(4-methylphenyl)) | 22 | 42 | 5.0 | 34 |

| Example | HLM[a] | HLM[a] (+Cobi[c]) | MLM[b] | MLM[b] (+Cobi[c]) |
|---|---|---|---|---|
| 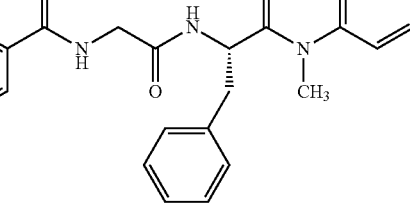 | 36 | 141 | 13 | 52 |
| 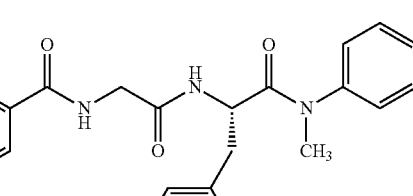 | 12 | — | 3.6 | — |
| 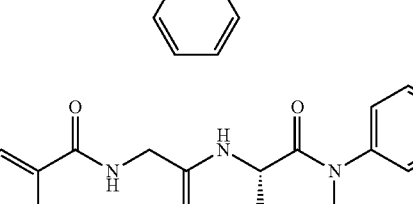 | 14 | 231 | 2.4 | 28 |
| 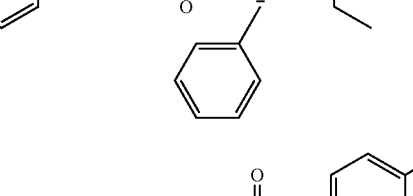 | 12 | 1386 | 4.6 | 385 |
| PF-74 [c] | 0.7 | 91 | 0.6 | 34 |
| Verapamil | 15 | — | 4.2 | — |

[a] HLM: human liver microsome;
[b] MLM: mouse liver microsome;
[c] Microsomal stability measured in the absence and presence of CYP3A inhibitor Cobi.

Example 78

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |

| (i) Tablet 1 | mg/tablet |
|---|---|
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |

-continued

| (ii) Tablet 2 | mg/tablet |
|---|---|
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I, formula II, or formula III:

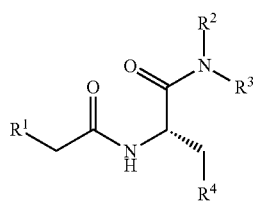

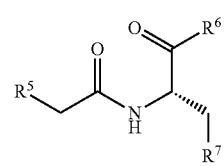

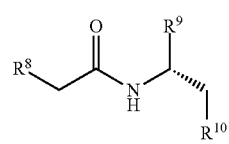

or a salt thereof, wherein:

$R^1$ is selected from the group consisting of:

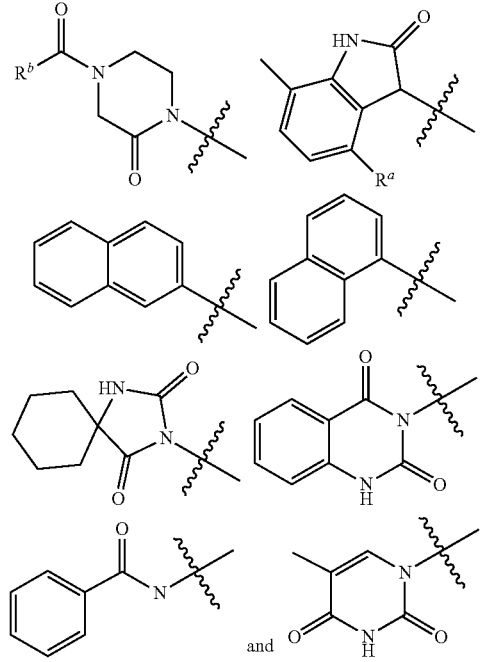

and $R^2$ is methyl or ethyl;

$R^3$ is phenyl, optionally substituted at the 3-position with bromo, chloro, fluoro, methyl, or methoxy, and optionally substituted at the 4-position with bromo, chloro, fluoro, methyl, or methoxy;

$R^4$ is 4-chloropyridyl, 4-bromopyridyl, or phenyl that is optionally substituted at the 4-position with halo, methyl, ethyl, or methoxy;

101

R⁵ is selected from the group consisting of:

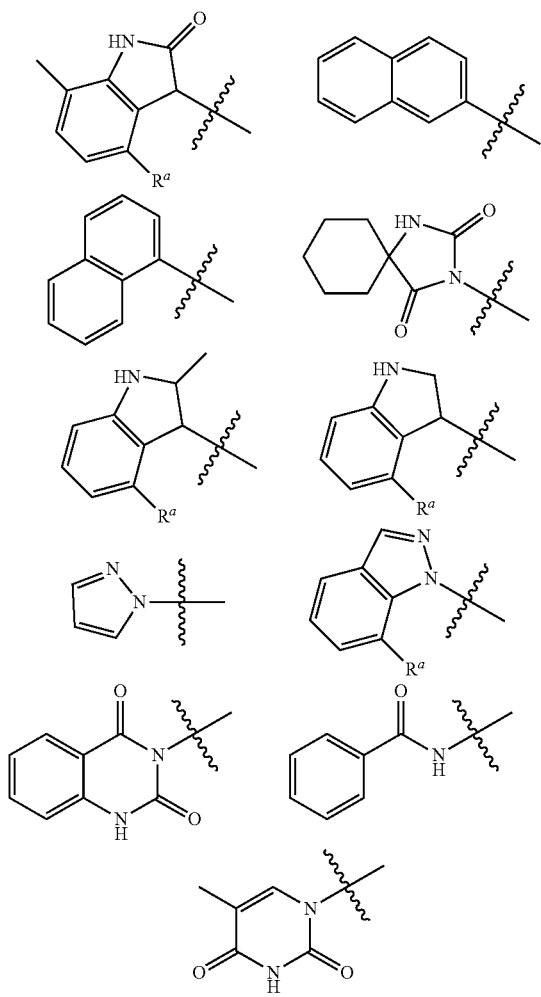

R⁶ is a ring:

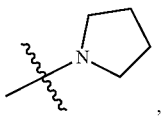 [SMILES: *N1CCCC1]

which ring is optionally substituted with carboxy, (C₁-C₆)alkoxycarbonyl, or —C(=O)NR^c R^d;

R⁷ is 4-chloropyridyl, 4-bromopyridyl, or phenyl that is optionally substituted at the 4-position with halo, methyl, ethyl, or methoxy;

R⁸ is selected from the group consisting of:

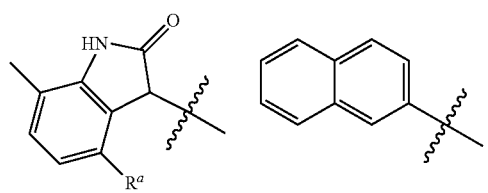

-continued

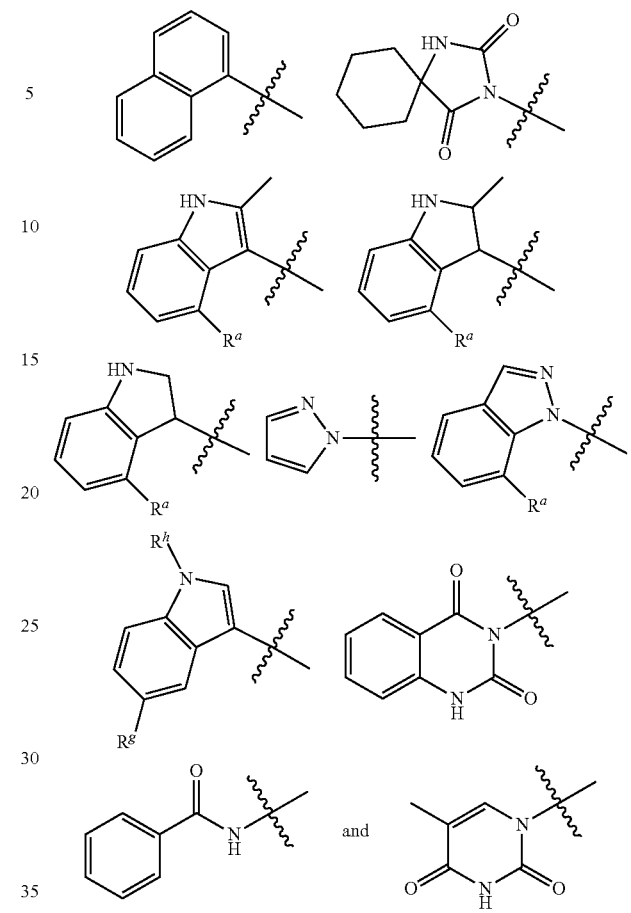

R⁹ is pyridyl that is substituted with phenyl, 4-chlorophenyl, 4-bromophenyl, 4-iodophenyl, or 4-cyanophenyl or R⁹ is imidazole that is substituted with phenyl, 4-chlorophenyl, 4-bromophenyl, 4-iodophenyl, or 4-cyanophenyl;

R¹⁰ is 4-chloropyridyl, 4-bromopyridyl, or phenyl that is optionally substituted at the 4-position with halo, methyl, ethyl, or methoxy;

R^a is H or methyl;

R^b is phenyl that is optionally substituted with one or more groups independently selected from the group consisting of nitro, halo, (C₁-C₆)alkyl, halo(C₁-C₆)alkyl, hydroxy, —SO₂F, and NR^e R^f;

R^c is H, phenyl, benzyl, or (C₁-C₆)alkyl;

R^d is H, phenyl, benzyl, or (C₁-C₆)alkyl;

R^e is H, hydroxy, or (C₁-C₆)alkyl;

R^f is H or (C₁-C₆)alkyl;

R^g is H, OH, or (C₁-C₆)alkoxy; and

R^h is H or (C₁-C₆)alkyl.

2. The compound or salt of claim 1, which is a compound of formula I or a salt thereof.

3. The compound or salt of claim 1, which is a compound of formula II or a salt thereof.

4. The compound or salt of claim 1, which is a compound of formula III or a salt thereof.

5. The compound or salt of claim 1, which is a compound of formula Ia:

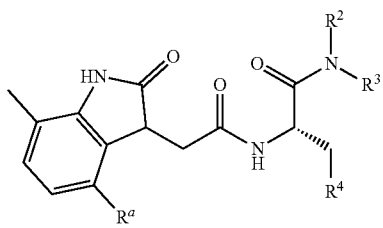

or a salt thereof.

6. The compound or salt of claim 1, which is a compound of formula Ib:

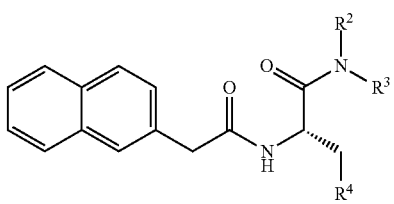

or a salt thereof.

7. The compound or salt of claim 1, which is a compound of formula Ic:

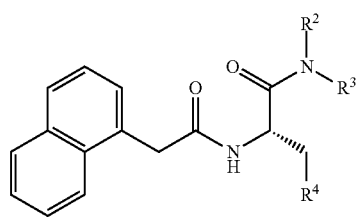

or a salt thereof.

8. The compound or salt of claim 1, which is a compound of formula Ie:

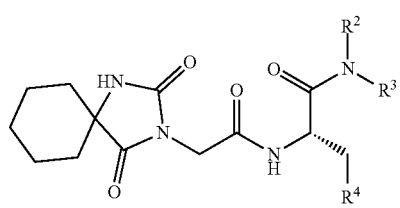

or a salt thereof.

9. The compound or salt of claim 1, which is a compound of formula Ig:

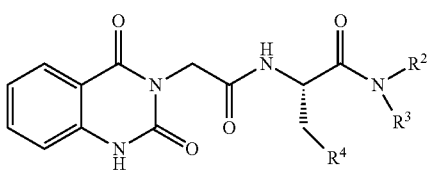

or a salt thereof.

10. The compound or salt of claim 1, which is a compound of formula Ih:

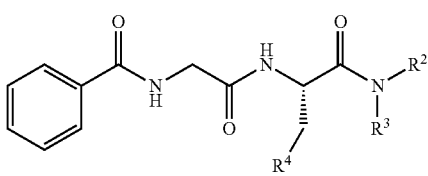

or a salt thereof.

11. The compound or salt of claim 1, which is a compound of formula

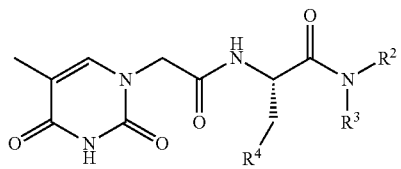

or a salt thereof.

12. The compound or salt of claim 1, which is a compound of formula In:

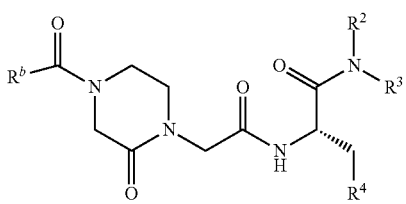

or a salt thereof.

13. The compound or salt of claim 1, which is a compound of formula (II), wherein $R^6$ is:

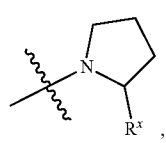

wherein $R^x$ is carboxy, $(C_1$-$C_6)$alkoxycarbonyl, or —C(=O)N$R^e R^d$; or a salt thereof.

14. The compound or salt of claim 1, which is a compound of formula (II), wherein $R^6$ is:

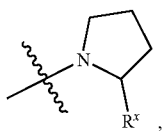

wherein $R^x$ is —C(=O)$NR^eR^d$; or a salt thereof.

15. The compound or salt of claim 1, which is a compound of formula IIIa:

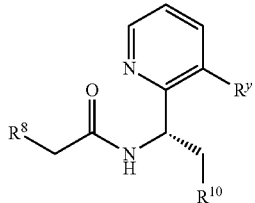

or a salt thereof, wherein $R^y$ is phenyl.

16. The compound or salt of claim 1, which is a compound of formula IIIb

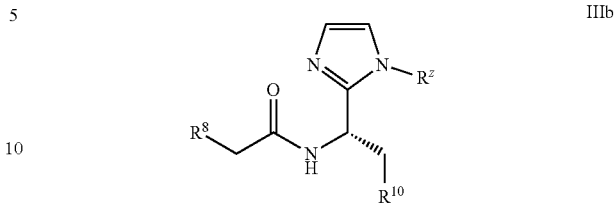

or a salt thereof, wherein $R^z$ is phenyl or 4-cyanophenyl.

17. A pharmaceutical composition comprising a compound as described in claim 1 and a pharmaceutically acceptable excipient.

18. The pharmaceutical composition of claim 17, that further comprises, a cytochrome P450 inhibitor.

19. The compound:

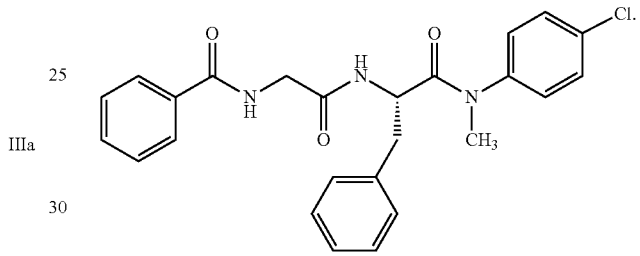

20. A pharmaceutical composition comprising: 1) a compound as described in claim 19, 2) a pharmaceutically acceptable excipient, and optionally, 3) a cytochrome P450 inhibitor.

* * * * *

UNITED STATES PATENT AND TRADEMARK OFFICE
CERTIFICATE OF CORRECTION

PATENT NO. : 11,850,247 B2
APPLICATION NO. : 17/222433
DATED : December 26, 2023
INVENTOR(S) : Zhengqiang Wang and Stefanos G. Sarafianos It is certified that error appears in the above-identified patent and that said Letters Patent is hereby corrected as shown below:

In the Claims

Column 104, Line 67, Claim 13, please delete "-C(=O)NR$^e$R$^d$; or" and insert -- -C(=O)NR$^c$R$^d$; or --;

Column 105, Line 18, Claim 14, please delete "-C(=O)NR$^e$R$^d$; or" and insert -- -C(=O)NR$^c$R$^d$; or -- therefor.

Signed and Sealed this
Twenty-seventh Day of August, 2024

Katherine Kelly Vidal
*Director of the United States Patent and Trademark Office*